United States Patent
Mommert et al.

(10) Patent No.: US 12,071,670 B2
(45) Date of Patent: Aug. 27, 2024

(54) METHOD FOR DETERMINING IN VITRO OR EX VIVO THE IMMUNE STATUS OF AN INDIVIDUAL

(71) Applicant: BIOMÉRIEUX, Marcy l'Etoile (FR)

(72) Inventors: Marine Mommert, Lyons (FR); Olivier Tabone, Lyons (FR); Julien Textoris, Villeurbanne (FR); François Mallet, Villeurbanne (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 370 days.

(21) Appl. No.: 17/256,811

(22) PCT Filed: Jun. 28, 2019

(86) PCT No.: PCT/EP2019/067330
§ 371 (c)(1),
(2) Date: Dec. 29, 2020

(87) PCT Pub. No.: WO2020/002602
PCT Pub. Date: Jan. 2, 2020

(65) Prior Publication Data
US 2021/0254165 A1 Aug. 19, 2021

(30) Foreign Application Priority Data

Jun. 29, 2018 (EP) ..................................... 18180991
Sep. 12, 2018 (FR) ..................................... 18/58167

(51) Int. Cl.
*C12Q 1/6883* (2018.01)
(52) U.S. Cl.
CPC ..... *C12Q 1/6883* (2013.01); *C12Q 2600/158* (2013.01)
(58) Field of Classification Search
None
See application file for complete search history.

(56) References Cited

U.S. PATENT DOCUMENTS

2016/0319352 A1  11/2016  Jakoubova et al.

FOREIGN PATENT DOCUMENTS

| EP | 2 186 913 A2 | 5/2010 |
| EP | 2 565 270 A1 | 3/2013 |
| WO | 2013/156627 A1 | 10/2013 |

OTHER PUBLICATIONS

Palmer et al BMC Genomics. 2006. 7:115 (Year: 2006).*
Murphy et al. Pathology, 2005, vol. 37(4), pp. 271-277 (Year: 2005).*
Min et al BMC Genomics. 2010. 11:96 (Year: 2010).*
Hanke et al. Clinical Chemistry. 2007. 53: 2070-2077 (Year: 2007).*
Tabone et al (Cold Spring Harbor Laboratory. bioRvix, Oct. 3, 2018. p. 1-28, available via URL: < biorxiv.org/content/10.1101/433029v1> (Year: 2018).*
Tabone et al Frontiers in Immunology. Jan. 8, 2019. 9 (3091), p. 1-12 and Supplemental Table 3 for the septic shock cohorts, 16 pages total (Year: 2019).*
Mommert et al BMC Genomics. Jul. 5, 2018. 19:522, p. 1-17 and Supplementary Methods (4 pages), and Table S2, 61 pages total (Year: 2018).*
Aug. 2, 2019 Written Opinion issued in International Patent Application No. PCT/EP2019/067330.
Peronnet, Estelle et al., Association between mRNA expression of CD74 and IL10 and risk of ICU-acquired infections: a multicenter cohort study Intensive Care Med, vol. 43, pp. 1013-1020, 2017.
Singer, Mervyn et al., "The Third International Consensus Definitions for Sepsis and Septic Shock (Sepsis-3)" Clinical Review & Education, vol. 315, No. 8, 2016.
Monneret, Guillaume et al., "Sepsis-Induced Immune Alterations Monitoring by Flow Cytometry as a Promising Tool for Individualized Therapy", Cytometry Part B, pp. 376-386, 2016.
Becker, Jérémie et al., "A comprehensive hybridization model allows whole HERV transcriptome profiling using high density microarray" BMC Genomics, vol. 18, No. 286, 2017.
Monneret, Guillaume et al., Monocyte HLA-DR in sepsis: shall we stop following the flow? Critical Care, vol. 18, No. 102, 2014.
Aug. 2, 2019 International Search Report issued in International Patent Application No. PCT/EP2019/067330.

* cited by examiner

*Primary Examiner* — Carla J Myers
(74) *Attorney, Agent, or Firm* — Oliff PLC

(57) ABSTRACT

A method for determining in vitro or ex vivo the immune status of an individual, preferably a patient, including a step of detecting and/or quantifying the expression of one or more HERV/MaLR sequences in a biological sample of the individual. Also relates to the tools for implementing the method and to the uses thereof.

15 Claims, 9 Drawing Sheets

Figure 1:
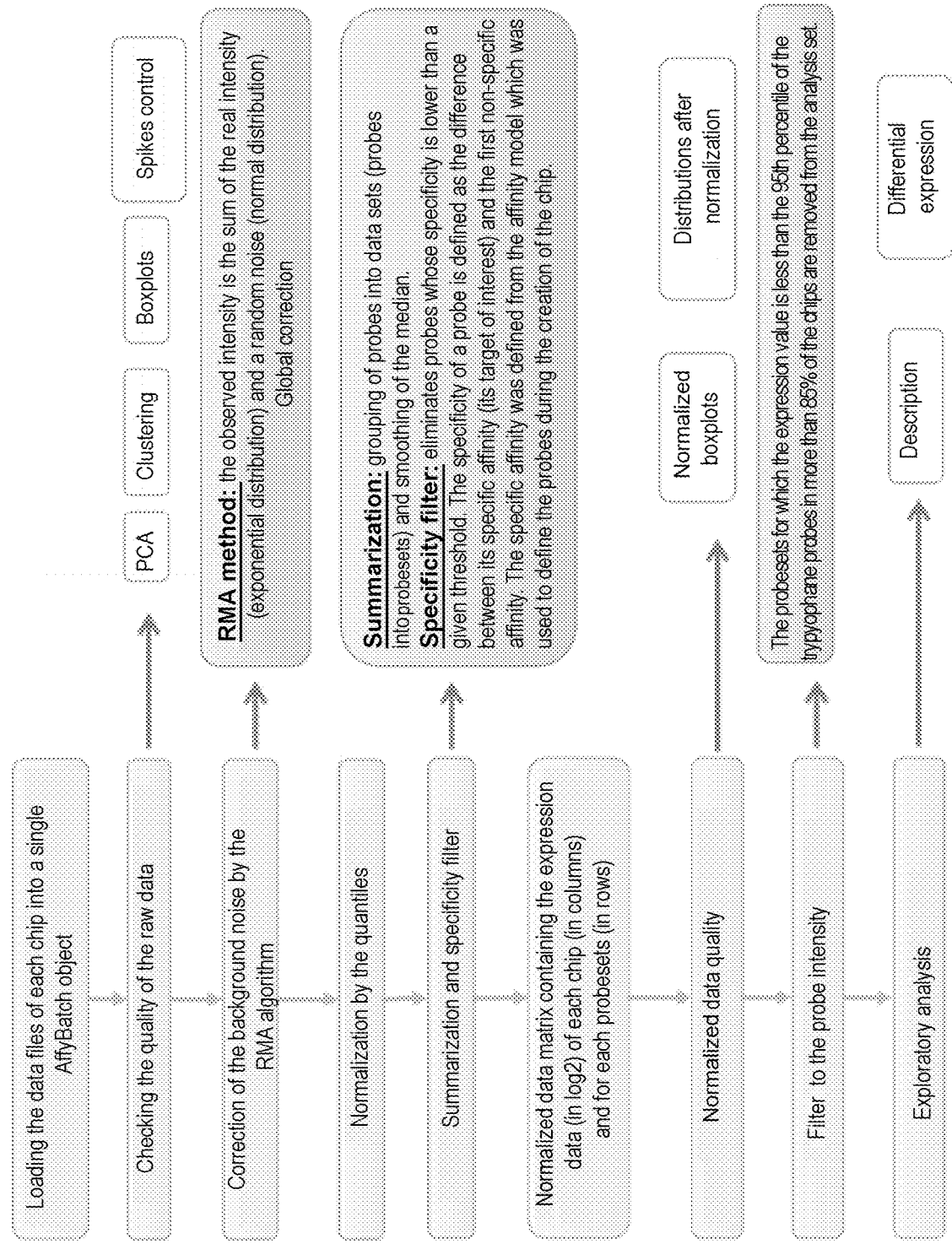

Specification includes a Sequence Listing.

METHOD FOR DETERMINING IN VITRO OR EX VIVO THE IMMUNE STATUS OF AN INDIVIDUAL

The present invention relates to a method for determining in vitro or ex vivo the immune status of an individual, preferably a patient, comprising a step of detecting and/or quantifying the expression, in a biological sample of said individual, of one or several sequences of HERV/MaLR, as well as the tools for implementing it and the uses thereof.

The immune system is a system for defending the body against what is recognized as non-self, such as pathogens (e.g. viruses, bacteria, parasites). In mammals, there are two main types of mechanisms: a non-specific defense mechanism, also called «innate» or «natural» immunity, and a specific defense mechanism, also called «acquired» or «adaptive» immunity.

These immune responses require very fine regulation. In a healthy individual, the immune response will be qualified as «normal» (we can also speak of immune status of immunocompetence). However, the immune response can sometimes be impaired. We will talk about inflammation status or hyperactive immune status when the immune system is more active than normal, as in the case of inflammatory or autoimmune diseases. In autoimmune diseases, the immune system of the body triggers an inflammatory response with characterized immunization against antigens of the self. Conversely, we will talk about immunosuppression status (or immunodepression or immunodeficiency or hypoactive immune status or immune paralysis), when the immune system is less active than normal.

The immunosuppression can have various origins, take many forms, and affect innate immunity and/or adaptive immunity. Particularly, the sepsis is a major public health problem, which is the leading cause of death in intensive care units. It is estimated that 28 million people develop sepsis each year worldwide, among which 8 million will die of the pathology (Fleischmann et al. (2016) American journal of respiratory and critical care medicine; 193(3): 259-72). In a patient with sepsis (also known as in a septic state), the immune response is deregulated, following an infection, leading to multiple and potentially fatal organ failure and dysfunction. This immune response is complex and evolves over time, with excessive pro-inflammatory and anti-inflammatory phenomena which may be concomitant. All of these immune system disorders lead to organ failure, immune system paralysis, and secondary infections. The septic shock is a subtype of sepsis, in which hypotension persists despite adequate vascular filling (Singer et al (2016) JAMA; 315 (8): 801-810). In the initial stage of sepsis, an inflammatory or even hyper-inflammatory response seems to predominate, which is the cause of tissue damage and organ failure, in particular in the kidney. This is why clinical trials in the field of sepsis have long focused on anti-inflammatory treatments, but with inconclusive results. More recent studies on the pathophysiology of sepsis have shown that an anti-inflammatory or immunosuppression response occurs in some patients in septic state, either concomitantly with the initial inflammation or later. The patient may then be in a state of immunosuppression, which may potentially be severe, depending on the respective degrees of pro-inflammatory and anti-inflammatory responses. These immunodepressed patients present a high risk of developing nosocomial infections (or HAI, Health-care Associated Infections), and could advantageously benefit from immunostimulatory treatments.

It therefore appears important to be able to determine the immune status of an individual, and particularly to be able to identify an immunosuppression status, in order to be able to adapt the therapeutic management. Yet, individuals with immune system disorders do not present specific clinical signs. There is therefore a significant need for the identification of biomarkers, which make it possible to determine the immune status of an individual.

Currently, the reference test for monitoring immune alterations in intensive care patients (e.g. patients with sepsis, trauma, major surgery, burns, or patients with pancreatitis) is the decreased expression of the HLA-DR (human leukocyte antigen-D related) on the surface of monocytes (mHLA-DR), measured by flow cytometry. Indeed, this marker provides valuable information in terms of prediction of mortality or the assessment of the secondary infections risk in these patients. The HLA-DR is a surface receptor belonging to the MHC (major histocompatibility complex) class II. In particular, the measurement of the mHLA-DR expression represents the gold standard for identifying whether a patient with sepsis is immunodepressed or not (Monneret and Venet (2016) Cytometry Part B (Clinical Cytometry) 90B: 376-386). However, this approach requires extensive pre-analytical sample manipulation (Monneret and Venet (2014) HLA-DR monocyte in sepsis: shall we stop following the flow? Crit Care 18: 102). Moreover, the accessibility to a flow cytometer is not always possible in all hospitals, and the measurement is difficult to standardize from one hospital to another, or even from one operator to another.

To overcome these drawbacks, other biomarkers, using molecular biology tools, have been proposed, such as for example a biomarker based on the ratio of the expression level, at the mRNA level, of CD74 on day D3 (following admission of the patient within a medical facility) on the CD74 expression level on day D1. The CD74 represents the invariant chain γ of HLA-DR. The CD74 D3/D1 expression ratio has been demonstrated to be associated with the onset of secondary infections acquired in intensive care (Peronnet et al (2017) Intensive Care Medicine; 43(7): 1013-20). The patent application WO2012/101387 describes a method for determining the immune status of an individual, from the analysis of the expression of at least two genes selected from several groups of genes. It has also been proposed, in the patent application WO2013/156627, a method for determining the immunodepressed or non-immunodepressed status, from the determination of the anellovirus load, in a biological sample. However, none of these biomarkers have yet come to replace the use of mHLA-DR. These biomarkers have the particular drawback of not making it possible to identify in which phase the patient is (i.e. inflammatory phase versus immunosuppressive phase), their objective being primarily to be able to identify immunodepressed patients, for whom it would be relevant to administer immunostimulant treatments.

At the date of the present invention, it therefore remains necessary to find new biomarkers, which make it possible to determine the immune status of an individual.

The endogenous retroviruses, or ERVs (for Endogenous RetroVirus) designate stable sequences of the genome of an organism and having structural analogies with certain infectious exogenous retroviruses (including the presence of two LTRs, or Long Terminal Repeats, which surround the genes encoding for putative proteins). Their origin is uncertain, but the most likely hypothesis is that of germ cell infection with a retrovirus. Following mutations in the retrovirus which would have made it defective, the infected germ cells could have survived, and the genome of the retrovirus, integrated into the genome of the organism, could have been transmitted to the next generation, and persist in the offspring within the genome of the organism.

In humans, HERVs (Human Endogenous RetroViruses) have only been demonstrated since the sequencing of the human genome. Together with MaLRs (Mammalian apparent LTR-Retrotransposons), which have a similar structure to HERVs, they represent 8.3% of the human genome, with a number of over 400,000 elements. By comparison, the 30,000 to 40,000 genes encoding proteins represent only 2% of human DNA. HERVs are subdivided into three major classes (I, II and Ill) and several groups (sometimes called «families» in the present patent application). HERVs are retroelements that are transposed only by a copy and paste mode, through an RNA intermediate and reverse transcriptase. They have long been considered as «junk DNA». While they may be inactive due to mutations or through epigenetic mechanisms, their role begins to appear, both in physiological and pathological contexts. Thus, it has been shown that HERV-W participates in one of the mechanisms ensuring the formation of the placenta. The HERV-K superfamily is the most studied in relation to carcinogenesis. The expression of certain HERVs has also been described in certain autoimmune diseases, such as multiple sclerosis or lupus erythematosus, and in interferonopathies, without any suggestion of a possible link between reactivation of HERVs and the immune status.

Thus, it has never been described or suggested that analyzing the expression of HERV in humans could be useful to determine the immune status of an individual. Furthermore, the reactivation of HERV has never been described in the pathology of sepsis.

Yet, it was discovered that, completely unexpectedly, among the approximately 420,000 existing HERV/MaLR, the analysis of the expression of some of them made it possible to determine the immune status of an individual.

Thus, the present invention relates to a method for determining in vitro or ex vivo the immune status of an individual, preferably a patient, comprising a step of detecting and/or quantifying the expression, in a biological sample of said individual (or biological test sample), of at least a part, preferably of a size of at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30 nucleotides, of at least one HERV/MaLR sequence selected from the sequences identified in SEQ ID NO: 1 to 34 or from the sequences which exhibit at least 99%, preferably at least 99.1%, preferably at least 99.2%, preferably at least 99.3%, preferably at least 99.4%, preferably at least 99.5%, preferably at least 99.6%, preferably at least 99.7%, preferably at least 99.8%, preferably at least 99.9% of identity with one of the sequences identified in SEQ ID NO: 1 to 34, from the following lists:

TABLE 1

List 1

| SEQ ID NO: | GRCh38 Location | Name of the probeset corresponding to the HERV-V3 chip | HERV/MaLR group name |
|---|---|---|---|
| 1 | chr19:54891074-54891496 | 190665001-HERV0376 | HERV0376 |
| 2 | chr22:36153696-36154283 | 220247002-HERV0797 | HERV0797 |
| 3 | chr17:35505737-35508365 | 170369402HE41env | HERV-E41 |

TABLE 1-continued

List 1

| SEQ ID NO: | GRCh38 Location | Name of the probeset corresponding to the HERV-V3 chip | HERV/MaLR group name |
|---|---|---|---|
| 4 | chr12:112971073-112971451 | 121601801-HERV0492 | HERV0492 |
| 5 | chr1:78648318-78648697 | 011052702-MALR1044 | MALR1044 |
| 6 | chr1:78623489-78623954 | 011052202-HERV1033 | HERV1033 |
| 7 | chr13:42884951-42886257 | 130360601-HERV0808 | HERV0808 |
| 8 | chr14:91230494-91230820 | 141107102-MALR1019 | MALR1019 |
| 9 | chr2:102363654-102366601 | 021460102-HERV0599uL | HERV0599 |
| 10 | chr2:102013616-102013971 | 021456001-MALR1017uL | MALR1017 |
| 11 | chr5:14551189-14551685 | 050286701-HERV0513 | HERV0513 |
| 12 | chr5:14562791-14563322 | 050287402-MALR1022 | MALR1022 |

TABLE 2

List 2

| SEQ ID NO: | GRCh38 Location | Name of the probeset corresponding to the HERV-V3 chip | HERV/MaLR group name |
|---|---|---|---|
| 13 | chr5:132453630-132454148 | 052182701-MALR1129 | MALR1129 |
| 14 | chr19:41812466-41813010 | 190478501-MALR1003 | MALR1003 |
| 15 | chr1:155637287-155637547 | 011790601ERV9sLU5 | ERV9 |
| 16 | chr5:170290289-170290812 | 052681601-MALR1018 | MALR1018 |
| 17 | chr16:50662453-50662912 | 160627301-MALR1014 | MALR1014 |
| 18 | chr11:122671887-122672147 | 111686702-HERV0861 | HERV0861 |
| 8 | chr14:91230494-91230820 | 141107102-MALR1019 | MALR1019 |
| 19 | chr4:15825146-15825565 | 040318302-MALR1134 | MALR1134 |
| 20 | chr4:83464568-83464963 | 041529101-MALR1026 | MALR1026 |
| 21 | chr14:91222760-91223118 | 141106902-MALR1133 | MALR1133 |

TABLE 3

List 3

| SEQ ID NO: | GRCh38 Location | Name of the probeset corresponding to the HERV-V3 chip | HERV/MaLR group name |
|---|---|---|---|
| 1 | chr19:54891074-54891496 | 190665001-HERV0376 | HERV0376 |
| 1 | chr19:54891074-54891496 | 190665002-HERV0376 | HERV0376 |
| 22 | chr6:18403673-18404108 | 060281701-MALR1043 | MALR1043 |
| 23 | chr4:184850413-184850785 | 043166601-MALR1018 | MALR1018 |
| 24 | chr10:5856198-5856795 | 100090601-HERV0429 | HERV0429 |
| 25 | chr6:107800650-107801138 | 061529601-HERV0492 | HERV0492 |
| 26 | chr10:60410534-60411224 | 100871501-MALR1020 | MALR1020 |
| 27 | chr17:78345106-78345577 | 170842002-MALR1003 | MALR1003 |

TABLE 4

List 4

| SEQ ID NO: | GRCh38 Location | Name of the probeset corresponding to the HERV-V3 chip | HERV/MaLR group name |
|---|---|---|---|
| 28 | chr8:125945973-125951030 | 081921103-HERV0958 | HERV0958 |
| 29 | chr3:167401329-167401866 | 032622601MR41sLU5p | MR41 |
| 30 | chr22:36147793-36148208 | 220246901-HERV0889 | HERV0889 |
| 31 | chr6:127790579-127792191 | 061827101-HERV0856 | HERV0856 |
| 3 | chr17:35505737-35508365 | 170369402HE41env | HERV-E41 |
| 32 | chr17:77462942-77463350 | 170828901-HERV0770 | HERV0770 |
| 28 | chr8:125945973-125951030 | 081921101-HERV0958 | HERV0958 |
| 28 | chr8:125945973-125951030 | 081921102-HERV0958 | HERV0958 |

TABLE 4-continued

List 4

| SEQ ID NO: | GRCh38 Location | Name of the probeset corresponding to the HERV-V3 chip | HERV/ MaLR group name |
|---|---|---|---|
| 33 | chr19:14612123-14612747 | 190148802-MALR1127 | MALR1127 |
| 34 | chr12:9038254-9038598 | 120093401-HERV1034 | HERV1034 |

In the context of the present invention:

«determining the immune status» of an individual means evaluating the capacity of the body to implement an immune response and to defend against attacks or infections. The immune status can in particular be determined as being a normal immune status (or immunocompetence status), an inflammation status (or hyperactive immune status) when the immune system is more active than normal, or an immunosuppression status (or immunodepression or immunodeficiency or hypoactive immune status or immune paralysis), when the immune system is less active than normal.

The term «HERV/MaLR» means the elements of the HERV and MaLR type, as presented in the introduction. The abbreviated term «HERV» may also sometimes be used, and have the same meaning as «HERV/MaLR». In the literature, many aliases have been used to describe the same HERV element or the same group (or family) of HERV, and there is still a need for standardization to this day. In the present application, to avoid any confusion, reference will firstly be made, in order to determine the identity of a HERV element, to the chromosomal location of said HERV element, more particularly on the basis of the GRCh38 (Genome Reference Consortium Human Build 38). We can also sometimes refer to the different probesets and the different probes of the HERV-V3 chip targeting said HERV element. It should also be noted that, for a given HERV element, as identified by its GRCh38 location, the sequences found in different individuals may differ from the sequence indicated in the GRCh38 base, due to polymorphism (Wildschutte et al (2016), *Discovery of unfixed endogenous retrovirus insertions in diverse human populations*, PNAS 113 (16): E2326-34).

The term «individual» designates a human being, whatever his state of health. A «healthy individual» within the meaning of the present invention is an individual who does not exhibit any dysregulation of the immune system. The term «patient» refers to an individual who has come into contact with a healthcare professional, such as a physician (for example, a general practitioner) or medical facility (for example, a hospital emergency or resuscitation service or intensive care unit)

The term «detection of the expression of a sequence» means the demonstration of the expression of said sequence, without necessarily a quantitative measurement. In the case of an mRNA transcript, the detection can be carried out by a direct method, by any method known to one skilled in the art making it possible to determine the presence of said transcript in a sample, or by indirect detection of the transcript after transformation of said transcript into DNA, or after amplification of said transcript or after amplification of the DNA obtained after transformation of said transcript into DNA. The «quantification of the expression of a sequence» refers to the evaluation of the expression level of the sequence, quantitatively. Many methods exist for the detection of nucleic acids (see, for example, Kricka et al., Clinical Chemistry, 1999, No. 45 (4), p. 453-458; Relier G H et al., DNA Probes, 2nd Ed., Stockton Press, 1993, sections 5 and 6, p. 173-249).

The term «biological sample» refers to any sample from an individual, which can be of various natures, such as blood, serum, plasma, sputum, urine, stool, skin, cerebrospinal fluid, bronchoalveolar lavage fluid, saliva, gastric secretions, semen, seminal fluid, tears, spinal cord, trigeminal nerve ganglion, adipose tissue, lymphoid tissue, placental tissue, tissue of the gastrointestinal tract, tissue of the genital tract, tissue of the central nervous system. Particularly, this sample can be a biological fluid, preferably selected from the whole blood (as collected from the venous route, that is to say containing white and red cells, platelets and plasma), plasma and serum. It can also be any type of cells extracted from a blood sample, such as peripheral blood mononuclear cells (or PBMCs), B cell subpopulations, purified monocytes, or neutrophils.

In order to determine the «percentage of sequence identity» of one nucleic acid sequence with another nucleic acid sequence, the two sequences are first aligned optimally. The two sequences to be compared can be of the same size or of different sizes. In some cases, it may be necessary to introduce «holes» in one of the sequences, in order to allow optimal alignment with the second sequence. The optimal alignment of the sequences can in particular be carried out by using the algorithm of Smith and Waterman (J. Theor. Biol., 91 (2): 370-380, 1981), the algorithm of Needleman and Wunsch (J. Mol. Biol, 48 (3): 443-453, 1972), or the method of Pearson and Lipman (Proc. Natl. Acad. Sri. USA, 85 (5): 2444-2448, 1988). Some software allow to implementing some of these algorithms, such as GAP, BESTFIT, FASTA, TFASTA (Wisconsin Genetics Software Package Release 7.0, Genetic Computer Group, 575, Science Drive, Madison, Wisconsin), BLAST or even CLUSTALW (Nucleic Acids Res. 1994 Nov. 11; 22 (22): 4673-80. CLUSTAL W: *improving the sensitivity of progressive multiple sequence alignment through sequence weighting, position-specific gap penalties and weight matrix choice*). The best alignment (i.e. the one allowing to obtain the highest percentage of identity on the comparison window), among those generated by these various methods, is selected. The respective nucleotides located at the same position of each of the sequences are then compared. When a given position is occupied by the same nucleotide in both sequences, then the sequences are identical for that position. The percentage of sequence identity is then determined as a function of the number of positions for which the respective nucleotides are identical, relative to the total number of nucleotides of the positions for which the alignment has been possible, at the level of the comparison window.

A «biomarker» or «marker» is an objectively measurable biological characteristic which represents an indicator of normal or pathological biological processes or of pharmacological response to a therapeutic intervention. It may particularly be a molecular biomarker, preferably detectable at the mRNA level. More particularly, the biomarker can be an endogenous biomarker or loci (such as a HERV or a gene, which are found in the chromosomal material of an individual) or an exogenous biomarker (such as a virus).

The «sepsis» is a disease in which the immune response is deregulated in an individual, following an infection, leading to multiple organ failure and dysfunction and potentially fatal. The «septic shock» is a subtype of sepsis, in which hypotension persists despite adequate blood supply.

The term «amplification primer» means a nucleotide fragment which may comprise from 5 to 100 nucleotides, preferably from 15 to 30 nucleotides, and having a specificity of hybridization with a target nucleotide sequence, under conditions determined for the initiation of an enzymatic polymerization, for example in an enzymatic amplification reaction of the target nucleotide sequence. Generally, «pairs of primers», consisting of two primers, are used. When it is desired to carry out the amplification of several different HERVs, several different pairs of primers are preferably used, each preferably having an ability to specifically hybridize with a different HERV.

The term «hybridization probe» means a nucleotide fragment typically comprising from 5 to 100 nucleotides, preferably from 15 to 90 nucleotides, even more preferably from 15 to 35 nucleotides, having a specificity of hybridization under conditions determined to form a hybridization complex with a target nucleotide sequence. The probe also includes a reporter (such as a fluorophore, an enzyme or any other detection system), which will allow the detection of the target nucleotide sequence. In the present invention, the target nucleotide sequence can be a nucleotide sequence included in a messenger RNA (mRNA) or a nucleotide sequence comprised in a complementary DNA (cDNA) obtained by reverse transcription of said mRNA. When it is desired to target several different HERVs, several different probes are preferably used, each preferably having an ability to specifically hybridize with a different HERV.

The term «hybridization» means the process during which, under appropriate conditions, two nucleotide fragments, such as for example a hybridization probe and a target nucleotide fragment, having sufficiently complementary sequences, are capable of forming a double strand with stable and specific hydrogen bonds. A nucleotide fragment «capable of being hybridized» with a polynucleotide is a fragment capable of being hybridized with said polynucleotide under hybridization conditions, which can be determined in each case in a known manner. The hybridization conditions are determined by the stringency, that is to say the stringency of the operating conditions. The hybridization is all the more specific as it is carried out at higher stringency. The stringency is defined in particular as a function of the base composition of a probe/target duplex, as well as by the degree of mismatch between two nucleic acids. The stringency can also be a function of the reaction parameters, such as the concentration and the type of ionic species present in the hybridization solution, the nature and the concentration of denaturing agents and/or the hybridization temperature. The stringency of the conditions under which a hybridization reaction is to be performed will depend primarily on the used hybridization probes. All of these data are well known and the appropriate conditions can be determined by one skilled in the art. In general, depending on the length of the used hybridization probes, the temperature for the hybridization reaction is comprised between about 20 and 70° C., particularly between 35 and 65° C. in saline solution at a concentration of about 0.5 to 1 M. A step of detecting the hybridization reaction is then carried out.

The term «enzymatic amplification reaction» means a process generating multiple copies of a target nucleotide fragment, by the action of at least one enzyme. Such amplification reactions are well known to one skilled in the art and the following techniques may be mentioned in particular: PCR (Polymerase Chain Reaction), LCR (Ligase Chain Reaction), RCR (Repair Chain Reaction), 3SR (Self Sustained Sequence Replication) with the patent application WO-A-90/06995, NASBA (Nucleic Acid Sequence-Based Amplification), TMA (Transcription Mediated Amplification) with U.S. Pat. No. 5,399,491, and LAMP (Loop mediated isothermal amplification) with the U.S. Pat. No. 6,410,278. When the enzymatic amplification reaction is a PCR, we will speak more particularly of RT-PCR (RT for «reverse transcription»), when the amplification step is preceded by a messenger RNA (mRNA) reverse-transcription step into complementary DNA (cDNA), and from qPCR or RT-qPCR when PCR is quantitative.

To the knowledge of the inventors, it has never been described or suggested that the detection and/or the quantification of the expression of HERV/MaLR could make it possible to determine the immune status of an individual. Particularly, the involvement of HERV/MaLR has never been described in the field of sepsis.

All of the HERV/MaLRs of SEQ ID NO: 1 to 34 have been identified among the approximately 420,000 HERV/MaLRs in the genome. These are HERV/MaLR that we can target with the HERV-V3 chip (Becker et al, BMC Genomics. 2017; 18: 286). More particularly, these HERV/MaLR are expressed in the data sets used in the Examples. Even more particularly, these expressed HERV/MaLR are modulated between the conditions of interest retained in the Examples.

The detection and/or the quantification of the expression of the HERVs according to the present invention, to determine the immune status of an individual, can be carried out by means of molecular tools which have advantages relative to the use of flow cytometry for the measurement of mHLA-DR, in terms of accessibility within hospitals and standardization. Little sample manipulation is required and the results are easy to interpret. Moreover, the expression of HERVs according to the present invention can be detected and/or quantified on several types of platforms, such as DNA chips or by PCR, in order to determine the immune status. Some of the HERVs according to the present invention can be detected early, from D1, while the measurement of mHLA-DR is carried out on D3 (Monneret and Venet (2014) Monocyte HLA-DR in sepsis: shall we stop following the flow? Crit Care 18: 102).

Preferably, the present invention relates to a method for determining in vitro or ex vivo the immune status of an individual, preferably a patient, comprising:
  a step of detecting and/or quantifying the expression, in a biological sample of said individual (or test biological sample), of at least part of at least one HERV/MaLR sequence selected from the sequences identified in SEQ ID NO: 1 to 34 or from the sequences which have at least 99% identity with one of the sequences identified in SEQ ID NO: 1 to 34, from Lists 1 to 4, previously described;

a step in which the expression in the test biological sample is compared with a reference expression, or with the expression in a reference biological sample;

a step in which the immune status of the individual is determined from this comparison.

The reference biological sample can be of various natures, but it is preferably identical in nature, or at least similar in nature, to the nature of the test biological sample. For example, if the test biological sample is a whole blood sample, the reference biological sample will preferably be a whole blood sample, or possibly a plasma or serum sample. The biological reference sample can be a «natural» sample, that is to say from an individual whose immune status is known or determined according to a reference method (for example, by the mHLA-DR method). For example, it can be from an individual with an immune status known to be an immunocompetent status, an inflammation status, or an immunosuppression status. Preferably, if the test biological sample is from a human, the reference biological sample is also from a human. Even more preferably, the reference biological sample comes from the same individual as that from which the test biological sample comes. The reference biological sample can also be a «synthetic» sample, that is to say a sample containing a calibrated amount of at least one of the sequences SEQ ID NO: 1 to 34.

Preferably, the invention relates to a method for determining the immune status of an individual, as described above, in which the expression of at least 2 different sequences selected from the sequences identified in SEQ. Nos: 1 to 34 or from the sequences which exhibit at least 99% identity with one of the sequences identified in SEQ ID NO: 1 to 34 is detected and/or quantified. The lists 1 to 4 being complementary to each other, these at least two different sequences are preferably selected in two different lists.

Preferably, the invention relates to a method for determining the immune status of an individual, as described above, in which the expression of at least 3 different sequences selected from the sequences identified in SEQ ID NO: 1 to 34 or from the sequences which exhibit at least 99% identity with one of the sequences identified in SEQ ID NO: 1 to 34 is detected and/or quantified. These at least three different sequences are preferably selected from two different lists, more preferably from three different lists.

Preferably, the invention relates to a method for determining the immune status of an individual, as described above, in which the expression of at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34 different sequences selected from the sequences identified in SEQ ID NO: 1 to 34 or from the sequences which exhibit at least 99% identity with one of the sequences identified in SEQ ID NO: 1 to 34 is detected and/or quantified. These at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34 different sequences are preferably selected from two different lists, more preferably from three different lists, even more preferably from four different lists.

The HERVs of SEQ ID NO: 1, 3 and 8 were identified from two different strategies, as described in the Examples, and are thus found in two Lists respectively. Moreover, the inventors assigned a rating for the different sequences of HERV, as explained in Examples 4 to 6. In Example 7, the HERVs were ranked in order of importance. Also, quite preferably, the invention relates to a method for determining the immune status of an individual, as described above, in which the expression of at least 1, at least 2, at least 3, at least 4, at least 5, at least 6, at least 7 different sequences selected from the sequences identified in SEQ ID NO: 1, SEQ ID NO: 3, SEQ ID NO: 8, SEQ ID NO: 11, SEQ ID NO: 12, SEQ ID NO: 13 and SEQ ID NO: 28, or from the sequences which exhibit at least 99%, at least 99.1%, at least 99.2%, at least 99.3%, at least 99.4%, at least 99.5%, at least 99.6%, at least 99.7%, at least 99.8%, at least 99.9% identity with one of the sequences SEQ ID NO: 1, 3, 8, 11, 12, 13 and 28 is detected and/or quantified. Preferred combinations of at least 2 corresponding HERVs are listed in Table 5 below.

TABLE 5

Preferred combinations of at least 2 HERVs

| Number of HERV in the combination | Preferred combinations of at least 2 HERVs |
|---|---|
| 2 | SEQ ID NO: 1, SEQ ID NO: 3 |
|   | SEQ ID NO: 1, SEQ ID NO: 8 |
|   | SEQ ID NO: 1, SEQ ID NO: 11 |
|   | SEQ ID NO: 1, SEQ ID NO: 12 |
|   | SEQ ID NO: 1, SEQ ID NO: 13 |
|   | SEQ ID NO: 1, SEQ ID NO: 28 |
|   | SEQ ID NO: 3, SEQ ID NO: 8 |
|   | SEQ ID NO: 3, SEQ ID NO: 11 |
|   | SEQ ID NO: 3, SEQ ID NO: 12 |
|   | SEQ ID NO: 3, SEQ ID NO: 13 |
|   | SEQ ID NO: 3, SEQ ID NO: 28 |
|   | SEQ ID NO: 8, SEQ ID NO: 11 |
|   | SEQ ID NO: 8, SEQ ID NO: 12 |
|   | SEQ ID NO: 8, SEQ ID NO: 13 |
|   | SEQ ID NO: 8, SEQ ID NO: 28 |
|   | SEQ ID NO: 11, SEQ ID NO: 12 |
|   | SEQ ID NO: 11, SEQ ID NO: 13 |
|   | SEQ ID NO: 11, SEQ ID NO: 28 |
|   | SEQ ID NO: 12, SEQ ID NO: 13 |
|   | SEQ ID NO: 12, SEQ ID NO: 28 |
|   | SEQ ID NO: 13, SEQ ID NO: 28 |
| 3 | SEQ ID NO: 1, SEQ ID NO: 3, SEQ ID NO: 8 |
|   | SEQ ID NO: 1, SEQ ID NO: 3, SEQ ID NO: 11 |
|   | SEQ ID NO: 1, SEQ ID NO: 3, SEQ ID NO: 12 |
|   | SEQ ID NO: 1, SEQ ID NO: 3, SEQ ID NO: 13 |
|   | SEQ ID NO: 1, SEQ ID NO: 3, SEQ ID NO: 28 |
|   | SEQ ID NO: 1, SEQ ID NO: 8, SEQ ID NO: 11 |
|   | SEQ ID NO: 1, SEQ ID NO: 8, SEQ ID NO: 12 |
|   | SEQ ID NO: 1, SEQ ID NO: 8, SEQ ID NO: 13 |
|   | SEQ ID NO: 1, SEQ ID NO: 8, SEQ ID NO: 28 |
|   | SEQ ID NO: 1, SEQ ID NO: 11, SEQ ID NO: 12 |
|   | SEQ ID NO: 1, SEQ ID NO: 11, SEQ ID NO: 13 |
|   | SEQ ID NO: 1, SEQ ID NO: 11, SEQ ID NO: 28 |
|   | SEQ ID NO: 1, SEQ ID NO: 12, SEQ ID NO: 13 |
|   | SEQ ID NO: 1, SEQ ID NO: 12, SEQ ID NO: 28 |
|   | SEQ ID NO: 1, SEQ ID NO: 13, SEQ ID NO: 28 |
|   | SEQ ID NO: 3, SEQ ID NO: 8, SEQ ID NO: 11 |
|   | SEQ ID NO: 3, SEQ ID NO: 8, SEQ ID NO: 12 |
|   | SEQ ID NO: 3, SEQ ID NO: 8, SEQ ID NO: 13 |
|   | SEQ ID NO: 3, SEQ ID NO: 8, SEQ ID NO: 28 |
|   | SEQ ID NO: 3, SEQ ID NO: 11, SEQ ID NO: 12 |
|   | SEQ ID NO: 3, SEQ ID NO: 11, SEQ ID NO: 13 |
|   | SEQ ID NO: 3, SEQ ID NO: 11, SEQ ID NO: 28 |
|   | SEQ ID NO: 3, SEQ ID NO: 12, SEQ ID NO: 13 |
|   | SEQ ID NO: 3, SEQ ID NO: 12, SEQ ID NO: 28 |
|   | SEQ ID NO: 3, SEQ ID NO: 13, SEQ ID NO: 28 |
|   | SEQ ID NO: 8, SEQ ID NO: 11, SEQ ID NO: 12 |

TABLE 5-continued

Preferred combinations of at least 2 HERVs

| Number of HERV in the combination | Preferred combinations of at least 2 HERVs |
|---|---|
| | SEQ ID NO: 8, SEQ ID NO: 11, SEQ ID NO: 13 |
| | SEQ ID NO: 8, SEQ ID NO: 11, SEQ ID NO: 28 |
| | SEQ ID NO: 8, SEQ ID NO: 12, SEQ ID NO: 13 |
| | SEQ ID NO: 8, SEQ ID NO: 12, SEQ ID NO: 28 |
| | SEQ ID NO: 8, SEQ ID NO: 13, SEQ ID NO: 28 |
| | SEQ ID NO: 11, SEQ ID NO: 12, SEQ ID NO: 13 |
| | SEQ ID NO: 11, SEQ ID NO: 12, SEQ ID NO: 28 |
| | SEQ ID NO: 11, SEQ ID NO: 13, SEQ ID NO: 28 |
| | SEQ ID NO: 12, SEQ ID NO: 13, SEQ ID NO: 28 |
| 4 | SEQ ID NO: 1, SEQ ID NO: 3, SEQ ID NO: 8, SEQ ID NO: 11 |
| | SEQ ID NO: 1, SEQ ID NO: 3, SEQ ID NO: 8, SEQ ID NO: 12 |
| | SEQ ID NO: 1, SEQ ID NO: 3, SEQ ID NO: 8, SEQ ID NO: 13 |
| | SEQ ID NO: 1, SEQ ID NO: 3, SEQ ID NO: 8, SEQ ID NO: 28 |
| | SEQ ID NO: 1, SEQ ID NO: 3, SEQ ID NO: 11, SEQ ID NO: 12 |
| | SEQ ID NO: 1, SEQ ID NO: 3, SEQ ID NO: 11, SEQ ID NO: 13 |
| | SEQ ID NO: 1, SEQ ID NO: 3, SEQ ID NO: 11, SEQ ID NO: 28 |
| | SEQ ID NO: 1, SEQ ID NO: 3, SEQ ID NO: 12, SEQ ID NO: 13 |
| | SEQ ID NO: 1, SEQ ID NO: 3, SEQ ID NO: 12, SEQ ID NO: 28 |
| | SEQ ID NO: 1, SEQ ID NO: 3, SEQ ID NO: 13, SEQ ID NO: 28 |
| | SEQ ID NO: 1, SEQ ID NO: 8, SEQ ID NO: 11, SEQ ID NO: 12 |
| | SEQ ID NO: 1, SEQ ID NO: 8, SEQ ID NO: 11, SEQ ID NO: 13 |
| | SEQ ID NO: 1, SEQ ID NO: 8, SEQ ID NO: 11, SEQ ID NO: 28 |
| | SEQ ID NO: 1, SEQ ID NO: 8, SEQ ID NO: 12, SEQ ID NO: 13 |
| | SEQ ID NO: 1, SEQ ID NO: 8, SEQ ID NO: 12, SEQ ID NO: 28 |
| | SEQ ID NO: 1, SEQ ID NO: 8, SEQ ID NO: 13, SEQ ID NO: 28 |
| | SEQ ID NO: 1, SEQ ID NO: 11, SEQ ID NO: 12, SEQ ID NO: 13 |
| | SEQ ID NO: 1, SEQ ID NO: 11, SEQ ID NO: 12, SEQ ID NO: 28 |
| | SEQ ID NO: 1, SEQ ID NO: 11, SEQ ID NO: 13, SEQ ID NO: 28 |
| | SEQ ID NO: 1, SEQ ID NO: 12, SEQ ID NO: 13, SEQ ID NO: 28 |
| | SEQ ID NO: 3, SEQ ID NO: 8, SEQ ID NO: 11, SEQ ID NO: 12 |
| | SEQ ID NO: 3, SEQ ID NO: 8, SEQ ID NO: 11, SEQ ID NO: 13 |
| | SEQ ID NO: 3, SEQ ID NO: 8, SEQ ID NO: 11, SEQ ID NO: 28 |
| | SEQ ID NO: 3, SEQ ID NO: 8, SEQ ID NO: 12, SEQ ID NO: 13 |
| | SEQ ID NO: 3, SEQ ID NO: 8, SEQ ID NO: 12, SEQ ID NO: 28 |
| | SEQ ID NO: 3, SEQ ID NO: 8, SEQ ID NO: 13, SEQ ID NO: 28 |
| | SEQ ID NO: 3, SEQ ID NO: 11, SEQ ID NO: 12, SEQ ID NO: 13 |
| | SEQ ID NO: 3, SEQ ID NO: 11, SEQ ID NO: 12, SEQ ID NO: 28 |
| | SEQ ID NO: 3, SEQ ID NO: 11, SEQ ID NO: 13, SEQ ID NO: 28 |
| | SEQ ID NO: 3, SEQ ID NO: 12, SEQ ID NO: 13, SEQ ID NO: 28 |
| | SEQ ID NO: 8, SEQ ID NO: 11, SEQ ID NO: 12, SEQ ID NO: 13 |
| | SEQ ID NO: 8, SEQ ID NO: 11, SEQ ID NO: 12, SEQ ID NO: 28 |
| | SEQ ID NO: 8, SEQ ID NO: 11, SEQ ID NO: 13, SEQ ID NO: 28 |
| | SEQ ID NO: 8, SEQ ID NO: 12, SEQ ID NO: 13, SEQ ID NO: 28 |
| | SEQ ID NO: 11, SEQ ID NO: 12, SEQ ID NO: 13, SEQ ID NO: 28 |
| 5 | SEQ ID NO: 1, SEQ ID NO: 3, SEQ ID NO: 8, SEQ ID NO: 11, SEQ ID NO: 12 |
| | SEQ ID NO: 1, SEQ ID NO: 3, SEQ ID NO: 8, SEQ ID NO: 11, SEQ ID NO: 13 |
| | SEQ ID NO: 1, SEQ ID NO: 3, SEQ ID NO: 8, SEQ ID NO: 11, SEQ ID NO: 28 |
| | SEQ ID NO: 1, SEQ ID NO: 3, SEQ ID NO: 8, SEQ ID NO: 12, SEQ ID NO: 13 |
| | SEQ ID NO: 1, SEQ ID NO: 3, SEQ ID NO: 8, SEQ ID NO: 12, SEQ ID NO: 28 |
| | SEQ ID NO: 1, SEQ ID NO: 3, SEQ ID NO: 8, SEQ ID NO: 13, SEQ ID NO: 28 |
| | SEQ ID NO: 1, SEQ ID NO: 3, SEQ ID NO: 11, SEQ ID NO: 12, SEQ ID NO: 13 |
| | SEQ ID NO: 1, SEQ ID NO: 3, SEQ ID NO: 11, SEQ ID NO: 12, SEQ ID NO: 28 |
| | SEQ ID NO: 1, SEQ ID NO: 3, SEQ ID NO: 11, SEQ ID NO: 13, SEQ ID NO: 28 |
| | SEQ ID NO: 1, SEQ ID NO: 3, SEQ ID NO: 12, SEQ ID NO: 13, SEQ ID NO: 28 |
| | SEQ ID NO: 1, SEQ ID NO: 8, SEQ ID NO: 11, SEQ ID NO: 12, SEQ ID NO: 13 |
| | SEQ ID NO: 1, SEQ ID NO: 8, SEQ ID NO: 11, SEQ ID NO: 12, SEQ ID NO: 28 |
| | SEQ ID NO: 1, SEQ ID NO: 8, SEQ ID NO: 11, SEQ ID NO: 13, SEQ ID NO: 28 |
| | SEQ ID NO: 1, SEQ ID NO: 8, SEQ ID NO: 12, SEQ ID NO: 13, SEQ ID NO: 28 |
| | SEQ ID NO: 1, SEQ ID NO: 11, SEQ ID NO: 12, SEQ ID NO: 13, SEQ ID NO: 28 |
| | SEQ ID NO: 3, SEQ ID NO: 8, SEQ ID NO: 11, SEQ ID NO: 12, SEQ ID NO: 13 |
| | SEQ ID NO: 3, SEQ ID NO: 8, SEQ ID NO: 11, SEQ ID NO: 12, SEQ ID NO: 28 |
| | SEQ ID NO: 3, SEQ ID NO: 8, SEQ ID NO: 11, SEQ ID NO: 13, SEQ ID NO: 28 |
| | SEQ ID NO: 3, SEQ ID NO: 8, SEQ ID NO: 12, SEQ ID NO: 13, SEQ ID NO: 28 |
| | SEQ ID NO: 3, SEQ ID NO: 11, SEQ ID NO: 12, SEQ ID NO: 13, SEQ ID NO: 28 |
| | SEQ ID NO: 8, SEQ ID NO: 11, SEQ ID NO: 12, SEQ ID NO: 13, SEQ ID NO: 28 |
| 6 | SEQ ID NO: 1, SEQ ID NO: 3, SEQ ID NO: 8, SEQ ID NO: 11, SEQ ID NO: 12, SEQ ID NO: 13 |
| | SEQ ID NO: 1, SEQ ID NO: 3, SEQ ID NO: 8, SEQ ID NO: 11, SEQ ID NO: 12, SEQ ID NO: 28 |
| | SEQ ID NO: 1, SEQ ID NO: 3, SEQ ID NO: 8, SEQ ID NO: 11, SEQ ID NO: 13, SEQ ID NO: 28 |
| | SEQ ID NO: 1, SEQ ID NO: 3, SEQ ID NO: 8, SEQ ID NO: 12, SEQ ID NO: 13, SEQ ID NO: 28 |
| | SEQ ID NO: 1, SEQ ID NO: 3, SEQ ID NO: 11, SEQ ID NO: 12, SEQ ID NO: 13, SEQ ID NO: 28 |
| | SEQ ID NO: 1, SEQ ID NO: 8, SEQ ID NO: 11, SEQ ID NO: 12, SEQ ID NO: 13, SEQ ID NO: 28 |
| | SEQ ID NO: 3, SEQ ID NO: 8, SEQ ID NO: 11, SEQ ID NO: 12, SEQ ID NO: 13, SEQ ID NO: 28 |
| 7 | SEQ ID NO: 1, SEQ ID NO: 3, SEQ ID NO: 8, SEQ ID NO: 11, SEQ ID NO: 12, SEQ ID NO: 13, SEQ ID NO: 28 |

The method for determining in vitro or ex vivo the immune status of an individual, as described above, according to any embodiment, can also comprise a step of detecting and/or quantifying the expression, in the test biological sample, of at least one, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95 gene(s) selected from the following genes:

CD74, CX3CR1, IL-10, S100A8, S100A9, MERTK, CLEC7A, CD36, TIMP2, CCL13, PTGS2, IL-12B, IL-6, IL-1A, CCL20, MX1, OAS-1, CCL15, OAS-3, EIF2AK2, IFNγ, NEFH, MMP10, SERPINB2, THBD, STAT1, CCR4, HLA-DRB1/B3, TCF7, EOMES, BCL11B, ITGA7, IL-18R1, NLRC4, CYP1B1, HGF, IL-5RA, CCLP4, CD3G, CD40LG, CD3D, CD127, ICOS, IL-1R2, IL-1RN, IL-18, IL-18RAP, OX40L, PD-1, PD-L1, Zonulin (HP), BTLA, C3AR1, CD154, GM-CSF, IFIH1, IL-15, MCP1, PCSK9, STAT4, LTR82B, CIITA, LILRB2, CD177, ADGRE3, FLT-1, CD64, TREM-1, TNF-α, IL-1β, ALOX5, IL-17A, NFκB, TBX21, HIF1a, RORgT, OAS-2, GNLY, CTLA-4, TIM 3, CD274, IL-2, IL-7R, GATA3, CXCL10, FAS, GSN, MDC1, DYRK2, TDRD9, CNB1IP1, ZAP70 and ARL14EP.

Preferably, the invention relates to a method for determining the immune status of an individual, as described above, in which the expression is detected and/or quantified at the RNA transcript level or messenger RNA (mRNA). The detection and/or quantification at the RNA transcript or mRNA level can be carried out by any means known to one skilled in the art. Particularly, it can be cited as examples:
 hybridization methods, preferably with a hybridization chip, by in situ hybridization or by Northern blot;
 amplification methods, preferably by RT-PCR («Reverse Transcriptase Polymerase Chain Reaction»), more preferably by RT-qPCR (quantitative RT-PCR). Mention may in particular be made of nested PCR. The PCR reactions can also be multiplexed;
 sequencing methods, preferably by high throughput sequencing Preferably, the invention relates to a method for determining the immune status of an individual, as described above, in which the immune status is determined as being an immunosuppression status (or immunodepression or immunodeficiency status or hypoactive immune status or immune paralysis), a normal immune status (or immunocompetence status), or inflammation status (or hyperactive immune status). The inflammation status includes the hyper-inflammation status.

Preferably, the invention relates to a method for determining the immune status of an individual, as described above, in which the individual is a patient admitted within a medical facility, preferably in an intensive care unit, in emergency department or in resuscitation. Also preferably, the individual is a trauma patient, a patient with burns, a surgical patient or a patient with sepsis, preferably a patient with septic shock. Even more preferably, the test biological sample is obtained by sampling made within 10 days, preferably within 9 days, preferably within 8 days, preferably within 7 days, preferably within 6 days, preferably within 5 days, preferably within 4 days, preferably within 3 days, preferably within 2 days, preferably within 24 hours, following admission to the medical facility.

Preferentially, the invention relates to a method for determining the immune status of an individual, as described above, in which the reference biological sample is a biological sample obtained from a healthy individual, preferably a biological sample obtained from the same individual from which the test biological sample was obtained but collected before infection or aggression, or a biological sample from an individual of known immune status, preferably with inflammation status, normal immune status, or an immunosuppression status.

Preferably, the test biological sample and/or the reference biological sample, as used in the method for determining the immune status of an individual, according to the invention, as described above, is a blood sample, preferably a sample of whole blood, plasma or serum, or a sample of peripheral blood mononuclear cells, extracted from a blood sample.

Preferably, the method for determining the immune status according to the invention, as described above, comprises a step of administering a treatment, preferably an immunomodulatory treatment, adapted to the immune status of the individual. Preferably, the immunomodulatory treatment is an immunostimulatory treatment, if it is determined that the individual has an immunosuppression status, or an anti-inflammatory treatment, if it is determined that the individual has an inflammatory status. Among the immunostimulant treatments which can be selected, mention may be made, by way of example, of the group of interleukins, in particular IL-7, IL-15 or IL-3, growth factors, in particular GM-CSF, interferons, in particular IFNγ, Toll agonists, antibodies, in particular anti-PD1, anti-PDL1, anti-LAG3, anti-TIM3, anti-IL-10 or anti-CTLA4 antibodies, transferrins and inhibitory molecules of apoptosis, FLT3L, Thymosin a1, adrenergic antagonists. Among the anti-inflammatory treatments, mention may in particular be made of the group of glucocorticoids, cytostatic agents, molecules acting on immunophilins and cytokines, molecules which block the IL-1 receptor and anti-TNF treatments.

The present invention also relates to the use of at least one, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34 sequence(s) selected from the sequences identified in SEQ ID NO: 1 to 34, as appearing in Lists 1 to 4, or from the sequences which exhibit at least 99% identity with one of the sequences identified in SEQ ID NO: 1 to 34, to determine in vitro or ex vivo the immune status of an individual, preferably a patient.

The present invention also relates to a method for identifying or selecting a treatment, preferably an immunomodulatory treatment, more particularly an immunostimulating treatment or an anti-inflammatory treatment, suitable for treating an individual, preferably a patient, comprising the following steps of:
 a. determining the immune status of said individual by a method as previously described
 b. identifying an appropriate treatment from the immune status determined in step a)

Preferably, the immunomodulatory treatment is an immunostimulatory treatment, if it is determined that the individual has an immunosuppression status, or an anti-inflammatory treatment, if it is determined that the individual has an inflammation status.

The present invention further relates to a method for evaluating the effectiveness of a treatment, preferably an immunomodulatory treatment, more particularly an immunostimulating treatment or an anti-inflammatory treatment, on an individual, preferably a patient, comprising the following steps of:
  a. detecting and/or quantifying the expression of at least part of a sequence selected from the sequences identified in SEQ ID NO: 1 to 34 or from the sequences which exhibit at least 99% identity with one of the identified sequences in SEQ ID NO: 1 to 34, in a first biological sample of said individual, collected before the treatment, and in a second biological sample of said individual, collected after the treatment
  b. comparing the expression obtained for the 2 biological samples in step a)
  c. evaluating the effectiveness of the treatment from the comparison of step b)

Another subject of the present invention concerns an amplification primer comprising, or consisting of, a nucleotide sequence complementary to at least part of a sequence selected from the sequences identified in SEQ ID NO: 1 to 34 or from the sequences which exhibit at least 99% identity with one of the sequences identified in SEQ ID NO: 1 to 34, and the sequences complementary to these sequences. Preferably, the amplification primer according to the invention is selected from the primers presented in Table 6.

TABLE 6

| SEQ ID NO: | Primer # | Nucleotide sequence |
|---|---|---|
| 35 | 1A | TGTACAAAACTCAAATGGTCTTC |
| 36 | 1B | ATGACCAACTTAGATTTCCTTGA |
| 37 | 2A | GCCAGAGAGGCATAATGAAGCA |
| 38 | 2B | GATTCTAAGCCTCCCCCTCATTT |
| 39 | 3A | TGGCTCATAGGGATTCCAGACT |
| 40 | 3B | AGCAAGTTGTCAAGAGCCAATCT |
| 41 | 4A | CACTCTAGGAATCTTAGGCA |
| 42 | 4B | TGAAACCAATAGTCCAGTG |
| 43 | 5A | TTCTACTGTTCACTGCTATCCTCC |
| 44 | 5B | CCTGTGGCAGCTTTTTGAAGTAA |
| 45 | 6A | AGAGCAGAAGAAGATGGATACT |
| 46 | 6B | CATGAGCTGACATCATCCAAT |
| 47 | 7A | TCTGTACTGGTTGCCCCAAC |
| 48 | 7B | CGTGCCAGGCCTCTAATACTTTT |
| 49 | 8A | AGGGAAGACCCCAAGATGATG |
| 50 | 8B | CATGCAAAGTCCAACGAGAGG |
| 51 | 9A | GGGTGGCTGCATCCTATGG |
| 52 | 9B | CTGGTCAGGAAAAAATTTGCCTTC |
| 53 | 10A | ACATGACATTGTCTGAACTTTGGG |

TABLE 6-continued

| SEQ ID NO: | Primer # | Nucleotide sequence |
|---|---|---|
| 54 | 10B | TAGGACCATGCAGATACTAGTGAC |
| 55 | 11A | GAACTCCACAAACCTTGA |
| 56 | 11B | GCTAGAAGCTTTGGATATCT |
| 57 | 12A | TGGCTGTTACAACTTTCATG |
| 58 | 12B | TCTCCCTATTCTGAGCACA |

The present invention also concerns a pair of amplification primers, consisting of two amplification primers selected from the primers as described above, and making it possible to amplify, preferably making it possible to specifically amplify, at least part of a sequence selected from the sequences identified in SEQ ID NO: 1 to 34 or from the sequences which exhibit at least 99% identity with one of the sequences identified in SEQ ID NO: 1 to 34, and the sequences complementary to these sequences. Preferably, the pair of amplification primers according to the invention is selected from the pairs of primers presented in Table 7.

TABLE 7

| Pair of Primers # | Primers # |
|---|---|
| 1 | Forward: Primer #1A |
|   | Reverse: Primer #1B |
| 2 | Forward: Primer #2A |
|   | Reverse: Primer #2B |
| 3 | Forward: Primer #3A |
|   | Reverse: Primer #3B |
| 4 | Forward: Primer #4A |
|   | Reverse: Primer #4B |
| 5 | Forward: Primer #5A |
|   | Reverse: Primer #5B |
| 6 | Forward: Primer #6A |
|   | Reverse: Primer #6B |
| 7 | Forward: Primer #7A |
|   | Reverse: Primer #7B |
| 8 | Forward: Primer #8A |
|   | Reverse: Primer #8B |
| 9 | Forward: Primer #9A |
|   | Reverse: Primer #9B |
| 10 | Forward: Primer #10A |
|   | Reverse: Primer #10B |
| 11 | Forward: Primer #11A |
|   | Reverse: Primer #11B |
| 12 | Forward: Primer #12A |
|   | Reverse: Primer #12B |

Another subject of the present invention concerns a hybridization probe, whose nucleotide sequence comprises, or consists of, a nucleotide sequence complementary to at least part of a sequence selected from the sequences identified in SEQ ID NO: 1 to 34 or from the sequences which have at least 99% identity with one of the sequences identified in SEQ ID NO: 1 to 34, and the sequences complementary to these sequences. Preferably, the hybridization probe according to the invention is selected from the hybridization probes presented in Table 8.

TABLE 8

| SEQ ID NO: | Probe # | HERV-V3 chip probe name | Nucleotide sequence |
|---|---|---|---|
| 59 | 1A | 190665001-HERV0376uL_at1 | ATGACCAACTTAGATTTCCTTGAGT |
| 60 | 1B | 190665001-HERV0376uL_at2 | GTCAAGGGTAAAGCTGTGAAAGTTT |
| 61 | 1C | 190665001-HERV0376uL_at3 | GGAAGACCATTTGAGTTTTGTACAC |
| 62 | 1A' | 190665001-HERV0376uL_st1 | ACTCAAGGAAATCTAAGTTGGTCAT |
| 63 | 1B' | 190665001-HERV0376uL_st2 | AAACTTTCACAGCTTTACCCTTGAC |
| 64 | 1C' | 190665001-HERV0376uL_st3 | GTGTACAAAACTCAAATGGTCTTCC |
| 65 | 1D | 190665002-HERV0376uL_at1 | GAAGATATGGGCCAGAACTTGTATA |
| 66 | 1E | 190665002-HERV0376uL_at2 | CAGGACCTGAGTTAAGCCAAGAATA |
| 67 | 1F | 190665002-HERV0376uL_at3 | ACCTGAGTTAAGCCAAGAATACAGT |
| 68 | 1D' | 190665002-HERV0376uL_st1 | TATACAAGTTCTGGCCCATATCTTC |
| 69 | 1E' | 190665002-HERV0376uL_st2 | TATTCTTGGCTTAACTCAGGTCCTG |
| 70 | 1F' | 190665002-HERV0376uL_st3 | ACTGTATTCTTGGCTTAACTCAGGT |
| 71 | 2A | 220247002-HERV0797uL_at1 | GTAAGATTCTAAGCCTCCCCCTCAT |
| 72 | 2B | 220247002-HERV0797uL_at2 | GATTCTAAGCCTCCCCCTCATTTAA |
| 73 | 2C | 220247002-HERV0797uL_at3 | CTAAGCCTCCCCCTCATTTAAAGGA |
| 74 | 2A' | 220247002-HERV0797uL_st1 | ATGAGGGGGAGGCTTAGAATCTTAC |
| 75 | 2B' | 220247002-HERV0797uL_st2 | TTAAATGAGGGGGAGGCTTAGAATC |
| 76 | 2C' | 220247002-HERV0797uL_st3 | TCCTTTAAATGAGGGGGAGGCTTAG |
| 77 | 3A | 170369402HE41env_at1 | ATGGCTCATAGGGATTCCAGACTCC |
| 78 | 3B | 170369402HE41env_at2 | GGCTCATAGGGATTCCAGACTCCCA |
| 79 | 3C | 170369402HE41env_at3 | CTCATAGGGATTCCAGACTCCCATT |
| 80 | 3A' | 170369402HE41env_st1 | GGAGTCTGGAATCCCTATGAGCCAT |
| 81 | 3B' | 170369402HE41env_st2 | TGGGAGTCTGGAATCCCTATGAGCC |
| 82 | 3C' | 170369402HE41env_st3 | AATGGGAGTCTGGAATCCCTATGAG |
| 83 | 4A | 121601801-HERV0492uL_at1 | TGAAACCAATAGTCCAGTGGTGGCC |
| 84 | 4B | 121601801-HERV0492uL_at2 | TTCCAGTGATTTAGATAAAATCCCT |
| 85 | 4C | 121601801-HERV0492uL_at3 | TTTCTGCCTAAGATTCCTAGAGTGC |
| 86 | 4A' | 121601801-HERV0492uL_st1 | GGCCACCACTGGACTATTGGTTTCA |
| 87 | 4B' | 121601801-HERV0492uL_st2 | AGGGATTTTATCTAAATCACTGGAA |
| 88 | 4C' | 121601801-HERV0492uL_st3 | GCACTCTAGGAATCTTAGGCAGAAA |
| 89 | 5A | 011052702-MALR1044uL_at1 | CTGTGGCAGCTTTTTGAAGTAAGGA |
| 90 | 5B | 011052702-MALR1044uL_at2 | ATGGTTAGTGCAGAGTAAAGTTTGG |
| 91 | 5C | 011052702-MALR1044uL_at3 | AGGATAGCAGTGAACAGTAGAATGG |
| 92 | 5A' | 011052702-MALR1044uL_st1 | TCCTTACTTCAAAAAGCTGCCACAG |
| 93 | 5B' | 011052702-MALR1044uL_st2 | CCAAACTTTACTCTGCACTAACCAT |
| 94 | 5C' | 011052702-MALR1044uL_st3 | CCATTCTACTGTTCACTGCTATCCT |
| 95 | 6A | 011052202-HERV1033uL_at1 | AGATCCAACATGAGCTGACATCATC |
| 96 | 6A' | 011052202-HERV1033uL_st1 | GATGATGTCAGCTCATGTTGGATCT |

TABLE 8-continued

| SEQ ID NO: | Probe # | HERV-V3 chip probe name | Nucleotide sequence |
|---|---|---|---|
| 97 | 7A | 130360601-HERV0808cL_at1 | GAGGTTGGGGCAACCAGTACAGATT |
| 98 | 7A' | 130360601-HERV0808cL_st1 | AATCTGTACTGGTTGCCCCAACCTC |
| 99 | 8A | 141107102-MALR1019uL_at1 | CCCCAAGATGATGGACTCTGGTGAT |
| 100 | 8B | 141107102-MALR1019uL_at2 | CACTGCCATCACTTTGGGAAAGACT |
| 101 | 8C | 141107102-MALR1019uL_at3 | AAGCAGCCTCTCGTTGGACTTTGCA |
| 102 | 8A' | 141107102-MALR1019uL_st1 | ATCACCAGAGTCCATCATCTTGGGG |
| 103 | 8B' | 141107102-MALR1019uL_st2 | AGTCTTTCCCAAAGTGATGGCAGTG |
| 104 | 8C' | 141107102-MALR1019uL_st3 | TGCAAAGTCCAACGAGAGGCTGCTT |
| 105 | 9A | 021460102-HERV0599uL_at1 | GAGGGCAGTTTGGAACAGTTGGAAC |
| 106 | 9B | 021460102-HERV0599uL_at2 | TGAGAGACGATTATCTGGAAGAAGA |
| 107 | 9C | 021460102-HERV0599uL_at3 | TCACAGCTTGAGAATGTGGTAGGAG |
| 108 | 9D | 021460102-HERV0599uL_at4 | GGAATGGGGGGCATGGAATTAAAGC |
| 109 | 9A' | 021460102-HERV0599uL_st1 | GTTCCAACTGTTCCAAACTGCCCTC |
| 110 | 9B' | 021460102-HERV0599uL_st2 | TCTTCTTCCAGATAATCGTCTCTCA |
| 111 | 9C' | 021460102-HERV0599uL_st3 | CTCCTACCACATTCTCAAGCTGTGA |
| 112 | 9D' | 021460102-HERV0599uL_st4 | GCTTTAATTCCATGCCCCCCATTCC |
| 113 | 10A | 021456001-MALR1017uL_at1 | AGTCCCTAACTGTCTGCAAACCCAC |
| 114 | 10B | 021456001-MALR1017uL_at2 | ACTGTCTGCAAACCCACAATGGACC |
| 115 | 10C | 021456001-MALR1017uL_at3 | CAATGGACCTGTTGCATGTGTAAGA |
| 116 | 10A' | 021456001-MALR1017uL_st1 | GTGGGTTTGCAGACAGTTAGGGACT |
| 117 | 10B' | 021456001-MALR1017uL_st2 | GGTCCATTGTGGGTTTGCAGACAGT |
| 118 | 10C' | 021456001-MALR1017uL_st3 | TCTTACACATGCAACAGGTCCATTG |
| 119 | 11A | 050286701-HERV0513uL_at1 | CTGCATCCTATGGTGTTTCTACATG |
| 120 | 11B | 050286701-HERV0513uL_at2 | ATAATCTTTTCCGGCATGTTGGTAT |
| 121 | 11C | 050286701-HERV0513uL_at3 | TAAAGATAGTGTTTCCTATTGTGTC |
| 122 | 11A' | 050286701-HERV0513uL_st1 | CATGTAGAAACACCATAGGATGCAG |
| 123 | 11B' | 050286701-HERV0513uL_st2 | ATACCAACATGCCGGAAAAGATTAT |
| 124 | 11C' | 050286701-HERV0513uL_st3 | GACACAATAGGAAACACTATCTTTA |
| 125 | 12A | 050287402-MALR1022uL_at1 | ACAGAGACTGCAAGAGTAATGACAT |
| 126 | 12B | 050287402-MALR1022uL_at2 | TCTGAACTTTGGGAAACAATTATGT |
| 127 | 12C | 050287402-MALR1022uL_at3 | ACTTTCCAGTTAATCGAATCAATCC |
| 128 | 12D | 050287402-MALR1022uL_at4 | TTTTAACCTAGACTAGTTCCAACTG |
| 129 | 12E | 050287402-MALR1022uL_at5 | GTCACTAGTATCTGCATGGTCCTAA |
| 130 | 12A' | 050287402-MALR1022uL_st1 | ATGTCATTACTCTTGCAGTCTCTGT |
| 131 | 12B' | 050287402-MALR1022uL_st2 | ACATAATTGTTTCCCAAAGTTCAGA |
| 132 | 12C' | 050287402-MALR1022uL_st3 | GGATTGATTCGATTAACTGGAAAGT |
| 133 | 12D' | 050287402-MALR1022uL_st4 | CAGTTGGAACTAGTCTAGGTTAAAA |
| 134 | 12E' | 050287402-MALR1022uL_st5 | TTAGGACCATGCAGATACTAGTGAC |

TABLE 8-continued

| SEQ ID NO: | Probe # | HERV-V3 chip probe name | Nucleotide sequence |
|---|---|---|---|
| 135 | 13A | 052182701-MALR1129uL_at1 | TTATTCCAGTCACCTCGAGTCATTC |
| 136 | 13B | 052182701-MALR1129uL_at2 | TCATCCTAGCCGTCGTAGAGCAGAG |
| 137 | 13C | 052182701-MALR1129uL_at3 | TGCCCTTCTGACTCCTTGACAGTGG |
| 138 | 13A' | 052182701-MALR1129uL_st1 | GAATGACTCGAGGTGACTGGAATAA |
| 139 | 13B' | 052182701-MALR1129uL_st2 | CTCTGCTCTACGACGGCTAGGATGA |
| 140 | 13C' | 052182701-MALR1129uL_st3 | CCACTGTCAAGGAGTCAGAAGGGCA |
| 141 | 14A | 190478501-MALR1003cL_at1 | TAAGTGGGACCAAGACACAAACCAA |
| 142 | 14B | 190478501-MALR1003cL_at3 | ACCAAGACACAAACCAACATGCCTG |
| 143 | 14A' | 190478501-MALR1003cL_st1 | TTGGTTTGTGTCTTGGTCCCACTTA |
| 144 | 14B' | 190478501-MALR1003cL_st3 | CAGGCATGTTGGTTTGTGTCTTGGT |
| 145 | 15A | 011790601ERV9sLU5p_at1 | CTGAGGTCCATGGCTTCTTTCCTTG |
| 146 | 15A' | 011790601ERV9sLU5p_st1 | CAAGGAAAGAAGCCATGGACCTCAG |
| 147 | 16A | 052681601-MALR1018uL_at1 | CCTTTGTTTTCCTACTGACAGGTCC |
| 148 | 16B | 052681601-MALR1018uL_at2 | TTCAAAATATTTAACTCTCCAGGCT |
| 149 | 16C | 052681601-MALR1018uL_at3 | GAGGTCACATGACTCTGTTGTGGAC |
| 150 | 16A' | 052681601-MALR1018uL_st1 | GGACCTGTCAGTAGGAAAACAAAGG |
| 151 | 16B' | 052681601-MALR1018uL_st2 | AGCCTGGAGAGTTAAATATTTTGAA |
| 152 | 16C' | 052681601-MALR1018uL_st3 | GTCCACAACAGAGTCATGTGACCTC |
| 153 | 17A | 160627301-MALR1014uL_at1 | CAGCTGAGATCCGTTGACGCCAGCC |
| 154 | 17B | 160627301-MALR1014uL_at2 | TCCGACATGTGGGTGAACTCAGCCA |
| 155 | 17C | 160627301-MALR1014uL_at3 | TTCTCAGCCATGTGTTTTGTGAACT |
| 156 | 17A' | 160627301-MALR1014uL_st1 | GGCTGGCGTCAACGGATCTCAGCTG |
| 157 | 17B' | 160627301-MALR1014uL_st2 | TGGCTGAGTTCACCCACATGTCGGA |
| 158 | 17C' | 160627301-MALR1014uL_st3 | AGTTCACAAAACACATGGCTGAGAA |
| 159 | 18A | 111686702-HERV0861uL_at1 | TTGAGGCAGGACAGAACCAGGCTCC |
| 160 | 18B | 111686702-HERV0861uL_at2 | GGACAGAACCAGGCTCCTGTTAGTC |
| 161 | 18C | 111686702-HERV0861uL_at3 | AGTTTACTGAGCAGTGACTTTGTGT |
| 162 | 18A' | 111686702-HERV0861uL_st1 | GGAGCCTGGTTCTGTCCTGCCTCAA |
| 163 | 18B' | 111686702-HERV0861uL_st2 | GACTAACAGGAGCCTGGTTCTGTCC |
| 164 | 18C' | 111686702-HERV0861uL_st3 | ACACAAAGTCACTGCTCAGTAAACT |
| 165 | 19A | 040318302-MALR1134uL_at1 | ATAGGGATGATCCTGCACGAATGGC |
| 166 | 19B | 040318302-MALR1134uL_at2 | GGATGATCCTGCACGAATGGCATGG |
| 167 | 19A' | 040318302-MALR1134uL_st1 | GCCATTCGTGCAGGATCATCCCTAT |
| 168 | 19B' | 040318302-MALR1134uL_st2 | CCATGCCATTCGTGCAGGATCATCC |
| 169 | 20A | 041529101-MALR1026uL_at1 | AGTGGACACTTTTAGGATGTCTGC |
| 170 | 20B | 041529101-MALR1026uL_at2 | GCCCTGACATAAGAGTTTGCCAGTT |
| 171 | 20C | 041529101-MALR1026uL_at3 | CCTGTACCCACCTTTCACCAGAGCT |
| 172 | 20A' | 041529101-MALR1026uL_st1 | GCAGACATCCTAAAAGTGTCCACT |

TABLE 8-continued

| SEQ ID NO: | Probe # | HERV-V3 chip probe name | Nucleotide sequence |
|---|---|---|---|
| 173 | 20B' | 041529101-MALR1026uL_st2 | AACTGGCAAACTCTTATGTCAGGGC |
| 174 | 20C' | 041529101-MALR1026uL_st3 | AGCTCTGGTGAAAGGTGGGTACAGG |
| 175 | 21A | 141106902-MALR1133uL_at1 | AATTGTTGGAATTTGAAAGTGGGGT |
| 176 | 21A' | 141106902-MALR1133uL_st1 | ACCCCACTTTCAAATTCCAACAATT |
| 177 | 22A | 060281701-MALR1043uL_at1 | GTCAGCACCGTGCTTCTCTAACTTT |
| 178 | 22B | 060281701-MALR1043uL_at2 | GCACCGTGCTTCTCTAACTTTCCAC |
| 179 | 22C | 060281701-MALR1043uL_at3 | CGTGCTTCTCTAACTTTCCACCTGC |
| 180 | 22A' | 060281701-MALR1043uL_st1 | AAAGTTAGAGAAGCACGGTGCTGAC |
| 181 | 22B' | 060281701-MALR1043uL_st2 | GTGGAAAGTTAGAGAAGCACGGTGC |
| 182 | 22C' | 060281701-MALR1043uL_st3 | GCAGGTGGAAAGTTAGAGAAGCACG |
| 183 | 23A | 043166601-MALR1018uL_at1 | CAGCCTCGCACCTAAGAACGCCGTG |
| 184 | 23B | 043166601-MALR1018uL_at2 | CAGTGAGAAATCTGCTGGGGATGCC |
| 185 | 23C | 043166601-MALR1018uL_at3 | GAAAGGGACATACCTGGCAGGTGCC |
| 186 | 23A' | 043166601-MALR1018uL_st1 | CACGGCGTTCTTAGGTGCGAGGCTG |
| 187 | 23B' | 043166601-MALR1018uL_st2 | GGCATCCCCAGCAGATTTCTCACTG |
| 188 | 23C' | 043166601-MALR1018uL_st3 | GGCACCTGCCAGGTATGTCCCTTTC |
| 189 | 24A | 100090601-HERV0429uL_at1 | GGTAGAGACCGAGGCGGATATACAG |
| 190 | 24B | 100090601-HERV0429uL_at3 | GAGACCGAGGCGGATATACAGGCCT |
| 191 | 24A' | 100090601-HERV0429uL_st1 | CTGTATATCCGCCTCGGTCTCTACC |
| 192 | 24B' | 100090601-HERV0429uL_st3 | AGGCCTGTATATCCGCCTCGGTCTC |
| 193 | 25A | 061529601-HERV0492uL_at1 | TATACTGGGGCCCAATTCTACAGAC |
| 194 | 25B | 061529601-HERV0492uL_at2 | CAGACATTACTTCTTTGCCAGTTGG |
| 195 | 25C | 061529601-HERV0492uL_at3 | GACACATTGCAAGTCTGGAAGAGGA |
| 196 | 25A' | 061529601-HERV0492uL_st1 | GTCTGTAGAATTGGGCCCCAGTATA |
| 197 | 25B' | 061529601-HERV0492uL_st2 | CCAACTGGCAAAGAAGTAATGTCTG |
| 198 | 25C' | 061529601-HERV0492uL_st3 | TCCTCTTCCAGACTTGCAATGTGTC |
| 199 | 26A | 100871501-MALR1020cL_at1 | CATGATCCTGGGTGAAGCCATGTGT |
| 200 | 26B | 100871501-MALR1020cL_at2 | TGTGTCTGAGGATGAAAGGGGATGC |
| 201 | 26C | 100871501-MALR1020cL_at3 | CAGATTGATGTGACATGTGGCACCT |
| 202 | 26A' | 100871501-MALR1020cL_st1 | ACACATGGCTTCACCCAGGATCATG |
| 203 | 26B' | 100871501-MALR1020cL_st2 | GCATCCCCTTTCATCCTCAGACACA |
| 204 | 26C' | 100871501-MALR1020cL_st3 | AGGTGCCACATGTCACATCAATCTG |
| 205 | 27A | 170842002-MALR1003uL_at1 | AGAGGGAGCACGGTCCCAGTACACC |
| 206 | 27B | 170842002-MALR1003uL_at2 | CACGGTCCCAGTACACCTTGAGTGT |
| 207 | 27C | 170842002-MALR1003uL_at3 | TGTTACGGCTGTCCCAGGAAAGGAA |
| 208 | 27A' | 170842002-MALR1003uL_st1 | GGTGTACTGGGACCGTGCTCCCTCT |
| 209 | 27B' | 170842002-MALR1003uL_st2 | ACACTCAAGGTGTACTGGGACCGTG |
| 210 | 27C' | 170842002-MALR1003uL_st3 | TTCCTTTCCTGGGACAGCCGTAACA |

TABLE 8-continued

| SEQ ID NO: | Probe # | HERV-V3 chip probe name | Nucleotide sequence |
|---|---|---|---|
| 211 | 28A | 081921103-HERV0958ul_at1 | ACTAAGAGCAACAGCCTGAGGCTAA |
| 212 | 28B | 081921103-HERV0958ul_at2 | GGCTCACCGGAAACAGGCTGAATGT |
| 213 | 28C | 081921103-HERV0958ul_at3 | GAGACACCAGATGACCGCTTGGTCT |
| 214 | 28D | 081921103-HERV0958ul_at4 | CAGCTTCCCTAGAATTATACACCAG |
| 215 | 28E | 081921103-HERV0958ul_at5 | TACTGAAGAGGTTACTTCAACTTGC |
| 216 | 28F | 081921103-HERV0958ul_at6 | TTGTAAAAATATAAACGTGAGGCAA |
| 217 | 28A' | 081921103-HERV0958ul_st1 | TTAGCCTCAGGCTGTTGCTCTTAGT |
| 218 | 28B' | 081921103-HERV0958ul_st2 | ACATTCAGCCTGTTTCCGGTGAGCC |
| 219 | 28C' | 081921103-HERV0958ul_st3 | AGACCAAGCGGTCATCTGGTGTCTC |
| 220 | 28D' | 081921103-HERV0958ul_st4 | CTGGTGTATAATTCTAGGGAAGCTG |
| 221 | 28E' | 081921103-HERV0958ul_st5 | GCAAGTTGAAGTAACCTGTTCAGTA |
| 222 | 28F' | 081921103-HERV0958ul_st6 | TTGCCTCACGTTTATATTTTTACAA |
| 223 | 28G | 081921101-HERV0958ul_at1 | GATGACAGTTAAGACCCTAGGTTGC |
| 224 | 28H | 081921101-HERV0958ul_at2 | CAATCTCAAGTCTGATGACTTGTTA |
| 225 | 28I | 081921101-HERV0958ul_at3 | AGACCCATCATTGCTAGCAGACTAT |
| 226 | 28J | 081921101-HERV0958ul_at4 | AAGGATGGGAAATGCTCAGGTCACG |
| 227 | 28K | 081921101-HERV0958ul_at5 | AGGGCTCATCCACTAACCCCCTGAA |
| 228 | 28L | 081921101-HERV0958ul_at6 | GAAATGGATACCCTTGGGTTCAACT |
| 229 | 28G' | 081921101-HERV0958ul_st1 | GCAACCTAGGGTCTTAACTGTCATC |
| 230 | 28H' | 081921101-HERV0958ul_st2 | TAACAAGTCATCAGACTTGAGATTG |
| 231 | 28I' | 081921101-HERV0958ul_st3 | ATAGTCTGCTAGCAATGATGGGTCT |
| 232 | 28J' | 081921101-HERV0958ul_st4 | CGTGACCTGAGCATTTCCCATCCTT |
| 233 | 28K' | 081921101-HERV0958ul_st5 | TTCAGGGGGTTAGTGGATGAGCCCT |
| 234 | 28L' | 081921101-HERV0958ul_st6 | AGTTGAACCCAAGGGTATCCATTTC |
| 235 | 28M | 081921102-HERV0958ul_at1 | GTGCCATAACGACAATTAAATTTTT |
| 236 | 28N | 081921102-HERV0958ul_at2 | AGTCTTTTGTTATCTATGGAGGACT |
| 237 | 28O | 081921102-HERV0958ul_at3 | GTTGTGTTAAAGTTTCTAATTACG |
| 238 | 28P | 081921102-HERV0958ul_at4 | GTAACTTTGGGACCAAAACAATGAA |
| 239 | 28Q | 081921102-HERV0958ul_at5 | TCATAAGCCTACTAATCCGGGATCA |
| 240 | 28R | 081921102-HERV0958ul_at6 | GGGACAAGAACTAATTCCACAGGAG |
| 241 | 28M' | 081921102-HERV0958ul_st1 | AAAAATTTAATTGTCGTTATGGCAC |
| 242 | 28N' | 081921102-HERV0958ul_st2 | AGTCCTCCATAGATAACAAAAGACT |
| 243 | 28O' | 081921102-HERV0958ul_st3 | ACGTAATTAGAAACTTTAACACAAC |
| 244 | 28P' | 081921102-HERV0958ul_st4 | TTCATTGTTTTGGTCCCAAAGTTAC |
| 245 | 28Q' | 081921102-HERV0958ul_st5 | TGATCCCGGATTAGTAGGCTTATGA |
| 246 | 28R' | 081921102-HERV0958ul_st6 | CTCCTGTGGAATTAGTTCTTGTCCC |
| 247 | 29A | 032622601MR41sLU5p_at1 | GCCCTTTCTTGAGGTCTGGGTCTGC |
| 248 | 29A' | 032622601MR41sLU5p_st1 | GCAGACCCAGACCTCAAGAAAGGGC |

TABLE 8-continued

| SEQ ID NO: | Probe # | HERV-V3 chip probe name | Nucleotide sequence |
|---|---|---|---|
| 249 | 30A | 220246901-HERV0889uL_at1 | AGGCTGTAACCCCCCTTAAACTGCC |
| 250 | 30B | 220246901-HERV0889uL_at2 | CAACTATGGGGAACTTAACTGGAGT |
| 251 | 30C | 220246901-HERV0889uL_at3 | GGAGTCGTTTCAGATGGGTGCTTAC |
| 252 | 30A' | 220246901-HERV0889uL_st1 | GGCAGTTTAAGGGGGGTTACAGCC |
| 253 | 30B' | 220246901-HERV0889uL_st2 | ACTCCAGTTAAGTTCCCCATAGTTG |
| 254 | 30C' | 220246901-HERV0889uL_st3 | GTAAGCACCCATCTGAAACGACTCC |
| 255 | 31A | 061827101-HERV0856uL_at1 | GAAGAGTTTCAGCCCTTCAGACAAC |
| 256 | 31B | 061827101-HERV0856uL_at2 | GATCCAGGTTTGTCACGCAAGCTGA |
| 257 | 31C | 061827101-HERV0856uL_at3 | CCGAGTGGGCACATCAAGCACAGTG |
| 258 | 31A' | 061827101-HERV0856uL_st1 | GTTGTCTGAAGGGCTGAAACTCTTC |
| 259 | 31B' | 061827101-HERV0856uL_st2 | TCAGCTTGCGTGACAAACCTGGATC |
| 260 | 31C' | 061827101-HERV0856uL_st3 | CACTGTGCTTGATGTGCCCACTCGG |
| 261 | 32A | 170828901-HERV0770cL_at1 | CACAGGTCTTGCCGAGACCCCCACG |
| 262 | 32B | 170828901-HERV0770cL_at2 | CCACGGGCTCACTGTTCAGCTCATC |
| 263 | 32C | 170828901-HERV0770cL_at3 | GCTCTGTCACAGTTTCCCACGACTT |
| 264 | 32A' | 170828901-HERV0770cL_st1 | CGTGGGGGTCTCGGCAAGACCTGTG |
| 265 | 32B' | 170828901-HERV0770cL_st2 | GATGAGCTGAACAGTGAGCCCGTGG |
| 266 | 32C' | 170828901-HERV0770cL_st3 | AAGTCGTGGGAAACTGTGACAGAGC |
| 267 | 33A | 190148802-MALR1127uL_at1 | GGCCAAATTGTGCCACCCCTCCCAA |
| 268 | 33B | 190148802-MALR1127uL_at2 | AATTCCCAGGACCTCCTAATATGGC |
| 269 | 33C | 190148802-MALR1127uL_at3 | GGTCGTTGTAGGCCCAGCACAGTGG |
| 270 | 33A' | 190148802-MALR1127uL_st1 | TTGGGAGGGGTGGCACAATTTGGCC |
| 271 | 33B' | 190148802-MALR1127uL_st2 | GCCATATTAGGAGGTCCTGGGAATT |
| 272 | 33C' | 190148802-MALR1127uL_st3 | CCACTGTGCTGGGCCTACAACGACC |
| 273 | 34A | 120093401-HERV1034uL_at1 | CCTAGCCATGAGCCAATTCCTTGCA |
| 274 | 34A' | 120093401-HERV1034uL_st1 | TGCAAGGAATTGGCTCATGGCTAGG |

Another subject of the invention is the use of at least one, preferably at least 2, preferably at least 3, preferably at least 4, preferably at least 5, preferably at least 6, preferably at least 7, preferably at least 8, preferably at least 9, preferably at least 10, preferably at least 11, preferably at least 12, preferably at least 13, preferably at least 14, preferably at least 15, preferably at least 16, preferably at least 17, preferably at least 18, preferably at least 19, preferably at least 20, preferably at least 21, preferably at least 22, preferably at least 23, preferably at least 24, preferably at least 25, preferably at least 26, preferably at least 27, preferably at least 28, preferably at least 29, preferably at least 30, preferably at least 31, preferably at least 32, preferably at least 33, preferably at least 34 pairs of primers according to the invention, as described above, and/or at least one, preferably at least 2, preferably at least 3, preferably at least 4, preferably at least 5, preferably at least 6, preferably at least 7, preferably at least 8, preferably at least 9, preferably at least 10, preferably at least 11, preferably at least 12, preferably at least 13, preferably at least 14, preferably at least 15, preferably at least 16, of preferably at least 17, preferably at least 18, preferably at least 19, preferably at least 20, preferably at least 21, preferably at least 22, preferably at least 23, preferably at least 24, preferably at least less 25, preferably at least 26, preferably at least 27, preferably at least 28, preferably at least 29, preferably at least 30, preferably at least 31, preferably at least 32, preferably at least 33, preferably at least 34 hybridization probes according to the invention, as described above, to determine in vitro or ex vivo the immune status of an individual, preferably a patient.

Another subject of the invention is a method for determining in vitro or ex vivo the immune status of an individual, as described above, in which at least one, preferably at least 2, preferably at least 3, of preferably at least 4, preferably at least 5, preferably at least 6, preferably at least 7, preferably at least 8, preferably at least 9, preferably at least 10, preferably at least 11, preferably at least 12, preferably at least 13, preferably at least 14, preferably at least 15, preferably at least 16, preferably at least 17, least 18, preferably at least 19, preferably at least 20, preferably at least 21, preferably at least 22, preferably at least 23, preferably at least 24, preferably at least 25, preferably at least 26, preferably at least 27, preferably at least 28, of preferably at least 29, preferably at least 30, preferably at least 31, preferably at least 32, preferably at least 33, preferably at least 34 pairs of primers as described above;

and/or at least one, preferably at least 2, preferably at least 3, preferably at least 4, preferably at least 5, preferably at least 6, preferably at least 7, preferably at least 8, of preferably at least 9, preferably at least 10, preferably at least 11, preferably at least 12, preferably at least 13, preferably at least 14, preferably at least 15, preferably at least 16, preferably at least 17, preferably at least 18, preferably at least 19, preferably at least 20, preferably at least 21, preferably at least 22, preferably at least 23, preferably at least 24, preferably at least 25, preferably at least 26, preferably at least 27, preferably at least 28, preferably at least 29, preferably at least 30, preferably at least 31, preferably at least 32, preferably at least 33, of preferably at least 34 hybridization probes as described above, are used.

Another subject of the invention is a kit comprising means for amplifying and/or detecting at least one, preferably at least 2, preferably at least 3, preferably at least 4, preferably at least 5, preferably at least 6, preferably at least 7, preferably at least 8, preferably at least 9, preferably at least 10, preferably at least 11, preferably at least 12, preferably at least 13, of preferably at least 14, preferably at least 15, preferably at least 16, preferably at least 17, preferably at least 18, preferably at least 19, preferably at least 20, preferably at least 21, preferably at least 22, preferably at least 23, preferably at least 24, preferably at least 25, preferably at least 26, preferably at least 27, preferably at least 28, preferably at least 29, preferably at least 30, preferably at least 31, preferably at least 32, preferably at least 33, preferably at least 34 sequences selected from the sequences identified in SEQ ID NO: 1 to 34 or from the sequences which exhibit at least 99% identity with one of the sequences identified in SEQ ID NO: 1 to 34.

Preferably, in the kit according to the invention:
the amplification means comprise, preferably consist of at least one, preferably at least 2, preferably at least 3, preferably at least 4, preferably at least 5, preferably at least 6, preferably at least 7, preferably at least 8, preferably at least 9, preferably at least 10, preferably at least 11, preferably at least 12, preferably at least 13, preferably at least 14, preferably at least 15, preferably at least 16, preferably at least 17, preferably at least 18, preferably at least 19, preferably at least 20, preferably at least 21, preferably at least 22, preferably at least 23, preferably at least at least 24, preferably at least 25, preferably at least 26, preferably at least 27, preferably at least 28, preferably at least 29, preferably at least 30, preferably at least 31, preferably at least 32, preferably at least 33, preferably at least 34 pairs of primers as described above;
and/or the detection means comprise, preferably consist of, at least one, preferably at least 2, preferably at least 3, preferably at least 4, preferably at least 5, preferably at least 6, preferably at least 7, preferably at least 8, preferably at least 9, preferably at least 10, preferably at least 11, preferably at least 12, preferably at least 13, preferably at least 14, preferably at least 15, preferably at least 16, preferably at least 17, preferably at least 18, preferably at least 19, preferably at least 20, preferably at least 21, preferably at least 22, preferably at least 23, preferably at least 24, preferably at least 25, preferably at least 26, preferably at least 27, preferably at least 28, preferably at least 29, preferably at least 30, preferably at least 31, preferably at least 32, preferably at least 33, preferably at least 34 hybridization probes such as described above.

Also preferably, the kit according to the present invention further comprises means for amplifying and/or detecting other biomarkers, particularly endogenous biomarkers (or loci), such as other HERV/MaLR and/or genes, preferably genes involved in the inflammation and/or the immunity, and/or housekeeping genes, and/or exogenous biomarkers, such as viruses. Among the genes involved in the immunity, the following genes may be mentioned in particular, of particular interest:

CD74, CX3CR1, IL-10, S100A8, S100A9, MERTK, CLEC7A, CD36, TIMP2, CCL13, PTGS2, IL-12B, IL-6, IL-1A, CCL20, MX1, OAS-1, CCL15, OAS-3, EIF2AK2, IFNγ, NEFH, MMP10, SERPINB2, THBD, STAT1, CCR4, HLA-DRB1/B3, TCF7, EOMES, BCL11B, ITGA7, IL-18R1, NLRC4, CYP1B1, HGF, IL-5RA, CCLP4, CD3G, CD40LG, CD3D, CD127, ICOS IL-1 R2, IL-1 RN, IL-18, IL-18RAP, OX40L, PD-1, PD-L1, Zonulin (HP), BTLA, C3AR1, CD154, GM-CSF, IFIH1, IL-15, MCP1, PCSK9, STAT4, LTR82B CIITA, LILRB2, CD177, ADGRE3, FLT-1, CD64, TREM-1, TNF-α, IL-1β, ALOX5, IL-17A, NFκB, TBX21, HIF1a, RORgT, OAS-2, GNLY, CTLA-4, TIM 3, CD274, IL-2, IL-7R, GATA3, CXCL10, FAS, GSN, MDC1, DYRK2, TDRD9, CNB1IP1, ZAP70 and ARL14EP.

Even more preferably, the kit according to the present invention comprises means for amplifying and/or detecting at most 100, preferably at most 90, preferably at most 80, preferably at most 70, preferably at most. plus 60, preferably at most 50, preferably at most 40, preferably at most 30, preferably at most 20, preferably at most 10 biomarkers, in total.

The present invention also concerns the use of a kit as described above, for determining in vitro or ex vivo the immune status of an individual, preferably a patient.

FIGURES

FIG. 1: HERV-V3 chip analysis pipeline. This diagram represents the different steps required to analyze data from the HERV-V3 chip.

Figure 2:
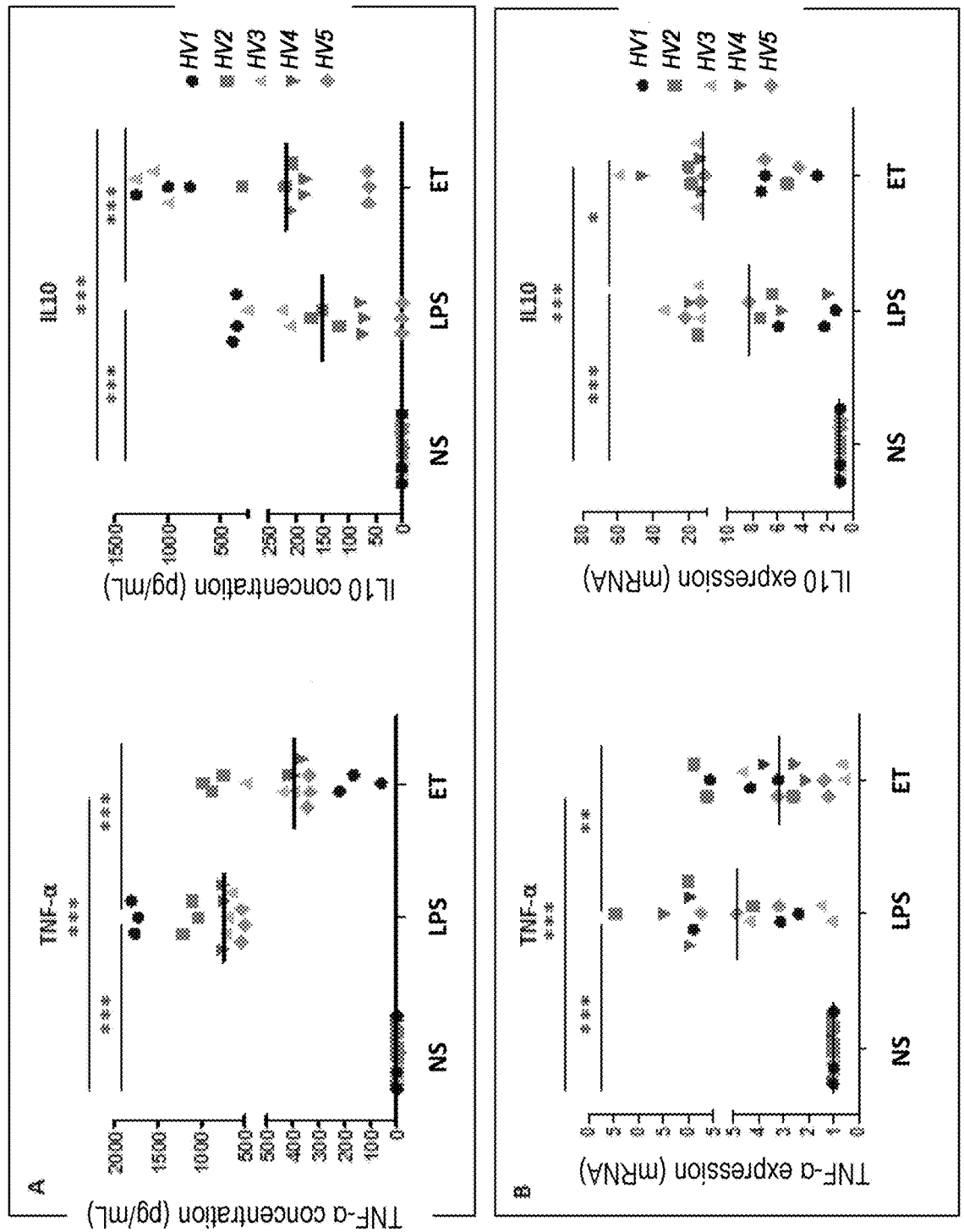

FIG. 2: FIGS. 2A and 2B respectively represent the level of expression at the protein and molecular (mRNA) levels of TNF-α and IL-10 produced by PBMCs, taken from 5 healthy volunteers, stimulated by LPS. The protein quantification was carried out by an ELISA test on culture supernatants obtained after completion of the endotoxin tolerance model. In FIG. 2A, the y-axis represents the protein concentrations (pg/mL) of TNF-α and IL-10. In FIG. 2B, the y-axis represents the expression levels of TNF-α and IL-10 (in expression ratio or Fold Change (FC)). The three conditions are represented, NS for the negative controls (without stimulation), LPS for the cells stimulated once with 100 ng/mL of LPS and ET for the cells subjected to two stimulations with LPS (2 ng/mL then 100 ng/ml). Paired Wilcoxon tests were performed for statistical analysis of the results: \*\*, means that the p-value <0.01 between 2 conditions (NS vs. LPS or NS vs. ET or LPS vs. ET). \*\*, means that the p-value <0.05 between 2 conditions. \*, means that the p-value <0.1 between 2 conditions.

Figure 3:
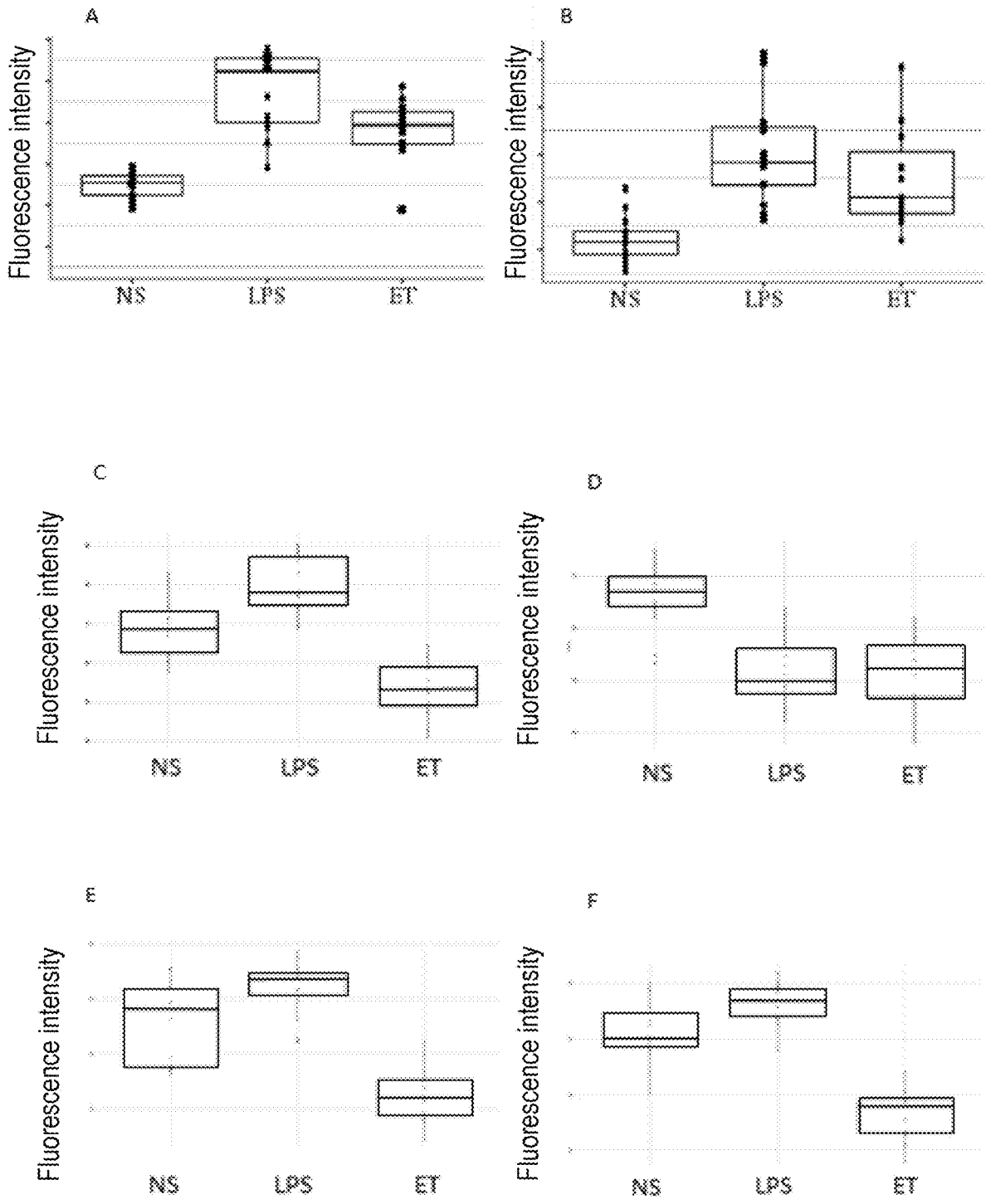

FIG. 3: FIG. 3 shows the expression of the genes of TNF-α (A) and IL-10 (B), and of the sequences SEQ ID NO: 1 (C), SEQ ID NO: 4 (D), SEQ ID NO: 5 (E) and SEQ ID NO: 6 (F), by PBMCs, taken from 5 healthy volunteers, stimulated by LPS and quantified by biochips after the completion of the endotoxin tolerance model. The y-axis represents the fluorescence intensity of each of the hybridization probes: (A) 207113_s_at for the TNF alpha, (B) 207433_at for the IL-10, (C) 190665001-HERV0376uL_at for SEQ ID NO: 1, (D) 121601801-HERV0492uL_at for SEQ ID NO: 4, (E) 011052702-MALR1044uL_at for SEQ ID NO: 5 and (F) 011052202-HERV1033uL_at for SEQ ID NO: 6. The three conditions are represented, NS for the negative controls (without stimulation), LPS for cells stimulated once with 100 ng/ml of LPS and ET for cells subjected to two stimulations with LPS (2 ng/ml then 100 ng/ml).

Figure 4:
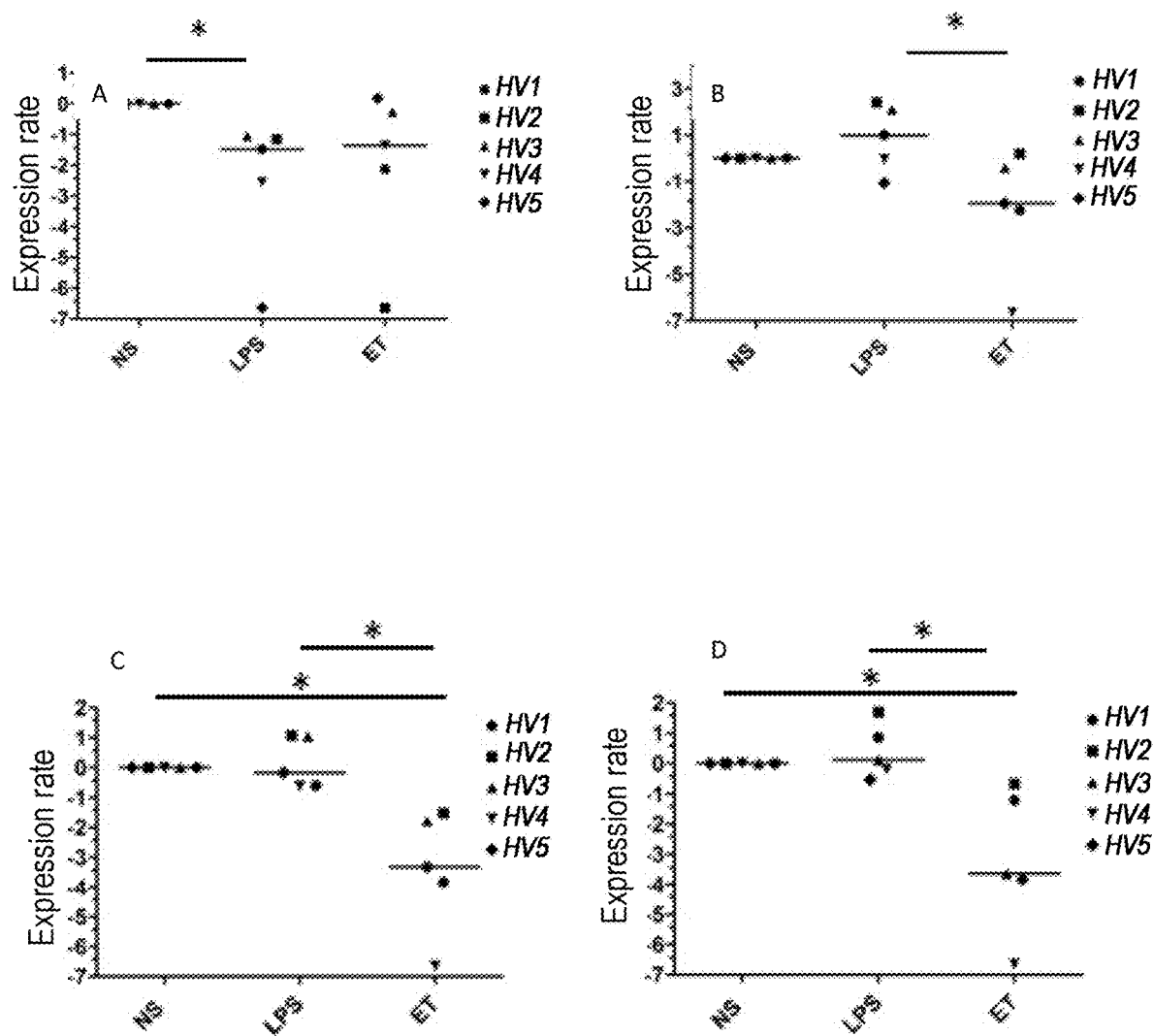

FIG. 4: FIG. 4 shows the expression of the sequences SEQ ID NO: 1 (C), SEQ ID NO: 4 (D), SEQ ID NO: 5 (E), SEQ ID NO: 6 (F), by PBMCs, taken from 5 healthy volunteers, stimulated by LPS and quantified by RT-qPCR after completion of the endotoxin tolerance model. The y-axis represents the expression rates of the sequences mentioned above. The three conditions are represented, NS for negative controls (without stimulation), LPS for cells stimulated once with 100 ng/ml of LPS and ET for cells subjected to two stimulations with LPS (2 ng/ml then 100 ng/ml). Paired Wilcoxon tests were performed for statistical analysis of the results: \*\*\*, means that the p-value <0.01 between 2 conditions (NS vs. LPS or NS vs. ET or LPS vs. ET). \*\*, means that the p-value <0.05 between 2 conditions. \*, means that the p-value <0.1 between 2 conditions.

Figure 5:
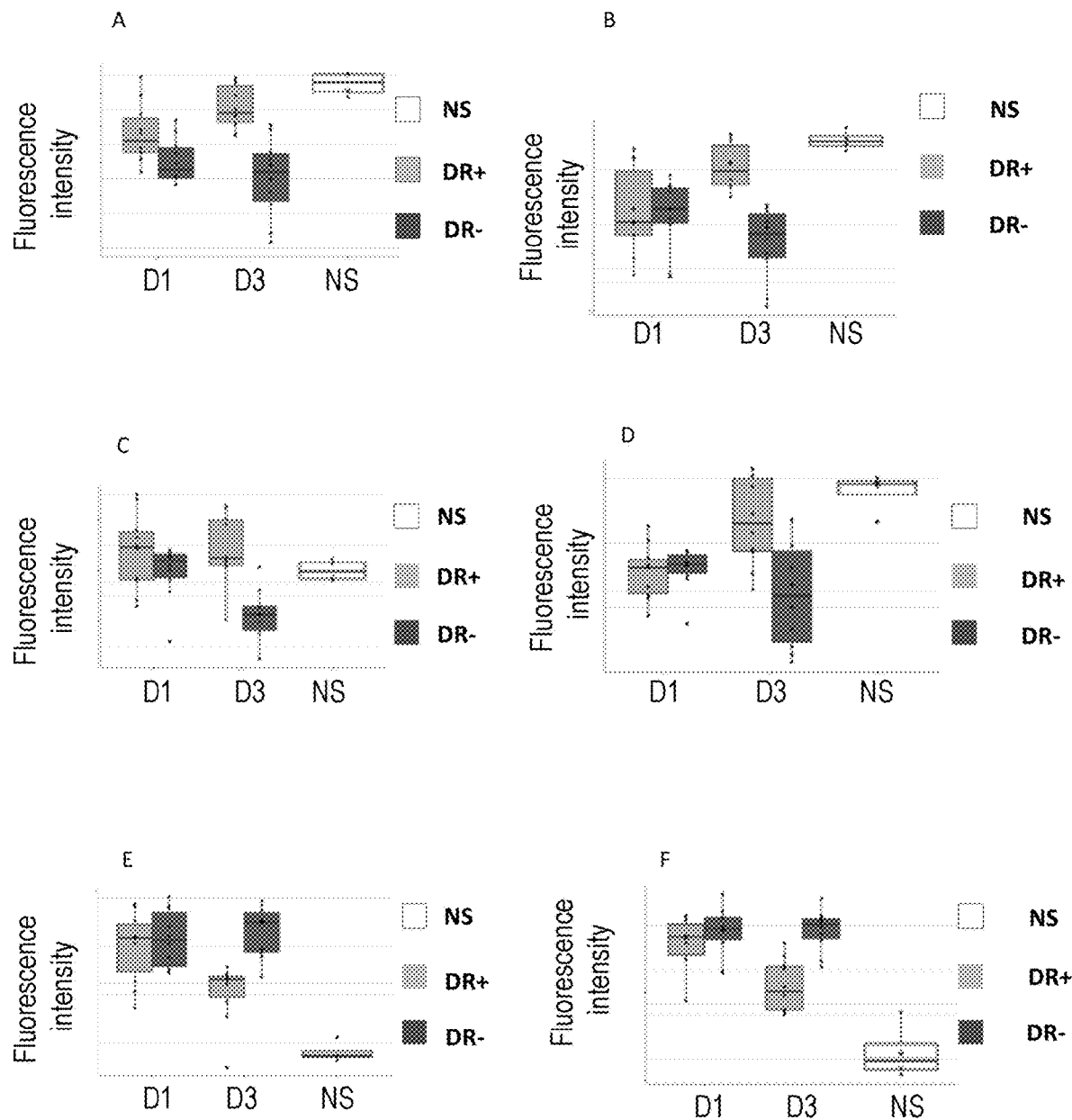

FIG. 5: FIG. 5 shows the expression of the sequences SEQ ID NO: 2 (A), SEQ ID NO: 3 (B), SEQ ID NO: 7 (C), SEQ ID NO: 8 (D), SEQ ID NO: 11 (E) and SEQ ID NO: 12 (F), from whole blood of 20 patients in septic shock stratified according to the level of expression of mHLA-DR and quantified by biochips. The y-axis represents the fluorescence intensity of each of the hybridization probes: (A) 220247002-HERV0797uL for SEQ ID NO: 2, (B) 170369402HE41env for SEQ ID NO: 3, (C) 130360601-HERV0808cL for SEQ ID NO: 7, (D) 141107102-MALR1019uL for SEQ ID NO: 8, (E) 050286701-HERV0513uL for SEQ ID NO: 11 and (F) 050287402-MALR1022uL for SEQ ID NO: 12. The three conditions are represented, HV for healthy volunteers, and on D1 and D3, DR+ for patients, having a high expression of HLA-DR, considered as immunocompetent and DR- patients, having a low expression of HLA-DR, considered as immunodepressed.

Figure 6:
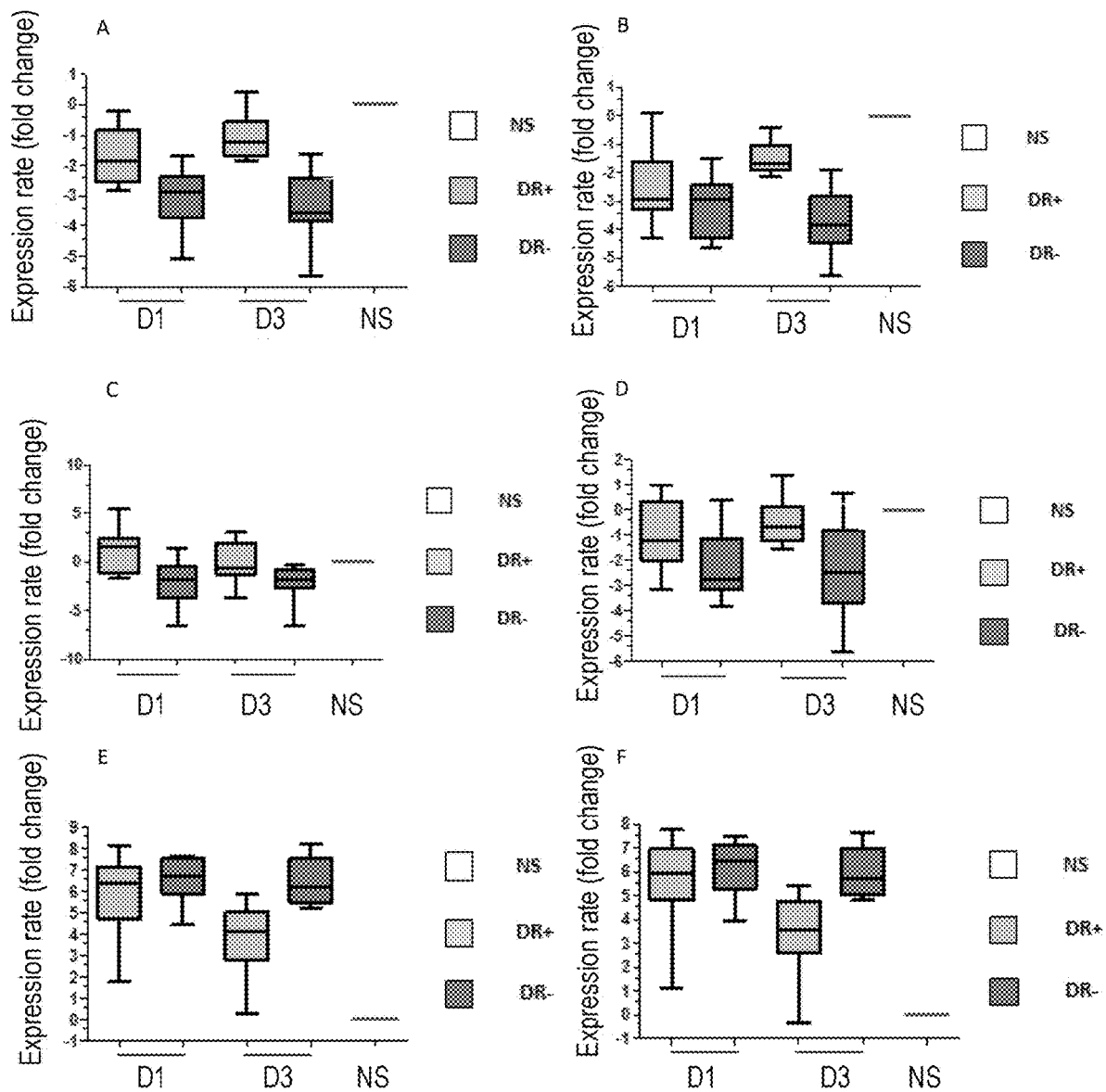

FIG. 6: FIG. 6 shows the expression of the sequences SEQ ID NO: 2 (A), SEQ ID NO: 3 (B), SEQ ID NO: 7 (C), SEQ ID NO: 8 (D), SEQ ID NO: 11 (E) and SEQ ID NO: 12 (F), from whole blood of 20 patients in septic shock stratified according to the level of expression of mHLA-DR and quantified by RT-qPCR. The y-axis represents the expression rates of the sequences mentioned above. The three conditions are represented, HV for healthy volunteers, and on D1 and D3, DR+ for patients, having a high expression of HLA-DR, considered as immunocompetent and DR- patients, having a low expression of HLA-DR, considered as immunodepressed.

Figure 7:
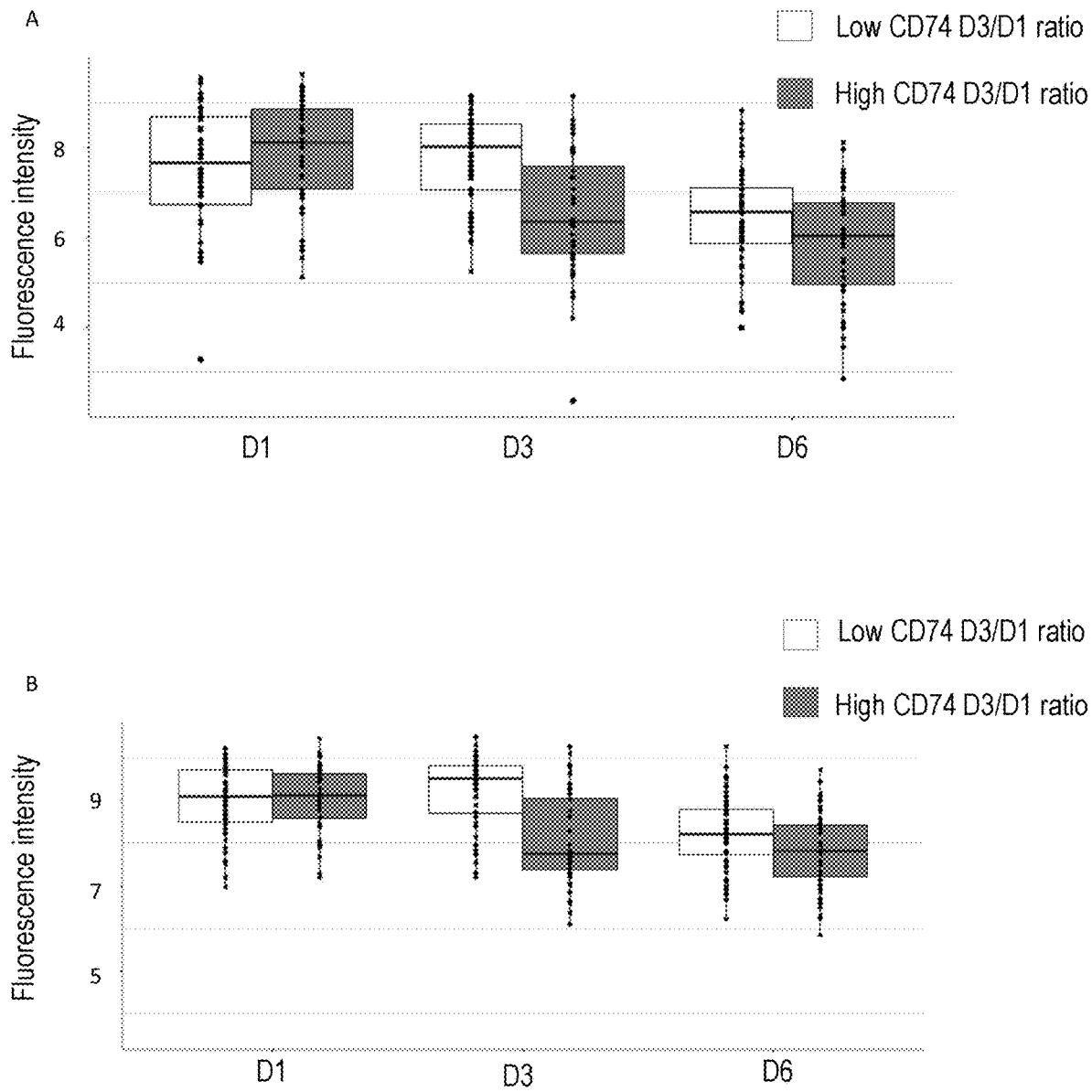

FIG. 7: FIG. 7 shows the expression of the sequences SEQ ID NO: 9 (A) and SEQ ID NO: 10 (B), from whole blood of 102 patients in septic shock stratified according to the ratio between the level of expression of CD74 on D3 and the expression level of CD74 on D1 and quantified by biochips. The y-axis represents the fluorescence intensity of each of the hybridization probes: (A) 021460102-HERV0599uL_st for SEQ ID NO: 9 and (B) 021456001-MALR1017uL_at for SEQ ID NO: 10. The following conditions are represented on D1, D3 and D6, immunocompetent patients («high» CD74 D3/D1 ratio) and immunodepressed patients («low» CD74 D3/D1 ratio).

Figure 8:
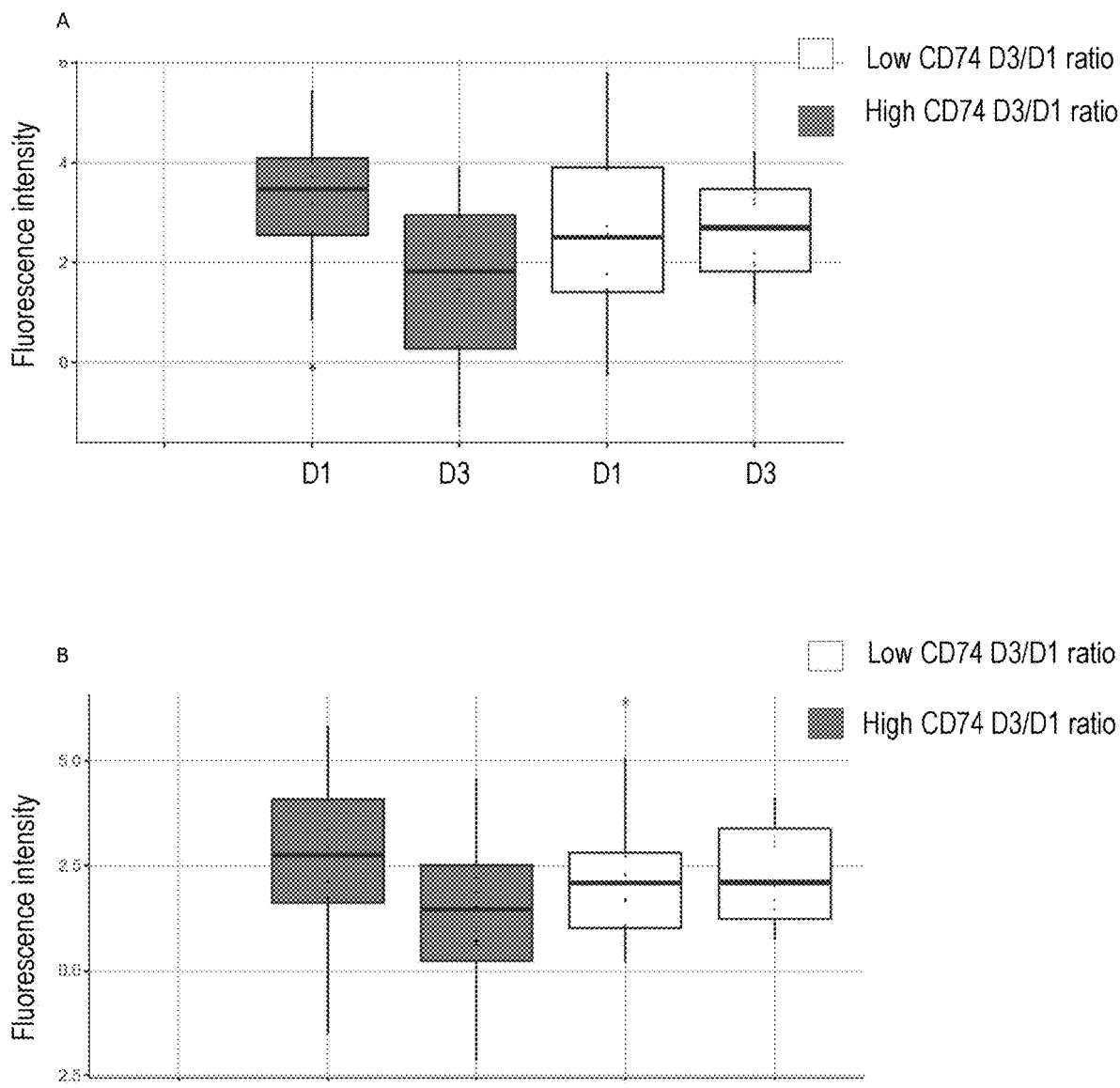

FIG. 8: FIG. 8 shows the expression of the sequences SEQ ID NO: 9 (A) and SEQ ID NO: 10 (B), from the whole blood of 102 patients in septic shock stratified as a function of the ratio between the level of expression of CD74 on D3 and the expression level of CD74 on D1 and quantified by RT-qPCR. The y-axis represents the expression rates of the sequences mentioned above. The following conditions are represented on D1, D3 and D6, immunocompetent patients («high» CD74 D3/D1 ratio) and immunodepressed patients («low» CD74 D3/D1 ratio).

Figure 9:
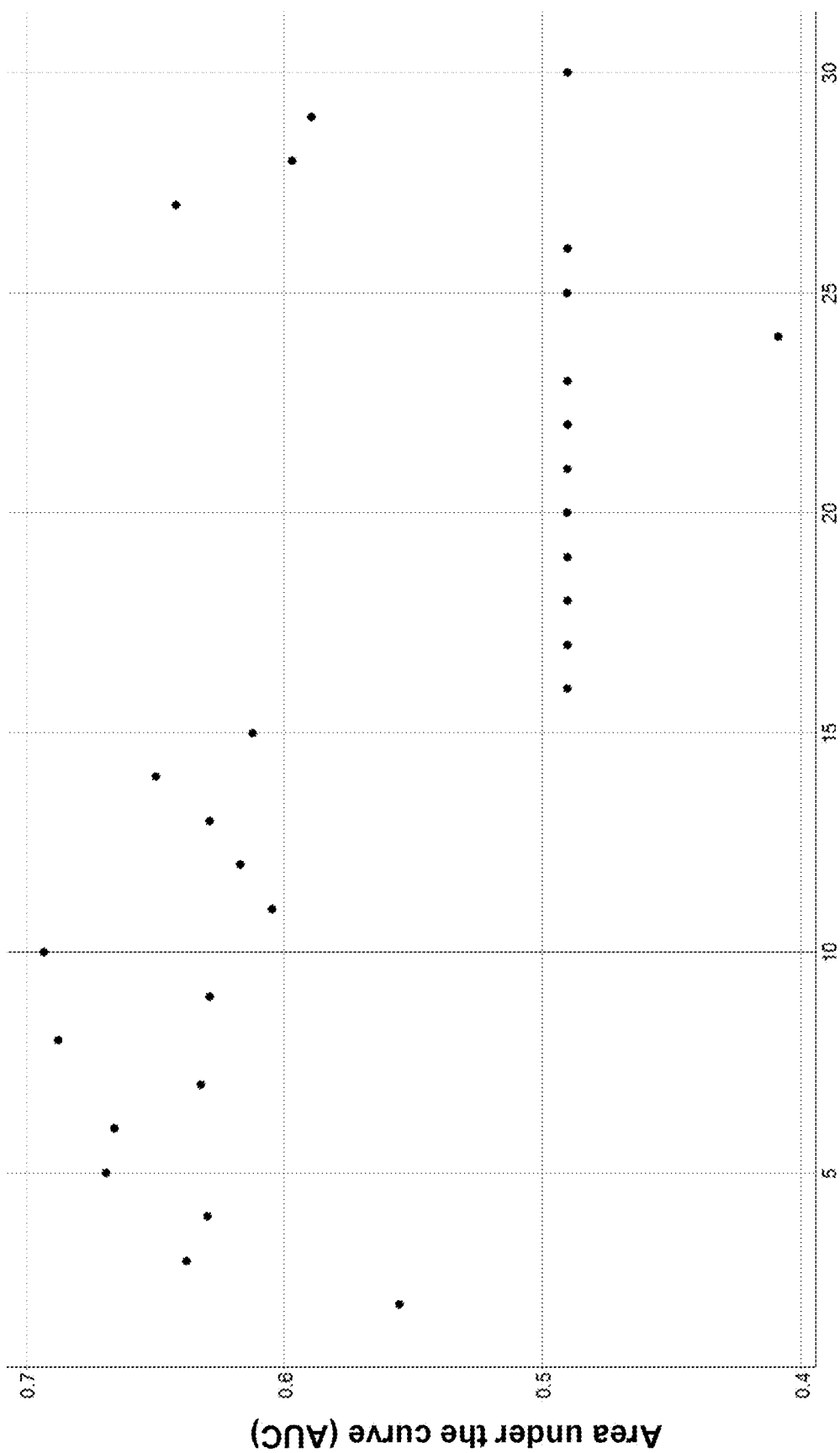

FIG. 9: FIG. 9 shows a graph representing the association between the size of the signature of markers and the discriminating power between patients considered to be immunocompetent and those considered to be immunodepressed.

The present invention is illustrated in a non-limiting manner by the following examples.

Example 1: Endotoxin Tolerance (ET) Model

The endotoxin tolerance corresponds to a temporary state of the inability of a cell or organism to respond to endotoxin stimulation, resulting from a first endotoxin stimulation.

The endotoxin tolerance model was set up to mimic on the one hand an inflammatory context induced by a stimulation by lipopolysaccharide (LPS) and on the other hand the monocytic anergy which represents a state of «no response» of the cells. These components of immunity are found in different types of patients, such as patients suffering from sepsis, trauma, burns or who have undergone major surgery.

Materials and Methods

PBMC Stimulation

The endotoxin tolerance model was established from 5 bags of citrated blood from healthy volunteers collected at the EFS in accordance with standard procedures for blood donation, and used immediately after receipt. PBMCs, peripheral blood mononuclear cells, are isolated using a density gradient adjusted to 2 million cells per mL and cultured in X-Vivo medium (Lonza) at 37° C. and 5% CO2. The endotoxin used in this model is the lipopolysaccharide (LPS), which is a major component of the outer membrane of Gram negative bacteria. The LPS is obtained from a mixture of three strains of *Escherichia coli*: O111: B4, O55: B5 and O127: B8 (Sigma). All of the conditions are carried out in biological triplicates. In this ex-vivo model of endotoxin tolerance, the PBMCs are first cultured for 15 hours without (NS control cells and LPS cells mimicking the inflammatory condition) or with a dose of 2 ng/ml of LPS (ET cells mimicking monocytic anergy, immunosuppression condition). After a washing step, the PBMCs are incubated a second time for 6 hours without (NS control cells) or with a dose of 100 ng/ml of LPS (LPS and ET cells).

At the end of the experiments, the culture supernatants are harvested and stored at −80° C. The cells are also harvested, lysed and stored at −80° C. before performing RNA extraction (Qiagen commercial kit) for the transcriptomic study. To validate the efficiency of the model, the concentrations of the pro-inflammatory cytokine TNF-α («tolerizable gene»)

and of the anti-inflammatory cytokine IL10 («non-tolerizable gene») are determined from the culture supernatants of PBMC by ELISA (commercial R&D System kits).

RNA Extraction and Amplification

The mRNAs are extracted using commercial kits (RNeasy Mini Plus kit, QIAGEN) from the ex vivo cultures of PBMCs described above.

The total mRNAs are then assayed and characterized. The characterization of the mRNA is carried out by capillary electrophoresis using the Bioanalyser 2100. The quality of the mRNA samples is evaluated by the calculation of the RIN (RNA Integrity Number). This value is based on the detection of 18S and 28S ribosomal RNAs, if the RIN tends towards 10 it means that the mRNA is intact (a RIN$\geq$7 is accepted).

The synthesis of the complementary DNA (cDNA) and the amplification steps are carried out by a linear and isothermal method described in 2005 by the company NuGEN Technologies (Kum N et al. *Novel isothermal, linear nucleic acid amplification systems for highly multiplexed applications*. Clinical chemistry. 2005; 51 (10): 1973-81). The Ribo-SPIA amplification process is used (Watson J D et al. *Complementary RNA amplification methods enhance microarray identification of transcripts expressed in the C. elegans nervous system*. BMC genomics. 2008; 9:84) from 16 ng of Total RNA (WTO pico commercial kit, Nugen) and consists of three steps. The first step is the production of the first strand of cDNA by reverse transcription from an mRNA template, this by using a mixture of random primers and oligo-dT. The second step, consists in adding DNA polymerase to the reaction, which induces the production of the second strand of cDNA. The third step, involves the SPIA amplification by strand displacement. Hybrid DNA/RNA primers are degraded by the RNAse H activity of DNA polymerase when complexed with the cDNA template. Single-stranded DNA synthesis (complementary to the mRNA template) is initiated and continues, authorizing new SPIA primers to be fixed to the cDNA template, thus sustaining the repetitive process of strand synthesis. The cDNAs are then fragmented into fragments of 50-200 bp using a DNase from 5 µg of purified and amplified DNA (commercial kit, Nugen) and are also labeled in 3' (Nugen commercial kit). The amplification and fragmentation of the cDNA are verified on the Bioanalyser. The amplification profile spans a cDNA size range from 25 to 4000 nucleotides, with a peak around 1500 pb. The fragmentation profile should be centered on a nucleic acid population around 100 nucleotides in size, which is recommended for hybridization on an Affymetrix microarray.

Analysis by Biochip

The identification of sequences exhibiting an expression differential is based on the design and the use of a high density DNA chip in GeneChip format, called HERV-V3, designed by the inventors and whose manufacture has been subcontracted to the Affymetrix company. This chip contains probes that are hybridized to distinct HERV sequences within the human genome. These sequences are extracted from a database specific to the inventors, already published (Becker et al. *A comprehensive hybridization model allows whole HERV transcriptome profiling using high density microarray*, BMC Genomics 2017 18: 286).

The HERV-V3 chip targets 353,994 HERV/MaLR elements, and over 1,500 immunity genes.

Once the cDNAs have been amplified and fragmented, they can be hybridized on the HERV-V3 chip, in an oven at 50° C. for 18 hours with constant stirring at 60 rpm for hybridization. A fluidics system allows automating the washing and coloring steps, and finally after all of these steps, the chip is read using a fluorometric scanner.

The raw dataset is created from the aggregation of the CEL files of each chip by traditional Affymetrix methods.

After a first quality control of the raw data, several steps are carried out: correcting the background noise by the Robust Multi-array Average (RMA) method, standardizing the data of each chip by quantiles, grouping the probe data into sets of probes (probes in probesets) and smoothing of the median. A second step of quality control is carried out. All these steps thus make it possible to obtain a matrix containing the normalized data.

The pre-treatment of the chips as well as the statistical analysis are carried out by using R/Bioconductor.

A pre-analysis step consists on evaluating the quality of the chips, before and after normalization. For this, several criteria must be taken into account: the quality of the RNA, the amplification and fragmentation controls of the cDNA, the image of the chips produced after the scan, the hybridization of the Affymetrix controls, the signal intensity (before and after normalization), probeset homogeneity (RLE and NUSE plots), chips correlation (before and after normalization) and principal component analysis. For all of these criteria, a statistical analysis allows identifying the extreme values for each chip and the data are then grouped together. Chips that pass less than 5 quality controls are removed from the analysis. For each data set, a decision table is then produced to summarize all the quality criteria, and quickly identify the chips to be removed from the analysis.

Sometimes it is necessary to have a corrective method for the analysis of data. This so-called COMBAT correction (for Combining BATches) makes it possible to correct the technical variability of the dataset and thus bring out its biological variability.

Finally, a data filter step was performed to reduce the data set and gain statistical power for the analyses. The intensity threshold was defined as the minimum intensity value for which the $75^{th}$ percentile of the distribution of the coefficients of variation is below 10%. In this way, the intensity threshold is $2^{5.5}$. The probesets below the intensity threshold in more than 68% of all samples (31 of 45 samples) are eliminated.

Among the 71,063 probesets targeting HERVs/MaLRs and the 42,560 probesets targeting genes selected in the previous step, a differential expression analysis was performed.

Studying the differential expression between two conditions is like calculating the expression ratio or Fold Change (FC). For example an expression value equal to under condition A, and a value equal to 5 under condition B, the FC of A/B is equal to 2. The FC data will be represented in log 2 FC. To determine that a gene or a HERV/MaLR sequence is differentially expressed between two conditions, the Limma method was used (Smyth G K. *Linear models and empirical bayes methods for assessing differential expression in microarray experiments. Statistical applications in genetics and molecular biology* 2004, 3:Article3). Statistical tests and their associated p-value are calculated to evaluate the significance of the observed expression changes. The p-values were adjusted by controlling the false discovery rate (FDR, due to multiple tests) according to the method of Benjamini and Hochberg (Hochberg et al. *Controlling the False Discovery Rate: A Practical and Powerful Approach to Multiple Testing. Journal of the Royal Statistical Society Series B (Methodological)* 1995, Vol. 57, No. 1 (1995), pp. 289-300). A probeset is considered to be significantly differentially expressed when the absolute value of FC in log 2 is greater than 1 and the fitted p-value is below 0.05 (see FIG. 1).

The sequences which were identified as being the most differentially expressed by the biochip were validated by RT-qPCR from the same samples as those which made it possible to produce the HERV-V3 chips.

Results

As indicated above, to validate the efficiency of the model, the concentrations of the pro-inflammatory cytokine TNF-α («tolerizable gene») and of the anti-inflammatory cytokine IL10 («non-tolerizable gene») are determined from the supernatants of PBMC culture by ELISA (commercial R&D System kits).

As shown in FIG. 2A, cells stimulated twice with LPS (ET model, immunosuppression condition) produce low amounts of TNF-α (100-500 pg/mL) compared to cells stimulated only once (LPS model, inflammatory condition) (500-2000 pg/mL). In contrast, these same cells secrete higher concentrations of IL-10 (100-1000 pg/mL) compared to cells stimulated once (50-400 pg/mL). These results at the protein level are confirmed at the mRNA level since a significant decrease in the expression of TNF-α coupled with an increase in the gene expression of IL-10 (FIG. 2B) in the cells stimulated twice by LPS were observed in comparison to once-stimulated PBMCs.

These results allow validating the effectiveness of this model.

An analysis of the expression of HERV/MalR and genes in unstimulated PBMC (NS, control), stimulated once with LPS (LPS, inflammatory condition) or twice stimulated with LPS (ET, immunosuppression condition) was made on the HERV-V3 biochip, designed by the inventors.

The processing of the data generated by the analysis of the HERV-V3 chips using this method made it possible to identify a set of 4 sets of probes (or «probesets»). These «probesets» are the most statistically differentially expressed among the sequences showing a statistically significant difference in expression between the different conditions (healthy patients, inflammatory condition and immunosuppression condition). As indicated previously, for the expression differential to be statistically significant, the absolute value of log 2 Fold Change must be greater than or equal to 1 and the adjusted p-value must be less than or equal to 0.05. These criteria will apply for all examples. These 4 «probesets» are associated with HERV sequences identified by SEQ ID NO: 1 and 4 to 6. The chromosomal location of each sequence is given in the GRCh38 reference. In Table 9, below, the list of identified sequences.

TABLE 9

| SEQ ID NO: | NAME OF THE PROBESETS OF THE HERV-V3 CHIP | FAMILY NAME | GRCH38 LOCATION OF THE ENTIRE ELEMENT |
|---|---|---|---|
| SEQ ID NO: 1 | 190665001-HERV0376 | LTR101 | chr19:54891074-54891496 |
| SEQ ID NO: 4 | 121601801-HERV0492 | LTR33 | chr12:112971073-112971451 |
| SEQ ID NO: 5 | 011052702-MALR1044 | MSTC | chr12:112971073-112971451 |
| SEQ ID NO: 6 | 011052202-HERV1033 | MLT2B5 | chr1:78623489-78623954 |

As observed in FIG. 3C, the expression of the sequence SEQ ID NO: 1 is statistically significantly greater under the NS condition compared to the LPS and ET conditions.

FIGS. 3D and 3F illustrate the expression profile of the sequences SEQ ID NO: 4 and SEQ ID NO: 5 observed in the PBMCs with the HERV-V3 chip. These figures show a similar expression profile, namely, for these two sequences, an increase in expression under the LPS condition compared to the NS and ET conditions, with a statistically significant difference between LPS and ET.

The sequence SEQ ID NO: 6, for its part, has greater expression under the NS and LPS conditions compared to the ET condition, with statistically significant differences between NS and ET, and between LPS and ET (FIG. 3F).

These results show a modulation of the expression of these sequences in the endotoxin tolerance model and thus their ability to be used as a marker of immune status.

The results also show that the sequences SEQ ID NO: 4 to 6 have a «tolerizable» profile (inflammatory condition) in an endotoxin tolerance model while the sequence SEQ ID NO: 1 has a «non-tolerizable» profile (immunosuppression condition) in an endotoxin tolerance model.

FIG. 3 illustrates the expression of the sequences SEQ ID NO: 1 (C), SEQ ID NO: 4 (D), SEQ ID NO: 5 (E), SEQ ID NO: 6 (F), on PBMCs, obtained from the same 5 healthy volunteers than for the HERV-V3 biochip, stimulated by LPS and quantified by RT-qPCR after completion of the endotoxin tolerance model.

The results show that the same profile as that obtained on the biochips is observed for each identified sequence. Thus, the data obtained by the HERV-V3 biochip are confirmed by RT-qPCR (FIG. 3).

Example 2: Patients in Intensive Care

Materials and Methods

Patients and Biological Samples

This retrospective observational study was conducted in patients aged 37 to 77 years (13 men, 7 women, median age: 59 years) admitted to intensive care following septic shock.

Whole blood samples were collected in PAXgene tubes (PreAnalytix) from these 20 patients in septic shock on days 1 (D1) and 3 or 4 (D3) after admission to intensive care, and were then stored (retrospective cohort).

Patients in this cohort were stratified according to the expression level of HLA-DR at the surface of monocytes (mHLA-DR). The expression of mHLA-DR was measured on D3 (days 3 or 4) by flow cytometry.

20 patients from this cohort were selected, 10 patients (50%) had high expression of HLA-DR on day 3 or 4 (more than 30% of expression), and 10 patients (50%) had a low expression of HLA-DR on day 3 or 4 (less than 30% of expression).

Patients with high expression of HLA-DR are considered to have immunocompetent status (DR+) and patients with low expression of HLA-DR are considered to have immunodepressed status (DR−).

5 healthy volunteers are also included in this study.

RNA Extraction

RNA extraction was performed using the PAXgene Blood RNA Kit (PreAnalytix) following the manufacturer recommendations. Before the RNA elution step, residual genomic DNA was removed by the action of DNAse. The RNA concentration was determined by fluorimetry (RNA assay kit on Oubit, Life Technologies). The quality of the RNA was then controlled using the RNA 6000 Nano kit on a Bioanalyzer (Agilent Technologies), the collections with a RIN (RNA Integrity Number) greater than 6 being considered to be of good quality.

The steps of RNA amplification, biochip analysis and validations of sequences by RT-qPCR which were identified as being differentially expressed by the biochip are carried out as described in Example 1.

Results

The processing of the data generated by the analysis of the HERV-V3 chips using this method made it possible to identify a set of 6 sets of probes (or «probesets»). These «probesets» are the most statistically differentially expressed among the sequences showing a statistically significant difference in expression between the two conditions (immunocompetent condition and immunosuppression condition). These 6 «probesets» are associated with HERV sequences identified by SEQ ID NO: 2, 3, 7, 8, 11 and 12. The chromosomal location of each sequence is given in the GRCh38 reference. In Table 10, below, the list of the 6 identified sequences.

TABLE 10

| SEQ ID NO: | NAME OF THE PROBESETS OF THE HERV-V3 CHIP | FAMILY NAME | GRCH38 LOCATION OF THE ENTIRE ELEMENT |
|---|---|---|---|
| SEQ ID NO: 2 | 220247002-HERV0797 | MER4B | chr22:36153696-36154283 |
| SEQ ID NO: 3 | 170369402HE41env | HERV-E4.1 | chr17:35505737-35508365 |
| SEQ ID NO: 7 | 130360601-HERV0808 | MER50C | chr13:42884951-42886257 |
| SEQ ID NO: 8 | 141107102-MALR1019 | MLT1J1 | chr14:91230494-91230820 |
| SEQ ID NO: 11 | 050286701-HERV0513 | LTR40A | chr5:14551189-14551685 |
| SEQ ID NO: 12 | 050287402-MALR1022 | MLT1K | chr5:14562791-14563322 |

As observed in FIGS. 5A and 5C, the expression of the sequences SEQ ID NO: 2 and 7 is decreased in immunodepressed patients (DR−) from D1 after admission to intensive care compared to immunocompetent patients. While the expression of SEQ ID NOs: 3, 8, 11 and 12 is decreased in immunodepressed patients (DR−) on D3 after admission to intensive care compared to immunocompetent patients (see FIGS. 5B, 5D, 5E and 5F).

Thus, these results show the usefulness of the sequences SEQ ID NO: 2 and 7 as markers, from D1, of immunosuppression. The sequences SEQ ID NO: 3, 8, 11 and 12, for their part, are markers of immunosuppression at D3.

These sequences, identified as being differentially expressed by the biochip, were validated by RT-qPCR. The results are illustrated in FIG. 6.

Profiles similar to those obtained on the biochips are observed for each identified sequence. Thus, the data obtained by the HERV-V3 biochip are confirmed by RT-qPCR.

Example 3: Patients in Resuscitation

Materials and Methods
Patients and Biological Samples

This retrospective observational study was conducted in patients admitted to resuscitation in 6 French hospitals from 2009 to 2011. The inclusion criteria were as follows:
patients aged 18 or over;
prediction by the clinician of a length of stay in intensive care of at least 2 days;
patients having at least one site of acute infection suspected or confirmed by the clinician on clinical or paraclinical manifestations;
patients having at least two of the following criteria:
temperature above 38° C. or below 36° C.;
heart rate greater than 90 beats per minute;
respiratory rate greater than 20 breaths per minute or PaCO2<32 mmHg;
number of leukocytes greater than 12000/mm3 or less than 4000/mm3.

The exclusion criteria were as follows:
pre-existing immunodepression, including recent chemotherapy or immunosuppressive treatment,
a high dose (>5 mg/kg of prednisolone equivalent for a duration>5 days) or a prolonged treatment (0.5 mg/kg of prednisolone>30 days) of corticosteroids;
aplasia (circulating neutrophils <500 cells/mm3),
primary immunodeficiency and
extracorporeal circulation the month preceding admission to the intensive care unit.

Among all patients, 102 patients met the following criteria:
patients with septic shock;
a first blood collection was taken within the first 24 hours of the patient arrival in intensive care (D1);
a second blood collection was taken between 3 and 4 days following the patient arrival in intensive care (D3);
a third blood collection was taken 6 days after the patient arrival in intensive care (D6).

Then, the patients of this cohort were stratified according to the ratio of the level of expression of CD74 on D3 to the level of expression of CD74 on D1, carried out by RT-qPCR.

The cohort was divided into 2 categories. People with a CD74 D3/D1 ratio greater than 1.23 are called «high» and are considered to have an immunocompetent status. Those with a CD74 D3/D1 ratio of less than 1.23 are called «low» and are considered to have an immunodepressed status.

Among the 102 patients in this cohort, 52 patients (51%) are considered to have an immunodepressed status («low» CD74 D3/D1 ratio) and 50 patients (49%) are considered to have an immunocompetent status («high» CD74 D3/D1 ratio).

The RNA extraction step is implemented as described in Example 2.

The steps of amplifying the RNA, analyzing by biochip and validating by RT-qPCR (on D1 and D3) the sequences which have been identified as being differentially expressed by the biochip are implemented as described in Example 1.

Results

The processing of the data generated by the analysis of the HERV-V3 chips using this method made it possible to identify a set of 2 sets of probes (or «probesets»). These «probesets» are the most statistically differentially expressed among the sequences showing a statistically significant difference in expression between the two conditions (immunocompetent condition and immunosuppression condition). These 2 «probesets» are associated with HERV sequences identified by SEQ ID NO: 9 and 10. The chromosomal location of each sequence is given in the GRCh38 reference. In Table 11, below, the 2 identified sequences.

TABLE 11

| SEQ ID NO: | NAME OF THE PROBESETS OF THE HERV-V3 CHIP | FAMILY NAME | GRCH38 LOCATION OF THE ENTIRE ELEMENT |
|---|---|---|---|
| SEQ ID NO: 9 | 021460102-HERV0599uL | LTR82B | chr2:102363654-102366601 |

TABLE 11-continued

| SEQ ID NO: | NAME OF THE PROBESETS OF THE HERV-V3 CHIP | FAMILY NAME | GRCH38 LOCATION OF THE ENTIRE ELEMENT |
|---|---|---|---|
| SEQ ID NO: 10 | 021456001-MALR1017uL | MLT11 | chr2:102013616-102013971 |

As observed in FIG. 7A, the expression of the sequence SEQ ID NO: 9 is higher on D3 in patients with a «low» CD74 D3/D1 ratio compared to patients with a «high» CD74 D3/D1 ratio.

Identically for the expression of the sequence SEQ ID NO: 10 (FIG. 7B), it is higher on D3 in patients with a «low» CD74 D3/D1 ratio compared to patients with a «high» CD74 D3/D1 ratio.

Thus, these results show the usefulness of these SEQ ID NOs: 9 and 10 sequences as a marker of the immunosuppression state on D3.

These sequences, identified as being differentially expressed by the biochip, were validated by RT-qPCR on D1 and D3 from 30 patients out of the 102 of the cohort. The results are illustrated in FIG. 8.

Profiles similar to those obtained on the biochips are observed for each identified sequence. Thus, the data obtained by the HERV-V3 biochip are confirmed by RT-qPCR from 30 patients.

Example 4: Notation of Identified Sequences

For each of the sequences identified in Examples 1 to 3 (SEQ ID NO: 1-12), the inventors have assigned a rating. This rating is based on the expression profiles, in chips, of the sequences SEQ ID NO: 1 to 12 observed on the cohort of Example 2.

The inventors have assigned ratings ranging from 1 to 4 stars. All the criteria are visual, from graphs showing the expression of the different identified sequences. As seen previously, all these sequences have already been selected on the basis of the level of expression and the differential of expression. The method of assigning ratings is described in Table 12, below.

TABLE 12

| CRITERIA | RATING |
|---|---|
| Increase of the expression in patients with low DR on D3 and visible difference from D1 | **** |
| Increase of the expression in patients with low DR on D3, difference not visible on D1 | *** |
| Decrease of the expression in patients with low DR from D1, difference visible or not at D3 | ** |
| Decrease of the expression in patients with low DR on D3, difference not visible on D1 | * |

Here in Table 13, below, the rating obtained for each of the sequences identified in Examples 1 to 3.

TABLE 13

| SEQ ID NO: | NAME OF THE PROBESETS OF THE HERV-V3 CHIP | CHROMOSOMAL LOCATION | SCORE |
|---|---|---|---|
| SEQ ID NO: 1 | 190665001-HERV0376 | chr19:54891074-54891496 | *** |
| SEQ ID NO: 2 | 220247002-HERV0797 | chr22:36153696-36154283 | ** |
| SEQ ID NO: 3 | 170369402HE41env | chr17:35505737-35508365 | * |
| SEQ ID NO: 4 | 121601801-HERV0492 | chr12:112971073-112971451 | ** |
| SEQ ID NO: 5 | 011052702-MALR1044 | chr1:78648318-78648697 | ** |
| SEQ ID NO: 6 | 011052202-HERV1033 | chr1:78623489-78623954 | ** |
| SEQ ID NO: 7 | 130360601-HERV0808 | chr13:42884951-42886257 | *** |
| SEQ ID NO: 8 | 141107102-MALR1019 | chr14:91230494-91230820 | * |
| SEQ ID NO: 9 | 021460102-HERV0599 | chr2:102363654-102366601 | *** |
| SEQ ID NO: 10 | 021456001-MALR1017 | chr2:102013616-102013971 | *** |
| SEQ ID NO: 11 | 050286701-HERV0513 | chr5:14551189-14551685 | **** |
| SEQ ID NO: 12 | 050287402-MALR1022 | chr5:14562791-14563322 | **** |

Example 5: HERV Markers of the Immunosuppression

For the identification of markers specific to immunosuppression, the inventors used the data generated by the analysis of the HERV-V3 chips from the samples of Example 2.

Thus, the inventors selected the HERV sequences differentially expressed on D3 between the patients considered to be immunodepressed (DR−) and those considered to be immunocompetent (DR+), but which were not differentially expressed between the healthy volunteers of the study and all the patients (whether DR+ or DR−, whether on D1 or D3).

This selection allowed the identification of 17 HERV sequences. For each of the identified sequences, the inventors assigned a score according to several criteria (expression profile, fold change, level of expression, consistency of the expression profiles between the sense and antisense probes, difference in expression visible from D and absence of too much variability between patients). Below Table 14 describes the mode of attributing points for each criterion.

TABLE 14

| CRITERIA | DESCRIPTION | POINTS |
|---|---|---|
| Expression profile | Increase in patients considered to be immunocompetent (DR−) compared to those considered to be immunodepressed (DR +) or Decrease in patients considered to be immunocompetent (DR−) compared to those considered to be immunodepressed (DR+) | 2 or 1 |
| Level of expression | Level of expression generally above 5 | 1 |
| Fold Change | High fold change (log2 FC visually greater than 1.5) | 1 |
| Sense/antisense consistency | Same expression profile between sense and antisense probes | 1 |

TABLE 14-continued

| CRITERIA | DESCRIPTION | POINTS |
|---|---|---|
| Difference visible from D1 | Difference between high DR and low DR patients visible from D1 (even if the difference is small). | 1 |
| Variability | Penalty if the variability is too high. | −1 |
| SCORE | | /6 |

Thus, thanks to this mode of attributing a score, the inventors selected 10 candidates and excluded 7 candidates whose performances seemed insufficient. Here in Table 15, below, the 10 markers identified with their respective score.

TABLE 15

| SEQ ID NO: | NAME OF THE PROBESETS OF THE HERV-V3 CHIP | CHROMOSOMAL LOCATION | SCORE |
|---|---|---|---|
| SEQ ID NO: 13 | 052182701-MALR1129 | chr5:132453630-132454148 | 5 |
| SEQ ID NO: 14 | 190478501-MALR1003 | chr19:41812466-41813010 | 4 |
| SEQ ID NO: 15 | 011790601ERV9sLU5 | chr1:155637287-155637547 | 4 |
| SEQ ID NO: 16 | 052681601-MALR1018 | chr5:170290289-170290812 | 4 |
| SEQ ID NO: 17 | 160627301-MALR1014 | chr16:50662453-50662912 | 4 |
| SEQ ID NO: 18 | 111686702-HERV0861 | chr11:122671887-122672147 | 3 |
| SEQ ID NO: 8 | 141107102-MALR1019 | chr14:91230494-91230820 | 3 |
| SEQ ID NO: 19 | 040318302-MALR1134 | chr4:15825146-15825565 | 2 |
| SEQ ID NO: 20 | 041529101-MALR1026 | chr4:83464568-83464963 | 2 |
| SEQ ID NO: 21 | 141106902-MALR1133 | chr14:91222760-91223118 | 2 |

The sequences SEQ ID NO: 13 to 18 and 19 to 21 are newly identified sequences. As for the sequence SEQ ID NO: 8, this is a sequence which has already been identified in Example 2.

Example 6: Herv Markers of Inflammation

For the identification of specific markers of inflammation, the inventors used the data generated by the analyses of the HERV-V3 chips from the samples of Examples 1 and 2.

Thus, the inventors selected the HERV sequences on the one hand differentially expressed between the LPS condition (immunosuppression condition) and the NS condition (negative controls), in Example 1, and on the other hand differentially expressed between the patients on D1 or D3 compared to healthy volunteers, of Example 2.

This selection made it possible to identify 13 HERV sequences. As in Example 5, for each of the identified sequences, the inventors assigned a score based on the same criteria. The mode of attributing points for each criterion is described in Table 16, below.

TABLE 16

| CRITERIA | DESCRIPTION | POINTS |
|---|---|---|
| Expression profile | Increase in patients compared to healthy volunteers or Decrease in patients compared to healthy volunteers | 2 or 1 |

TABLE 16-continued

| CRITERIA | DESCRIPTION | POINTS |
|---|---|---|
| Level of expression | Level of expression generally above 5 | 1 |
| Fold Change | High fold change (log2 FC visually greater than 1.5) | 1 |
| Sense/antisense consistency | Same expression profile between sense and antisense probes | 1 |
| Difference visible from D1 | Difference between DR+ and low DR− patients visible from D1 (even if the difference is small). | 1 |
| Variability | Penalty if the variability is too high. | −1 |
| SCORE | | /6 |

Thanks to this mode of attributing a score, the inventors selected 7 candidates and excluded 6 candidates whose performances appeared to be insufficient. Here in Table 17, below, the 7 markers identified with their respective score.

TABLE 17

| SEQ ID NO: | NAME OF THE PROBESETS OF THE HERV-V3 CHIP | CHROMOSOMAL LOCATION | SCORE |
|---|---|---|---|
| SEQ ID NO: 1 | 190665001-HERV0376 | chr19:54891074-54891496 | 6 |
| SEQ ID NO: 1 | 190665002-HERV0376 | chr19:54891074-54891496 | 6 |
| SEQ ID NO: 22 | 060281701-MALR1043 | chr6:18403673-18404108 | 5 |
| SEQ ID NO: 23 | 043166601-MALR1018 | chr4:184850413-184850785 | 5 |
| SEQ ID NO: 24 | 100090601-HERV0429 | chr10:5856198-5856795 | 4 |
| SEQ ID NO: 25 | 061529601-HERV0492 | chr6:107800650-107801138 | 3 |
| SEQ ID NO: 26 | 100871501-MALR1020 | chr10:60410534-60411224 | 3 |
| SEQ ID NO: 27 | 170842002-MALR1003 | chr17:78345106-78345577 | 3 |

This strategy for identifying inflammation marker made it possible to identify 6 new sequences (SEQ ID NO: 22 to 27) and to find a sequence already identified in Example 1 (SEQ ID NO: 1). It should also be noted that 2 sets of probes (probesets) target the same HERV sequence (SEQ ID NO: 1).

Example 7: Signature of Immune Status Markers

For this example, the aim was to determine a signature of markers making it possible to best discriminate between patients considered to be immunodepressed and those considered to be immunocompetent. To do this, the inventors used the data generated by the analyses of the HERV-V3 chips from the samples of Examples 2 and 3.

The inventors selected the HERV sequences which were differentially expressed on D3 between the patients considered to be immunodepressed (DR−) and those considered to be immunocompetent (DR+). This selection allowed identifying a list of 193 HERV sequences.

In order to obtain a reduced signature still making it possible to best discriminate between patients considered to be immunodepressed and those considered to be immunocompetent from these 193 HERV sequences, the inventors applied the «Random Forests» method (Tin Kam Ho, Random Decision Forests, AT&T Bell Laboratories). This method makes it possible to classify each sequence according to its discriminating power between the two studied conditions (immunosuppressed and immunocompetent).

Then, to identify the optimal number of sequences in the signature, the inventors calculated the prediction performances on the cohort of example 3, by using the discriminating power for signatures of size ranging from 2 to 30 markers between the patients having a low CD74 ratio between D3 and D1 and those with this same high ratio. Thus they determined that the signature of a size of 10 sequences had the best performances (best area under the curve: AUC) (cf. FIG. 9).

In Table 18, below, the list of markers making up the signature making it possible to best discriminate between patients considered to be immunodepressed and patients considered to be immunocompetent.

TABLE 18

| SEQ ID NO: | NAME OF THE PROBESETS OF THE HERV-V3 CHIP | CHROMOSOMAL LOCATION |
|---|---|---|
| SEQ ID NO: 28 | 081921103-HERV0958 | chr8:125945973-125951030 |
| SEQ ID NO: 29 | 032622601MR41sLU5p | chr3:167401329-167401866 |
| SEQ ID NO: 30 | 220246901-HERV0889 | chr22:36147793-36148208 |

TABLE 18-continued

| SEQ ID NO: | NAME OF THE PROBESETS OF THE HERV-V3 CHIP | CHROMOSOMAL LOCATION |
|---|---|---|
| SEQ ID NO: 31 | 061827101-HERV0856 | chr6:127790579-127792191 |
| SEQ ID NO: 3 | 170369402HE41env | chr17:35505737-35508365 |
| SEQ ID NO: 32 | 170828901-HERV0770 | chr17:77462942-77463350 |
| SEQ ID NO: 28 | 081921101-HERV0958 | chr8:125945973-125951030 |
| SEQ ID NO: 28 | 081921102-HERV0958 | chr8:125945973-125951030 |
| SEQ ID NO: 33 | 190148802-MALR1127 | chr19:14612123-14612747 |
| SEQ ID NO: 34 | 120093401-HERV1034 | chr12:9038254-9038598 |

It will be noted that this signature is composed of 8 sequences using 10 different sets of probes. Indeed, 3 sets of probes target the same sequence (SEQ ID NO: 28). In addition, in this signature we find the sequence SEQ ID NO: 3 already identified in Example 2. The HERV sequences appear in the table above in an order reflecting their «importance» in the stratification of patients according to their immune status, based on a score attributed to them by the Random forests classification algorithm.

The invention claimed is:

1. A method of detecting and/or quantifying expression of Human Endogenous RetroViruses/Mammalian apparent LTR-Retrotransposons (HERV/MaLR) sequences comprising:
   obtaining a blood sample collected from an individual with sepsis; and
   assaying the blood sample to detect and/or quantify expression of a combination of at least two HERV/MaLR sequences,
   wherein the combination includes HERV/MaLR sequences having at least 99% identity with each of SEQ ID NOS: 1, 3, 8, 11, 12, 13, and 28.

2. The method of claim 1, wherein expression of no more than 100 HERV/MaLR sequences are detected and/or quantified.

3. The method of claim 1, wherein expression of no more than 10 HERV/MaLR sequences are detected and/or quantified.

4. The method of claim 1, wherein the blood sample is assayed so as to detect and/or quantify RNA transcripts of the at least two HERV/MaLR sequences.

5. The method of claim 4, wherein the RNA transcripts are mRNA.

6. The method of claim 5, wherein the mRNA is detected and/or quantified by a hybridization, amplification, or sequencing assay.

7. The method of claim 6, wherein the mRNA is reversed transcribed into cDNA and the cDNA is contacted with amplification primers comprising any of SEQ ID NOS: 35, 36, 39, 40, 49, 50, 55, 56, 57, or 58 during amplification so as to obtain amplicons.

8. The method of claim 7, wherein the amplicons are detected with hybridization probes comprising any of SEQ ID NOS: 59-70, 77-82, 99-104, 119-140, or 211-246.

9. The method of claim 1, wherein the individual is in an immunosuppression state.

10. The method of claim 1, wherein the individual is in an immunocompetence state.

11. The method of claim 1, wherein the individual is in an inflammation state.

12. The method of claim 1, wherein the individual is in septic shock.

13. The method of claim 1, wherein the blood sample is collected within 10 days of admission of the individual to a medical facility.

14. The method of claim 1, wherein the blood sample is collected within 5 days of admission of the individual to a medical facility.

15. The method of claim 1, wherein the blood sample is collected within 24 hours of admission of the individual to a medical facility.

* * * * *

SEQUENCE LISTING

```
<160> NUMBER OF SEQ ID NOS: 274

<210> SEQ ID NO 1
<211> LENGTH: 423
<212> TYPE: DNA
<213> ORGANISM: Homo sapiens

<400> SEQUENCE: 1
aaaatcagaa caaactgaag atatgggcca gaacttgtat aaagtgtgaa aagcagtcaa      60 taagaaagt tagaaatact ttgcattttt tttttaatca caggacctga gttaagccaa     120
gaatacagta gaaattttat caagtagaga taagctctca gtaaaggata aaagtgggcc     180 taagtcccctt cagtttcact ggaagtagga cccttacatt ttataattat attttcatac     240
ataagctact ggacaatgaa gtaaatagca atcagtgaaa gagccacata tgaccaactt     300
agatttcctt gagtaaagtc tgtcaagggt aaagctgtga aagtttataa gaaaaaagaa     360
tggggaatta tttggaagac catttgagtt ttgtacacaa gaatttaatg tttgcacact     420
tga                                                                   423

<210> SEQ ID NO 2
<211> LENGTH: 588
<212> TYPE: DNA
<213> ORGANISM: Homo sapiens

<400> SEQUENCE: 2
ataaaccaaa agtaagattc taagcctccc cctcatttaa aggacttcct cctcagccag      60
ggctcttaaa atttaacctg aaagactggt tcaggccatg aagggaaatg ggggtcagac     120
atgcttcatt atgcctctct ggcattaata tcaacacagg ctttcagtct aataagaaac     180
attttacagc ctgtttctct gtgaagcctg ctagctgaaa gcttcatctg caggataaaa     240
ctttggtctc cacaacctct tatcacaact caaacattcc ttcctattga tctccggtct     300
ttagacaaac tcaaccaatt gtcaaccaga aaacgtttca atttacctgt agcctggaaa     360
cgcccacttt gagttgtccc gcctttctag accaaaccga tgtatttctc aagtgtactt     420
```

```
aattgatgtc tcatgctccc taagtgtata aaatcaagct acaccccaac caccttgggc      480
acatgtcatc aggacttcct gaggctgtgt cacaggcata cgtcctcaac cttggcaaaa      540
taaactttct aaattaactg acaccagtct cagattttcc gggttcac                  588
```

<210> SEQ ID NO 3
<211> LENGTH: 2629
<212> TYPE: DNA
<213> ORGANISM: Homo sapiens

<400> SEQUENCE: 3

```
aaccccctgta aagtgactct gaagaagacg agaagccctg ctccagtcac acccagaagc     60
taactggtcc acgcatggct gaagcatgag aaaactcttc atgggactca ttttccttaa    120
aatttggact tgtatagtaa gtacttcaac tgaccttcct cagactgagg actgttccca    180
gtgtatatat caagtcacag aggtaggaca aaaagttgct acagtcttat tttatgctta    240
ttgtaagtgt actgggactg taaaaagaac ttgtttgtat aatgctattc tatacaaggt    300
atgtagccca ggaaatgacc aacctgatgt gtgttatgac ccatctgagc ctcccatgac    360
cacagtttta aaaataagat taagtactga ggactggtgg gggctcataa atgatatgag    420
taaagtgtta gccaaaacag aaggaaagaa aagggattcc caaacaagtc accttgaaat    480
ttgatgcctg tgctgtcatt aatagtaata agttagaaac atgatgtggt tctcttaatt    540
aggaaagagg ctgtatggca gaaataagt acatttgtca tgaattagga ctgtgtggaa     600
ataaatgtag atactggtct tgtgtcattt aggctatgtg ataaaaaat aaaaagaatc     660 ctgtccacct tcagaaaggg aaagtggccc ttcctgtacc agtggtcagt gtaaccccctt   720 agaactagta ataaccaatc cccttgatcc ttgctgaaaa aatggggagc atgtaaccct    780
agaaattgat ggggctggac tggatcctcg agtaaatatc gtggtttgag gagaagttta    840
taaatgctct cctgagccag tatttcaaat cttctatgat gaactaaatg tgccagtacc    900
agaaattcca ggaaaaacaa gaaatttgtt tttgcaataa gccgagcatg tagcccagtc    960
tctcaatgtc acttcatgtt atgtatgtgg aggaactgta atgggagatc aatggccatg   1020
ggaagcccga gaattagtac ctacagaccc agttcctgat aaattcccag ctcaaaagac   1080
tcaccctgat aacttctagg tcctaaaagc ctcaatcatt agacaatact gtatagcaag   1140
agtggggaag gacttcaccc ttcctgtggg aagactcagc tgccttgggc aaaaactgta   1200
taatagtact acaaaaacag ccacctggtg gagttcaaac cacactaaga aaaatccatt   1260
tagttaattc ccaaagttgc aaactgtgtg gacccaccca gagtcccacc aggactggac   1320
agcccccact ggattatact ggatatgtgt gcatagagct tacaccaaat tacccggcca   1380
gtgggcaggt agttgtgtta ttggcactat taaaccatct tcttcctac tgcccataaa    1440 gacaggtgaa ctcctgggct tccctgtcta tgcttcctgc aaaaagagaa gcatagctat   1500
aggaaattgg aaagatgatg aatggccccc tgaaagaata atataatatt atgggcctgc   1560
tacttgggca caagatggct catagggatt ccagactccc atttacatac tcaaccaaat   1620
catatggtta caagctatct tagaaataat cactaataag actggcagag ccttgactat   1680
tctggcccag caagaaactc agatgagaaa tgctatctat caaaatagat tggctcttga   1740
caacttgcta gcagctgaag gaggggtctg taggaaattt aaccttacta attgctgtct   1800
acacatagat gatcagggca agcagttgaa gacagtagtta gaaatataac aaaaattggca  1860 catgtgccca tgcaagtgtg gcatggattt gatcctgggg ccatgtttga aaaatggttc   1920
```

| | |
|---|---|
| ccagtgctaa gaagatttaa aactcttata ataggagtta taatagtaat agaaacctgc | 1980 |
| ttactgctcc cttgtttgct acccatactt cttcaaatga taaaaagctt catcactacc | 2040 |
| ttagtttacc aaaatgcttc agcacaagtg tactatatga atcactatcg atctgtctta | 2100 |
| caagaagaca tgggtagtga aatgaaagt gagaactccc actaatgagt gagattctca | 2160 |
| aagaggggga ataagggagg agaccacccc tcatattgtc ttatgcccaa tttctgcctc | 2220 |
| caaagaagaa gaagtaaaaa ctaaaaggca gaaatgaaat ccacaggcag atagcctggt | 2280 |
| gccgtgccct gggcctggtt aaagatcaac ccctgaccta atcagttacg ttatctatag | 2340 |
| attccagaca ttgtatggaa aagcactgtg aaaatccctg tcctgttctg ttccgttctg | 2400 |
| attactggtg catgcagccc ccagtcatgt accgcctgct tgctcaatca atcacgaccc | 2460 |
| tttcatgtgg accccttag agctgtaagc cctaaaagg acaggaatt gctcactcgg | 2520 |
| ggagctcagt ttttggagac gtgagtctgc tgatgctccc agtggagtaa agctcttcct | 2580 |
| tctacaactc ggtgtctgag tggttttgtc tgcagctcat cctgctaca | 2629 |

<210> SEQ ID NO 4
<211> LENGTH: 379
<212> TYPE: DNA
<213> ORGANISM: Homo sapiens

<400> SEQUENCE: 4

| | |
|---|---|
| tacatgtctc agactcctct gcagccagag gtctggctgt aatttagatt ctgctaagaa | 60 |
| agggaggtgg gatccgtctt cccgcagctc tggcagctgg ccatccctga tggatgtttg | 120 |
| tggttgcagg aatctaacct aggtctcgac tccagttttg tccatgtggg gcagtgatgg | 180 |
| caggggtagt ggtggcatta gcagtagcag tggctgctct ctggcctctg attcggctac | 240 |
| agtggtctaa tattgaaacc aatagtccag tggtggcctc tgccttctgc tcctccagcc | 300 |
| tttccagtga tttagataaa atcccttttct gcctaagatt cctagagtgc tttctgtttt | 360 |
| ctgggctgaa ccttgacta | 379 |

<210> SEQ ID NO 5
<211> LENGTH: 380
<212> TYPE: DNA
<213> ORGANISM: Homo sapiens

<400> SEQUENCE: 5

| | |
|---|---|
| taatcacccc tgtggcagct ttttgaagta aggagttcag tatggttagt gcagagtaaa | 60 |
| gtttggagga ggatagcagt gaacagtaga atggagggac caggtggaga taattgaatc | 120 |
| atggggcagt tcgcatcata gtgagttagt tcttataaga tgtgatggtt ttataaaggg | 180 |
| cttcccctt ctctgggcac tcatttccct ctcctgctgc cacgtgaaga aggacatgtt | 240 |
| tgcttccctt tctgacatga ttgtaagctt cctgaggcct cctcagccct gtggaactgt | 300 |
| gagtcaatta aacctctttc ctttatacat tacccagtct caggcagttc tttatagcag | 360 |
| tgtgagaaca gactaataca | 380 |

<210> SEQ ID NO 6
<211> LENGTH: 466
<212> TYPE: DNA
<213> ORGANISM: Homo sapiens

<400> SEQUENCE: 6

| | |
|---|---|
| agattagcat ttgaattagt aaactgcata aaaaagatcc aacatgagct gacatcatcc | 60 |
| aatccattga gggcccaaat agagcaaaaa ggcagaggaa gagcaaattc tctattcttg | 120 |

```
agctggagta tccatcttct tctgctctca gatatctgag ctcctggttc tcaaacattc      180
ggattctggg acttacacct ccagctctct cagttcccac agttcccagg actttgattt      240
cagactggga gttccaccac tggctccacc agttctcagg catttggatt cagactgaat      300
tacaccacca gctttcctgg ctttacatct ggcaggtggc agatagtgag acttctcgcc      360
ctccaacacc acatgagcca cctcccataa caaatttcct tagttttttt ttaattttat      420 ttttttatg ttggttcagt ttctctgaag aacgctgact aataca                     466

<210> SEQ ID NO 7
<211> LENGTH: 1307
<212> TYPE: DNA
<213> ORGANISM: Homo sapiens

<400> SEQUENCE: 7
ttatagtaga tagtcaggca gacaggagca ggccaagaga ggcccccact accaggaatg       60
tcaggcaacc atcaggtgat ggtcagccaa gttattttg ttgttttttct ttttttttga      120 gatggagtct cactctgttg cccaggttgg agtacagtgg catgacctcg gctcactgca      180
acctctgcta cccgggttca agagattctc ctgcctcaaa ctcccaagta gctgggatta      240
cagtctccca cccgccacca cgcccagcta attgttgtat ttttagtaga gacggggttt      300
tgccacgttg gccaggctgg tctcaaactc ctgacctcag gtgatccgcc tgcctcagcc      360
tcccaaagtg ctgggattac aggcatgagc cactgcaccc agccggccag ccagttgtta      420
agctgactct ctaaagtaat aattggttgc agccagtgcc agggaaaggc agtctcccaa      480
tagatagaaa cacctgaaac tggtgatcag cagcttctga taagatctca ggatttgggc      540
aagaaagctc aagcatgtac attaaggggc aaaatggcag agtttaactg atacatgacc      600
ttacaggaac attcgactgg taagggaaga acgcctcaag taagtatatg cacaactcca      660
gtaaacacac tgggcttgcg gcccctccca agtgctggcc ggccactgcg catgcagaca      720
gcccacccca agggaatcat tgactccaga agattgccaa catataaaac cccaagtcaa      780
aggccaaacc atgcacccaa tctcccaagt tgctcacttg gccttcttcc aagtgtactt      840
gacttccttt cattcctgct ctaatttttt tttttttttt aacacagagt ttcattcttg      900
ttgcccaggc tggagtgcaa cggcacgatc tcggctcact caacctctgc ctcctgggtt      960
ccagtgattc tcctgcctca gcctcccgag tagctggat tataggcata tgccaccatg     1020
cccggctaat tttgtatttt tagtagagac ggggtttctc catgttggtc aggctggtct     1080
tgaatttctg acctcaggtg atccgcccgc cttggcctcc caaagtgctg ggattacagg     1140
tgtgacccac cgtgccaggc ctctaatact ttttaataaa ctctcactcc cgctctaaaa     1200
cttgtctcag tctctctgcc ttatgcccct tggttgaatt tcttctgagg aggcaagaat     1260
tgaggttggg gcaaccagta cagattcact gctgctaaca gttgtag                  1307

<210> SEQ ID NO 8
<211> LENGTH: 327
<212> TYPE: DNA
<213> ORGANISM: Homo sapiens

<400> SEQUENCE: 8
tgtcagagac tggccagata ctcaccaatt ctgcctctct ttcctgcatc cataggaaaa       60
ctacctttcc cagcctccct tgcagttagg ttgaggccac atgcctggga tctgaccaat      120
ggaatgtaag tagcagggat atccgccatt tccacacttg gccaaaaacc cctgtgagat      180
```

| | |
|---|---|
| tctcttttg ctgcatcccc ttacctgtgt gggtgaaaag ggaagacccc aagatgatgg | 240 |
| actctggtga tgggaggatc ctgaatcact gccatcactt tgggaaagac ttgccagaaa | 300 |
| gcagcctctc gttggacttt gcatgaa | 327 |

<210> SEQ ID NO 9
<211> LENGTH: 2948
<212> TYPE: DNA
<213> ORGANISM: Homo sapiens

<400> SEQUENCE: 9

| | |
|---|---|
| gtaaattggt accagaagtg gggtgctact gtaaagatac acaaaatgtg gaagtgactt | 60 |
| tggaactgca tacaggcaga ggttggaaca gtttggaggg cagtttggaa cagttggaac | 120 |
| agtttgaaga agataagaaa atatggaaaa gtttggaact tcctaaagac ttgttaaatg | 180 |
| gctttaacca aaatgctgat aatgttatgg acaataaagt ccaggctgag gtggtctcag | 240 |
| atggagatga ggaacttttg gggagctgga gcaaaagtga atcttgttat gtttagcaaa | 300 |
| gagattagtt gcatttgtcc cttgtcctag agatctatgg aactttgaac ttgagagacg | 360 |
| attatctgga agaagaaatt tctaaagagc aaatcattca agaggtgaca gagcataaga | 420 |
| gtttggaaaa ttcacagctt gagaatgtgg taggagagaa aaatccatgt tcgtgggaat | 480 |
| gggggggcatg gaattaaagc tggttgcaga aatttgcata agaaatgagg actcaaatgt | 540 |
| taattgccaa gacaagggga aaaatgcctc tagggtatgt cagagatctt catgagagac | 600 |
| cctcccatca caggcccaga ggcctaagag gaaaaatga tttcctggga tgggcccagg | 660 |
| gtcccttttct gtgtgcagcc tagggatttg gtgccctgca tcctacccct ccagccattg | 720 |
| ctaaaacagg ccaagatacc aggtcaggct gtggcttcag agggtgcaag ccccaaacct | 780 |
| tggcagcttc cacatggtgt tgaggctgca ggtgcacaaa agtcaagaat tgaggtttgg | 840 |
| gaacctacgc ctaggtttca gaggatgtat ggaaatgctg gatgtccagg caaaagtttg | 900 |
| ctgcaggggt ggaaccctca tgtagaatct ttgctagggt agtgtggaag ggaaatgtgg | 960 |
| tgttggggct cccatacaga gtccccactg gagtacagct agtggagtta agagaagaaa | 1020 |
| gccaccatcc tccaggcccc aggatgatag attcactgac agcttgcacc atgcacttga | 1080 |
| aaaagcccag aaactcaaca ccagcccatg aaagaaacca ggaagaaaga tgtaccctgc | 1140 |
| aaagccacag gagcatagct gcccaaggcc atgggatcct acctcttgca gcagcgtgac | 1200 |
| ctggatatga gacatggagt tgaaggagac tattttggaa ctttaaggtt taatgactgc | 1260 |
| cctattaaat ttagaacttg catggggcca gtagccccct tgtttagtc aatttctccc | 1320 |
| atttggaagg ggtgtattta ctcaatgcct gtactccat tgtatctagg aagtaactaa | 1380 |
| attgctcttg aatttactga ctcataggaa gggaccttcc ttgtctcaga tgagactttg | 1440 |
| gacttggatt ttagagttaa tgctggaatg agtgaagact ttgggggact gttagaaggg | 1500 |
| catgattgtg tttttgaaatg tgagagcatg agatttggga gaggccaggg gtggaatgat | 1560 |
| atgatttggc tataccccaa cccaaatcat cttgaattgt agttcccata agccccatgt | 1620 |
| gtcataggag ggacctggtg gaaggtaatt taatcatggg ggtgattacc ctcatgctgt | 1680 |
| gctcctgata gtgagtgagt tctcataaga tctgatgttt ttataagggg cttttccccct | 1740 |
| ttttgctcag ccttctcctt gatgccacca tgtgaagaag gatatgtttt cttcccctc | 1800 |
| cactatgatt gtaagcttcc tgaggcctcc ccagccatac agaactgtga atcaataaag | 1860 |
| tctctttcct ttataaatta cccagtctca agtatgcctt tattagcagc atgagaatgg | 1920 |
| actaatacac attctttgaa aacatggatg tcgaatctac cacaaaacac aagagttaag | 1980 |

```
gagcaccaac ttcatgtttt ctggttgcaa tacaatctct attttatact aatacttcaa    2040
catagaaggt gtgatacatg tgtatatgtg ggtgtcagct tcaattgaca tgcaaaaccc    2100
tggtgagtca ttaacagttc atttattttc ctgttttaga gttaatataa taaaatgcat    2160
aggctataca atatgtgctc ctttatgtct gggttatttt gacatgattg ttataaatgc    2220
attcatgctg tagcagtgat gtgttctttt ctcattgtaa tgtagtatct aatcgtgtta    2280
ccatttcgca atttatccat tttataaaag gatgcatgtt ggggatttgg tttattaaac    2340
aaatgtctgt tggatattgg cttatttcta ggttttcagg ttttcgcttg tcttaaaaag    2400
cttctataaa cacatatgac tgtgtttgga tggacatgtg ctctctggaa gtattaccat    2460
ttgaagaaac ttaatgtgaa ttacacactc tccagaggtg ggaggttgat aattgaaagt    2520
ccacaccacc cccctcctca ggcagctaga agctttggat atctaatcat ggtttaccat    2580
tagaggcttt gttgattacc ataatgcttg ttggaaatgg tccttgatgg gataaataag    2640
tggaattcaa ggtttgtgga gttccaagtg ccaaaatagg cactcctatt gttccataaa    2700
cacagtataa gaacccagca gtgccaacaa ccaatgccct ttggaataaa gtctgtgttt    2760
gaaactgtct tgagtttgga caatcatagc attttgtcat ttaaactcaa ctaggttcag    2820
tgaatcctac atgtagaaca ttgtcatgtc tccctagagt gaaacattca tgaaaagtgc    2880
tcttcagggc aggcagctgg gagcttggca acttttgcaca actggctgca tggctgtttc    2940
tgtgcctg                                                              2948

<210> SEQ ID NO 10
<211> LENGTH: 356
<212> TYPE: DNA
<213> ORGANISM: Homo sapiens

<400> SEQUENCE: 10
gtgatagtca ttcgtagtgc tgctcaccaa ataggcccag ttctccctat tctgagcaca     60
tggtgtatca catgtcctcg tccccactgt ggggactctt cctagctcat gagttatatg    120 tgtggcccctt ctacatgaaa gttgtaacag ccatgagaga ccctccaaag caggcttcct   180
gctctagcaa ccaaccaata acatttgaaa tagtgactgt gactgctcct tcagcctaag    240
tccctaactg tctgcaaacc cacaatggac ctgttgcatg tgtaagaaat aagcccttgt    300
tattttaagc cactgagatt taggagctat ttgttacagc agcataaccct tgactg       356

<210> SEQ ID NO 11
<211> LENGTH: 497
<212> TYPE: DNA
<213> ORGANISM: Homo sapiens

<400> SEQUENCE: 11
gttgggtggc tgcatcctat ggtgtttcta catgtttcat gatagctttt atcttgaata     60
atcttttccg gcatgttggt atagtgaaca gccttggaaa ataaagatag tgtttcctat    120
tgtgtcagaa ggcaaatttt ttcctgacca ggcttataaa gataacatct tccgctggag    180
caaaggttgg gcagatttgt tagcagtccc ctcataaaaa tcaaggtttt tcaagctcaa    240
agtccttcag ctatgacata gatctactgt gtatatgaca tccacctggc cctgccatca    300
tcatccccat gagactagga gggacaagaa ccagcgtgaa cataaagctc atagttcctg    360
cagtgctgtg aataataaag tcctttgtct ctgacccagg agcattgtgt cttctgccag    420
```

```
catctatgaa actatggcag actaatttgt tagcttgcaa gtagcataaa atctcagacc    480
cttcttagtt cctgaca                                                   497

<210> SEQ ID NO 12
<211> LENGTH: 532
<212> TYPE: DNA
<213> ORGANISM: Homo sapiens

<400> SEQUENCE: 12
tggatttctg tagtttctgc ctgcctgtga tacctccctc tttcttctgg taacaaactg     60
ggctgtccac ttgggaattg ttgattggtg agttgtcaaa tgcagggccc accactctcc    120
tcctctgggt tcacgatcca ggctagcttc atacaatggt atatgcaatg attagttcag    180
aattttgtgt gtgtgtgtga gtgtgtgtgt gtgtgtgtgt gtgtgtgtgc gtgtgtatgt    240
gatgtttaat gggggaccag aatcctttct tggagattac catggttgct tggagagaga    300
atcttctttt tttgagagtg tgtgtgctaa ggatcacagg aacctggatg tgttgagaga    360
cagagactgc aagagtaatg acatgacatt gtctgaactt tgggaaacaa ttatgtttgg    420
agccagagct accccttgga ctttccagtt aatcgaatca atccattgtc tttttaacct    480
agactagttc caactgggat tctgtcacta gtatctgcat ggtcctaatt tc           532

<210> SEQ ID NO 13
<211> LENGTH: 519
<212> TYPE: DNA
<213> ORGANISM: Homo sapiens

<400> SEQUENCE: 13
ctctggatga gggtatggtg aatttaaaag atggttgcaa attctttgac atttctccaa     60
tggagaggtg ggtctgtgtc tccttccttg aacctgtgtg gatttctgac tacagtggaa    120
atgagctatg tgacttccaa ggctgggaca tacacagcca tgcagcttct gtcttgctgg    180
ccagaacact cacaccagag acttgaggtg cctcgtaaga ggtccaatga ccaggccatg    240
gtgctggaga catcatgtgt agtctctctg gtcaacagtc ccagctgagc ccagccttcc    300
agctctcttt gccaagtgaa caacgatctt acaagtggac ccttcagccc agctgttcc     360 aactcccagt tattccagtc acctcgagtc attccagtca tcctagccgt cgtagagcag    420
agaattgccc ttctgactcc ttgacagtgg cccaaaaaat ggttgttgtt ttatgctact    480
aagttttgag gtggtttgtt atgtagcgtt caataacta                           519

<210> SEQ ID NO 14
<211> LENGTH: 545
<212> TYPE: DNA
<213> ORGANISM: Homo sapiens

<400> SEQUENCE: 14
cccctctcaa agatgcacac atcctcatcc caagatctgt gaatatggca catggtcaaa     60
gacacttagc agataaatga aggatgatga gatggggaga ttattgtggt ttatccaggt    120
gggtccaaaa taaccataca agtgagacag ggaggcgggg aagtcagtga ggatggaagc    180
agagcacaga gaggtttcaa gatgctgtac tgctcgcttt gaagatggag gaaggggcca    240
aagttaagga tgcaggcggc ctctagtaat tggaaaaggt gagggaacag acttttccct    300
ggagctgcca ggaagaacac agccaagtgg acacgttgtt gttttatgcc actaagttaa    360
caatggagtt gtcatctctg ttgcctaggc cagcgtgcag tggtgtgatc agagctcact    420
```

```
gcagcctcaa cctcctgggc tcaagcgatc ctcctgcctc agcctcttga gtaagtggga    480
ccaagacaca aaccaacatg cctggcctgt gggaatttgt cacagcatca acaggaaact    540
gacac                                                                545

<210> SEQ ID NO 15
<211> LENGTH: 261
<212> TYPE: DNA
<213> ORGANISM: Homo sapiens

<400> SEQUENCE: 15
tctctaatgg agctgtaaca ctcaccactg aggtccatgg cttctttcct tgaagcctgt     60
gaaaccacga acccttcaat caagaaaaga cctttgatca ggagaagact tctcgtctca   120
tttctgggga cacattcagg atttctccaa agcagtgagt aacattgaac ccctcttgct   180
tgctattctg ttctatcttc tcattagaaa ttggaagaaa acaccaggca cctgtcagcc   240
atttaaatgt gacaagcggc c                                            261

<210> SEQ ID NO 16
<211> LENGTH: 524
<212> TYPE: DNA
<213> ORGANISM: Homo sapiens

<400> SEQUENCE: 16
tgtggcagac atggctgctt gcctacccaa tacccactct cccttttgttt tcctactgac    60 aggtcctggg tttcattcag ggcagtaaat gtgcttgttc aaaatattta actctccagg   120
ctcccttgca gatggtggag gtcacatgac tctgttgtgg acagtaagat ataaccaaag   180
tctgctggat ggagcttctg gaaaagttac tacttccctg gaaaaaaggg agcatgcatt   240
taccattcac catacacctt ctcctctttg cctttctccc cgtctccctg cctgccatgg   300
agatatgatg cctaaaggtg gagtagccaa ctgacaactg ttaggacaga agccacaggc   360 ttttccatc ggttagatga agcctgggtt cttgatgtct tctttcacca tcccctggca   420
cccgcctata catttattac ttgaaacaga ctgacccttta tttggttagg ccactgtggt   480
caggtttctg caacatgggg tcacatgcct cccaactga caca                     524

<210> SEQ ID NO 17
<211> LENGTH: 460
<212> TYPE: DNA
<213> ORGANISM: Homo sapiens

<400> SEQUENCE: 17
ggtgaattgc agggatggcc tgggtcttca tccctcgtct ccatgccatt tgccacacac     60
atttgcagtt cttgtcacta aacaagcacg gttaatttcc ctcccctttg agtccgggct   120
gtcctggaca ctggcttcgg cccatgtcat gtggcagaag ggacagtgtg ccagctccaa   180
gccttggcct caagagacct cgtgcatttc acttgccccc ttgagcttct gttgttgtca   240
tgagaagaaa atgcccaggg tatccggctg agacacagg atgaggtgac acatggatct   300
gagccaaggg cagctgagat ccgttgacgc cagcccactc cgacatgtgg gtgaactcag   360
ccaagatcag ccaattctca gccatgtgtt ttgtgaactc aaatcagatg ttattgttgt   420
tttggggctg tttgttatgt aggaatagct agctgataca                        460

<210> SEQ ID NO 18
<211> LENGTH: 261
<212> TYPE: DNA
<213> ORGANISM: Homo sapiens
```

<400> SEQUENCE: 18

```
gtatgtgaag ttttttttgg tttgttttttt gttgtttggt tttttaatgt tcctttttcca     60
tcttctgcat gctggggcac cagccgctgc cccagaatgg gttgtcctgg gaaacaggtc    120
atgcagggct accgatgttt agtctggaaa agacatgcag agataaggaa gatgttgagg    180
caggacagaa ccaggctcct gttagtccaa caaaagttta ctgagcagtg actttgtgtc    240
aggcacctgg gaattgtgcc g                                              261
```

<210> SEQ ID NO 19
<211> LENGTH: 420
<212> TYPE: DNA
<213> ORGANISM: Homo sapiens

<400> SEQUENCE: 19

```
tgctatagtt tggatattta actctccaaa ccttatgttg aaattcgacc cccagtgttg     60
gagctcggga ctagtaggag gtgtttgggt catagggatg atcctgcacg aatggcatgg    120
tgctgtcctt atagtaatga gttcttactc tactagttcc caggacagct ggtcattaca    180
aacagcctgg cacctcccct gacctctcct tgctttcctc cctcaccatg tgatctctgt    240
aaatgccagc tccccttccc cttctccatg agtggaaaca gcctcaggcc ttcacccgaa    300
gtggatgctg gtaccctact tcttgtacag cctgcgtaac tgtgagtcaa ataaaccttct    360
tttctttata aattacgcag cctcaggtat tccttaatag caacacaaat ggactaatat    420
```

<210> SEQ ID NO 20
<211> LENGTH: 396
<212> TYPE: DNA
<213> ORGANISM: Homo sapiens

<400> SEQUENCE: 20

```
tagtggacac tttttaggat gtctgccaag cctactttt acaaactttt tttgcccctga     60
cataagagtt tgccagttac ccctgtaccc acctttcacc agagctgacc caaacagaac    120
caatgagatt cttgcctggc aatctggagg tattacatag ccaattggca gatcttatgc    180
tctagaagag atctaaatgc aggagctgtg ggttggctgt tttctggcct gccagtggat    240
gaagaaacaa aaaggtctgg aaggatagca atgtgcagac acagaaagtt ctatggcatt    300
ctagctcctg gttccaattc cttcctaaag ttcagctgct ttctgcctac agttcttatg    360
atatacctct acattcccta ttttagccca agttgg                              396
```

<210> SEQ ID NO 21
<211> LENGTH: 359
<212> TYPE: DNA
<213> ORGANISM: Homo sapiens

<400> SEQUENCE: 21

```
ttatggactc aatatgtacc ctcaaatttt gtatgttgaa cctaatcctc aattgttgga     60
atttgaaagt ggggtctttg ggaggtaata agattgagat gaggtcatga gtgagggtca    120
ggatgtgaag tgctcttata agaaaaagag aaaccagagc tctcgctctc tccaccacat    180
gcggactcag caagaaggcg gccatctgta agccaggaag agagtcccca ccagtgaatc    240
aaaactactg gcaccttgat gttggacttc ccaatctcta gaactgtgag aactaaattt    300
ctgttgttca agccacctag tctatagttg ttttttaaaa tagcagcttg agctacgac    359
```

<210> SEQ ID NO 22

```
<211> LENGTH: 436
<212> TYPE: DNA
<213> ORGANISM: Homo sapiens

<400> SEQUENCE: 22
tgctatggtt tggatatggt ttgtttatcc ccaccaaaat tcacattgaa atttcttccc    60
cagtgtagta gtgttgggag gtgggaccta gttggggaat ggcttggtgc cactctctag   120
gtagtggctg agttcttgct gtggcgagaa tgaattagtt cttgcgggaa tgaattctta   180
atagttcctg ccagagtgag tttttagaaa gccaggatgc cccttgggtt ttgtctcttt   240
tcacatgtcc actttccctt tgaccttctc tgctgtgttt tgacctagca tgagaccttc   300
accagaagcc aagtagatgt cagcaccgtg cttctctaac tttccacctg caaaactgtg   360
agctaaataa acctcttttc tttataaatt acctagcctc tgtattctgt tatagcaaca   420
caaaatggac taagac                                                   436

<210> SEQ ID NO 23
<211> LENGTH: 373
<212> TYPE: DNA
<213> ORGANISM: Homo sapiens

<400> SEQUENCE: 23
ccagcctcgc acctaagaac gccgtgggat gcagtttcag acagtgagaa atctgctggg    60
gatgcctggg aaagggacat acctggcagg tgccgctcca tggccttctt gctgccttga   120
attgggacat gagcctgagt cgcagcagcc gtcttgtgac tgagaggtgg caagcaggag   180
gaagaggcta agagaataga gacactgttg agctgctgaa gcacagcaag cggccacttc   240
tctatgcttc ttgctatttg actgttaagc tagtgcaagt tacttttctg gtcagaatga   300
attcataact gaaacatgct ttaaagtatg actattatta ttaaatgcag cataagcttt   360
ccatagctgc tac                                                      373

<210> SEQ ID NO 24
<211> LENGTH: 598
<212> TYPE: DNA
<213> ORGANISM: Homo sapiens

<400> SEQUENCE: 24
tgtaaggtat atagatgtga tttggtcaag gtagagaccg aggcggatat acaggcctgc    60
acggctcagt gagtttggtg cgcaggcgca cacctccgct tgttacataa cctgtttgtg   120
taagttcata cttggctctg agccactatt gtctgtaaaa ggtataactg ccctgctgac   180
gccgtacagg tgcttttgag gctcagcttg gctcgacatg gcttgatgtg gtgggtgcgc   240
tggcgcccag agaaagggag acagccaaag ctgtccatct tgtagacaga caggagggag   300
ccaggacaca gctctgcttg cttgtgccag agaaagaaag agttaagctg ctgaccctga   360
aggcaaggga gagccggggg tcacaggagc cacagagcca aagcaaatag cagagataaa   420
ggtggacagg gtgagagagc taatgtgagt aagctgctaa taaaaagcca ttgatgagaa   480
ctgctgctga ataaaaccat attcacctgc ctaggccccc tgcaccaaag cgtttctgct   540
catccacccc actcaccttg gacttcagca tgggctggac ctggaccggg gtctgaca    598

<210> SEQ ID NO 25
<211> LENGTH: 489
<212> TYPE: DNA
<213> ORGANISM: Homo sapiens
```

```
<400> SEQUENCE: 25
tattgctttt cagcaacaaa tccatctttc tttcccctc tctgttatac tggggcccaa      60
ttctacagac attacttctt tgccagttgg cttaatgtta ggtcctgtca atagagggca    120
ttggagacac attgcaagtc tggaagagga aaaaggact ttttcttctt ccagtgttgt    180 attttctac ttggtggcaa gtagatcaat aagcaagggt cctggcagtg ttaaacagag     240
gaggacagtt atttgatttg ggagcaagtg ctccccaata tcagtcaact tgccctgtcc    300
attgacaaga gtccgaatct taaccttgca ggggctcccc tcttccaagt ttctgcgttc    360
cttcatcatt tactttttctt tgaactttca gagtagttac tgatctctgc atttactact   420
ttaagagttt tttatattaa aacttcccta ttccaattgc caatgtggtt tatgtcttct    480
gactgaacc                                                             489

<210> SEQ ID NO 26
<211> LENGTH: 691
<212> TYPE: DNA
<213> ORGANISM: Homo sapiens

<400> SEQUENCE: 26
gtagcagaga ctggctagat atttttcaaa caattttcat gatcctgggt gaagccatgt      60
gtctgaggat gaaaggggat gcagattgat gtgacatgtg gcacctccag gcctggtcct    120
taaaaacctc tcacccaatt ttttttttctt tgagacaggg tctcaatctg ttgcccaagc    180
tggagtgcaa ttgtgcaatc atagctcacc gcatcctcaa actccctggtt caaggaatcc    240 tcctgtctta gcatcctgag tagctgggac tacaggtgca ccagaatgc ctggccaat      300 ttttttttt tcattttttg cagtgacaag gtctccctat gtgttgctca tgctggtctt    360
gaactcccgg cctcaggcaa tcctcctgtc tctgcttccc aaagtgctgg aattacaggc    420
gtaagccact gtacctggcc tctcccatcc aatcttatc cctctccttc cttttttcttc    480 tcctggcttt tgacccagct accaaggatc cactggggga actccaagga actggtggat    540
aatggagccc caagctggaa ggcgcttggt ttccaaataa ctgcagcctc tacaccaagc    600
cacattggac tgtgacgtga accagaaaca aacttttatt atgttagatt tggaggttgt    660
ttgttttagc agttaggtta cactgactca c                                   691

<210> SEQ ID NO 27
<211> LENGTH: 472
<212> TYPE: DNA
<213> ORGANISM: Homo sapiens

<400> SEQUENCE: 27
tgtactgggt cgaatggcgt ccccccccac caaattcatg tctgcatgga acctacaaat      60
gtgactttgt ttggaaagag ggtctttgca gatgtaatta agatgtactc cacaggcctg    120
gggagatcaa ggctaacagc atgttgtatg aggatggccc cagtcaatg actgatgccc      180 ttatatgagg gaaatctgga cacagacaca cagagaaggc cacgcggtgg tggaggcaga    240
gatgggagag atgtgtctac aagccaagga gcgagcagga ccgccggcca ccaccaggag    300
ctggcagggg caaggaagtc attcttccct gggggcttca gagggagcac ggtcccagta    360
caccttgagt gttggccttc tggcctccag agctgtgaga gaatccattt tggttgtttg    420
aagctgctga gtttgtggcg ttttgttacg gctgtcccag gaaaggaata ca           472

<210> SEQ ID NO 28
```

<211> LENGTH: 5058
<212> TYPE: DNA
<213> ORGANISM: Homo sapiens

<400> SEQUENCE: 28

| | | | | | |
|---|---|---|---|---|---|
| tgatgccatg | acttggacaa | aatgcccatt | gcctctgggt | cctgctttct | tcacccagtg | 60 |
| ctgccttatt | ggactccttg | tgcctctcct | tggctgggga | aatcagaata | cacagtggta | 120 |
| agtcatgatt | tctaatccag | tgctccagac | gtctgtctgt | tgtagcacag | tgagaagttg | 180 |
| acttatattt | ctctcatttt | tgtcattttc | ttctgttttt | ccatctttcc | cttctgcctt | 240 |
| ttttgagtgt | ggtgaaagcc | cctcattctc | tcctgagaat | catacctgag | ttgaaatccc | 300 |
| aaagcctcta | gcaccagcag | gtgtcccttc | cattatcatg | agaaaccgtc | aatttggctg | 360 |
| ttgttctcca | gaaccctcaa | ctctggggta | tgctctgtgt | tactatggta | ataattccac | 420 |
| ccactttctt | ccaaaaaaaa | aaatggcaat | attttacaac | ttaaatttca | atggcctctt | 480 |
| tggagaacgt | agaatttttc | caaattgcct | cattctgcga | agggcaattg | aatcctgtgc | 540 |
| caccaagatc | tcatccaagc | aatagatgct | tgttagtgg | tggtgggcat | ttggtacaaa | 600 |
| gaggcagaaa | aaaaaaatgc | tctctctcaa | aaacttttca | gtgaccattg | cttcttttcaa | 660 |
| agacagtcat | ccttccccaa | tctgtgacct | gtgtcttctc | atcacctatc | ccccaatctc | 720 |
| tcttttctac | catcttccat | gttcccttca | gctcccttta | atccttggat | cttcctcttt | 780 |
| caaccctcta | tctcctccac | ctttccatcc | actcctgcca | gaccttttcct | ctcccactct | 840 |
| ggcccctcaa | ttccttataa | tcccttgagc | tttaagtcct | gtcccttcat | gggaggctct | 900 |
| agagaagccc | aggggcacta | agagcaacag | cctgaggcta | aaaaggctca | ccggaaacag | 960 |
| gctgaatgtt | ttatcccctc | aggtgggctc | tggagacacc | agatgaccgc | ttggtctctc | 1020 |
| ctccatgcct | cccttgaaat | tgagtccaca | gcttccctag | aattatacac | cagagccaag | 1080 |
| ggtagcttat | gggtctccta | cacaaatatt | ggtgaagatg | cttcagttct | catactgaac | 1140 |
| aggttacttc | aacttgcccc | atctaccaaa | aatattatcc | ttgtaaaaat | ataaacgtga | 1200 |
| ggcaatgatg | atactttgtt | tgtttgttta | tttgtttgtt | ttttgagatg | gaatctcact | 1260 |
| ctgttgccag | gctggtgtac | agtggtgcaa | tctcgactca | ctgcaatctc | tacctcccag | 1320 |
| gttcaagcga | ttctcctgcc | gcagcctcca | aagtagctgg | gattacaagc | acatgccacc | 1380 |
| atgctcagct | aattttgta | tttttagtag | acactgtgtt | tcaccatgtt | ggccaggatg | 1440 |
| gtctcgatct | tctgacttaa | tgatctgacc | gccttggcct | cccaaagtgc | tgagattaca | 1500 |
| ggcatgagcc | accgtgccca | gtcaatactc | tgttttttta | tatgaatcag | tgagtttgc | 1560 |
| atttctgtga | ttatgcctaa | gtcatggcta | aaatttaaaa | attaaagctg | taagttggct | 1620 |
| atgtctgcct | atatgtttat | gtatgtgtgt | ttgtgcatgt | gcacatacat | tttgtttgtg | 1680 |
| taatatttc | ctacctccag | atggtattac | cacattaaat | tataaaacgc | cttaaataag | 1740 |
| ctccttctgg | attgtcttag | agatgaatga | gagcctacac | aagttaagta | ttcttgaact | 1800 |
| tccttgaaat | taggaaaatc | aaatttctaa | tatcatcaat | gtgaaaaag | tatttttata | 1860 |
| aaagcttaac | aaagtgttta | aaaattcaag | ttcacctaat | ttagataaac | ctttggccat | 1920 |
| tgagagtagt | ttaatataat | tgatttaata | aatatagcta | tgtcttctga | gttgtccaca | 1980 |
| tggtaagaat | acattttgt | tctacttgag | tatttttttc | ctaaacctat | acaaatatac | 2040 |
| tgaatctctt | tgcttgataa | tctaaatata | ttccttggtat | attctaacta | tatgtttgat | 2100 |
| atattcatga | cacattatgt | ctcatgatta | tcatgttatt | tctttttttt | tttttttttt | 2160 |
| tttttttttt | tgagatggag | tctcactctg | ttgcccaggc | tggagtgcag | tggcacgatc | 2220 |

```
tcggctcact acaacctccg cctcccaggt tcaagagatt ctcctgcctc agcctcccga   2280
gtagctggga ctacaggtga ctgccatcac acctggctaa ttttttgtatt tttagtagag   2340 acggggtttt accatgttgg ccaggctggt ctccaactcc tgaccttatg cttgtgatcc   2400
gcctgcctca gcctcccaaa ctgctgggat tacaggcatg agccactgcg cccagataat   2460
catgttatat ctgaaaatgt tttctctata aaaactatgc ccatccactt tcataaattt   2520
gatgtaatat ccacccttttt tgaaaataa aattaattat tatgtttaca catattttct   2580
ctgaaacttt ttgtagcaac tttaagtgcc ataacgacaa ttaaattttt ctgtcaatgt   2640
attattttta tagcaaactt tcatcagatc ttttactttc aaaaattatc aaaaatatgt   2700
taaccacagc aattttaagt cttttgttat ctatggagga ctttgtttcc acaaaaagg   2760 actgactcag aagtatgtgg aaaggatta tgctaggtgc tgttgtgtta aagtttctaa   2820
ttacgttgtt taagtaactt tgggaccaaa acaatgaact gagttaggaa ttccagaact   2880
ctagttgaaa aagagatggg ttcataagcc tactaatccg ggatcaagtg ggacaagaac   2940
taattccaca ggagtgaatg aactgatgat agataattat gggactttt tggaataggg   3000 ctataggct attcctttaa tgtactattt tctttttttt tttgagacag agttttgctc   3060
ttatgcccag gctggagtgc aatggcgtga tctcagctca ctgcaacctc tgcctcccag   3120
gttcaaacaa ttctcctgtc tcagcctccc aagtagctgg gattacaggg tagtgccacc   3180
acacttggct gttttttgtat tttagtagt gacgggtttt caccatgttg gccaggatgg   3240
tctcgatctc ttgacctcat gatccacccg cctcggcctc ccaaagtgct ggaataacag   3300
atgtgagcca ccacgctcgg cctaatatcc tattttctgg acataagaaa accctcctc   3360 tttttttttaa gctattcatc actcataaca atttcataga ccatgctaat ttcttgtaaa   3420
cagaaatgaa acttctttct tttcttccct gactcaccca ttcaaaattt ggaaattctc   3480
cttgagtctt cttatttca tggcaatatg gttatttgca tagattcagt aagagtctgt   3540
cctctttgtt aacagggcac aaaaacattg gtaatacaac caaggctttg cctggatgtc   3600
atatttgaga gtgacgctta tttaatcaga tatgaccaga cacttttaag gaactaaggt   3660
tgaccttata gggccaatgc ttacaaagct cctcttgcga aaactggctt gaaacctggc   3720
tttgcagggt ttgcagcttt gcaggtgagc aaggaatgtc acttcccagc aggctctgga   3780
atcttaggat atttgtggga tctcaagaag aaaggaatgc ctgccaaatc gataggtact   3840
gcatgtgaaa tctgatgtga gttgttggct tggcttctta tcctcaagag gctttgaaaa   3900
gtccaatttg acattcttta tgaaaacttc cagcaaagca aatataatat gatctatatg   3960
taaattgctg ctcttgcagc acctatgcaa ataaccaggc cgaatctcat gagaccaacc   4020 ttaatttgt atcaagaata atctttcttt gagattgtct ttgatcaaaa gaggaggagt   4080
aactgtagaa agaaaatttg tgtttccatg ggaaatcata gcacatcttt ctggattatc   4140
agattctgat cctgttaatt tgtgtttgag ctatttagtg cctcttggta aactgagagt   4200
aactgatagt tatgcaaact ctctcttctc tagtagagat ttaattgact ttctctcaca   4260
ctatgggaca atcagttttt gtaactacta ataaattgta cttgaatctg ttatcttgca   4320
caaattgtcc acttttacta aattttcaaa tcttccaatt tccctcaata tctagccata   4380 aaccccctcaa ctaacgttcc aattttttctc ctttttttgtt actcatagtc actgagaaaa   4440
ctttactatc cagatgacag ttaagaccct aggttgcctt gtggctgcc cccagtctct   4500 gaagtattac tacaatctca agtctgatga cttgttataa acatataaag acccatcatt   4560
```

```
gctagcagac tatgcatggt tctctttttc tctggacaag ccctgactgg accacaaaaa      4620
aaggatggga aatgctcagg tcacgcatgt tctgatagaa gaggtaatcc aggctctggg      4680
caacattacc aagagcatca aaacgctcaa agagcaatgc tacatgatca aagggctca      4740 tccactaacc ccctgaaatc ccctgaaatg gataccttg ggttcaactt ctgtcttttct      4800 cagtttaatc tctcttttcta tattaacatt tctctttttt cctttaggt atcccacttc      4860 taagatgcct gatctgaagg acagtaaaac aactgacctt tgccagcatg taaaacacat      4920
ggtttaacta gtcctccagg aacaacactg agcaatcctg acctgggact actttactcg      4980
gccatctcct acttgagatg ctccttgtct ctctgttcaa ggacaccttt tctgagcctt      5040
tcttgaacaa gagtggag                                                  5058

<210> SEQ ID NO 29
<211> LENGTH: 538
<212> TYPE: DNA
<213> ORGANISM: Homo sapiens

<400> SEQUENCE: 29
tgtcagaggt gtgtgaacca gagcaactcc gtctagaaca ggagctgggt aaaatgaggc       60
tgcgacccat ggggctgcat tcccagacag ttaaggcatt ctaagtatag gaggttggca      120
gaagatacag gtcataaaga ccttgctgat aaaacagttt acttcaaaga agccaactaa      180
aaccaaccaa aaccaagatg gtgatgagtg acctctggtt gtcctcactg ctacactccc      240
accagtgcca tgacagtttta cagatgacat ggcaacatca ggaagttacc ctatatggtc      300 taaaagggg aggcataaat aattcacccc ttgtttagca tataatcaag aaatggccat      360
aaaaataagc aaccagcagc cttccgggct gctgtctata gggtagccat ttttttgttcc      420 tttacttacc taatgaactt gctttcactt tactctatgg actcgccctg aattccttct      480
tacacgagat ccaagagccc tttcttgagg tctgggtctg cacccctttc ctgcaaca       538

<210> SEQ ID NO 30
<211> LENGTH: 416
<212> TYPE: DNA
<213> ORGANISM: Homo sapiens

<400> SEQUENCE: 30
gttaaagcaa acttaaaatg aacacctggg caaacaaaag caaacaggcc ttcagaaagg       60 ctgtaaccccc ccttaaactg ccaactatgg ggaacttaac tggagtcgtt tcagatgggt      120
gcttacgtta ggcacaaaca aaacttaact tcggccagtc atgagcagcc agctgacaga      180
cgggtacacg actaggaatt ttccaacaag gtaaaccaaa aacataatt tgacaactgc      240 aacaaatcaa ataatgtcct tattccactt ccatattcac cctataaata cctgcctctg      300 acactttttcc atcataacat gaaatgtctt tcattttgat gtttcccact tcatgacttg      360
cttcttcctc aaataaagtc ttcaaaattc gattggacct cagattttc tttgac           416

<210> SEQ ID NO 31
<211> LENGTH: 1613
<212> TYPE: DNA
<213> ORGANISM: Homo sapiens

<400> SEQUENCE: 31
tgatggcagc ggcggcccac cttgagtggc cgctgcatga cactggctac aatgggggag       60
gcacagccag ggctgagtgc tccatagaac tggtgggagc cgggaacagg tggaagccat      120 gccccctcc aagttggagg agctggagcc ctgccctccc aggggcagct gtggcagagc      180
```

```
agccagctgt ggactcaggc atcactgcac tctcagggcc ccaggaaaca cccttgcccc    240
ttcaggctca aaagtgcctg ctctcgctgc ctgacctctg cccattccca gtgcccactc    300
caatttcaga gcaaagttgt ggccaagcct gggggctgtc acgactcggc tgggtgtgtg    360
cacgcttggg gcagcactga aacaccagcc ccctatcacc tcagcctcct ccagattttg    420
ggtgctcaca acatgggag ggagggtgag gtgggggcta agggtggctc agcgcagtct    480
tgcaggcacc acttggcaca aagagccagg gcaccatagg caccatggag agcaggttaa    540
tggtggtagg atgcaaacag gctcctgggc agaaaggagc agatccccag taaagcccca    600
tcttcaggcc agggacggcc tgaagcctgc cggagggctg ccatggagtg agaacttaat    660
ggagcttgct ctggggcctc ccatgactgc tcacgggccg atcagcacct actttctccc    720
ctcttaagcc cataaaaatc ttggactcag ccagacttga gcagatgatg ggatggcctg    780
cctacagaaa ggaactaccc attgtgggtc tcctgtctcc tgagagctga gtggacaacg    840
ggacaatcag cctgcagaaa ggagctaccc actgtgggtc tcctttctgc tgacagctga    900
acagatattg ggatgacctg cctatggaga ggagctaacc actgtgggtc tcctctgagc    960
tgttctgttg ctcaataaag tacctcttca ccttgctcac cctctacttg tctgcataac   1020
tcattcttcc tggatgcagt acaagaactt gggacctgcc gaatggtggg gctgaaagag   1080
atgtaacaca aacagggctg aaatacaccc cctgcttgcc acatggcagg caacaagaaa   1140
aagataagaa agaaggagag aagagtttca gcccttcaga caacccagac ctgggagcac   1200
cctgagccag ggctgtgatg cccttttttgg ggttctgtgg ttcctggcat ctccaagttt   1260
ctgggtgcca ccacattccc tggtgccagc catggaagct acttgcagtg tgcctcatcc   1320
agccacagcc ttgcagggag ctggtgcctg gcactgccca ccctgctgca gccagagtgc   1380
ctggctgtgg gcagtggctg gaccccatgc ttgctcattc acacaatcct caccgctctg   1440
tgcctggctc acccttggca ggcatgggat ccaggtttgt cacgcaagct gagttcaggc   1500
tgccaggccg agtgggcaca tcaagcacag tgggccaaag caaaattcag acaaaggcac   1560
caccgaccac agaggtttct ggacagaaaa gcgacacctg aaggatccta tga          1613
```

<210> SEQ ID NO 32
<211> LENGTH: 409
<212> TYPE: DNA
<213> ORGANISM: Homo sapiens

<400> SEQUENCE: 32

```
gcaatcagga gcctgggtaa agcagactgt gtgctctgat gggggtgggc ctcacccgat     60
cagttgaagg caacagggct tggaacgcac actccaagat acagtgcctt ggcatagtaa    120
atattttcag ctgaaggaat ttaagaaatg gcaggtccaa gaagaactca ctgacctgcc    180
ccttctctga agtagatcat aagcccctca cgtaagaggt gccctcccta cacccagcgg    240
aaaggaacag cctcatctcc agagacagag gatctgagag gggcccccagt acacaggtct   300 tgccgagacc cccacgggct cactgttcag ctcatctttt gttgctctgt cacagtttcc    360
cacgactttc cactcttcat caaacccagc ataaaaacgc tcaggccta                409
```

<210> SEQ ID NO 33
<211> LENGTH: 625
<212> TYPE: DNA
<213> ORGANISM: Homo sapiens

<400> SEQUENCE: 33

```
tgttatgggc caaattgtgc caccccctccc aaatgcatat gtttaaattc taattcccag    60
gacctcctaa tatggctgta tttggagaca ggatctttaa agtggtcgtt gtaggcccag   120
cacagtggct catgcctgta atcccagcac tttgggggac caaggtgggc agattgcttg   180
agcctaggag ttcaaaacca gtctgggcaa catggtgaaa ccccgttgct acaaaaaata   240
caagaattaa ccaggcacgg tggtgcacac ctgtaatccc agctactcag gaggctgagg   300
cgggaggatg cttaagcctg ggaggtggaa gttgcagtga gctgagatca ccactgca    360
ctccagcctg agtgacagag cgagaccctg tctcaaaaac aaaagaagag gaggaggaga   420
ttaggaccca gacacacaga aggagaacca ggtgaagaca cagggagaag aggatcatct   480
acaagccaag acaggaggcc tcagaagaaa ttaaccctgc caacaccttg atcttggaca   540
tccagcctcc ggaactgtga gaaaatgcat tctgttgctg aagccaccca gtcctttgtt   600
atggcagccc cagcaaacta acaca                                         625
```

<210> SEQ ID NO 34
<211> LENGTH: 345
<212> TYPE: DNA
<213> ORGANISM: Homo sapiens

<400> SEQUENCE: 34

```
gggatggttt tttcatgtgt caactttgct aggcaatagt cccctgttac tcaatccaac    60
actaatctag atatttattg aaggtatttt gtagatttcg ttaaagtccg taaccagttg   120
attttaagta agggaaagta tcctagataa tctaggtgaa attgattcaa tatcagttga   180
aaggtcttaa gagtggaatt aaggcttccc tgataaacat gaatttctac ctatagacag   240
cagcttcagc agctttggct tctgctagag agtcccagcc tgcccttcct ggcagcctgc   300
cttatggatt ttggaattgc ctagccatga gccaattcct tgcag                   345
```

<210> SEQ ID NO 35
<211> LENGTH: 23
<212> TYPE: DNA
<213> ORGANISM: Artificial Sequence
<220> FEATURE:
<223> OTHER INFORMATION: Amorce d'amplification

<400> SEQUENCE: 35

```
tgtacaaaac tcaaatggtc ttc                                            23
```

<210> SEQ ID NO 36
<211> LENGTH: 23
<212> TYPE: DNA
<213> ORGANISM: Artificial Sequence
<220> FEATURE:
<223> OTHER INFORMATION: Amorce d'amplification

<400> SEQUENCE: 36

```
atgaccaact tagatttcct tga                                            23
```

<210> SEQ ID NO 37
<211> LENGTH: 22
<212> TYPE: DNA
<213> ORGANISM: Artificial Sequence
<220> FEATURE:
<223> OTHER INFORMATION: Amorce d'amplification

<400> SEQUENCE: 37
gccagagagg cataatgaag ca                                              22

<210> SEQ ID NO 38
<211> LENGTH: 23
<212> TYPE: DNA
<213> ORGANISM: Artificial Sequence
<220> FEATURE:
<223> OTHER INFORMATION: Amorce d'amplification

<400> SEQUENCE: 38
gattctaagc ctccccctca ttt                                             23

<210> SEQ ID NO 39
<211> LENGTH: 22
<212> TYPE: DNA
<213> ORGANISM: Artificial Sequence
<220> FEATURE:
<223> OTHER INFORMATION: Amorce d'amplification

<400> SEQUENCE: 39
tggctcatag ggattccaga ct                                              22

<210> SEQ ID NO 40
<211> LENGTH: 23
<212> TYPE: DNA
<213> ORGANISM: Artificial Sequence
<220> FEATURE:
<223> OTHER INFORMATION: Amorce d'amplification

<400> SEQUENCE: 40
agcaagttgt caagagccaa tct                                             23

<210> SEQ ID NO 41
<211> LENGTH: 20
<212> TYPE: DNA
<213> ORGANISM: Artificial Sequence
<220> FEATURE:
<223> OTHER INFORMATION: Amorce d'amplification

<400> SEQUENCE: 41
cactctagga atcttaggca                                                 20

<210> SEQ ID NO 42
<211> LENGTH: 19
<212> TYPE: DNA
<213> ORGANISM: Artificial Sequence
<220> FEATURE:
<223> OTHER INFORMATION: Amorce d'amplification

<400> SEQUENCE: 42
tgaaaccaat agtccagtg                                                  19

<210> SEQ ID NO 43
<211> LENGTH: 24
<212> TYPE: DNA
<213> ORGANISM: Artificial Sequence
<220> FEATURE:
<223> OTHER INFORMATION: Amorce d'amplification

<400> SEQUENCE: 43
ttctactgtt cactgctatc ctcc                                            24

<210> SEQ ID NO 44

<211> LENGTH: 23
<212> TYPE: DNA
<213> ORGANISM: Artificial Sequence
<220> FEATURE:
<223> OTHER INFORMATION: Amorce d'amplification

<400> SEQUENCE: 44
cctgtggcag cttttttgaag taa				23

<210> SEQ ID NO 45
<211> LENGTH: 22
<212> TYPE: DNA
<213> ORGANISM: Artificial Sequence
<220> FEATURE:
<223> OTHER INFORMATION: Amorce d'amplification

<400> SEQUENCE: 45
agagcagaag aagatggata ct				22

<210> SEQ ID NO 46
<211> LENGTH: 21
<212> TYPE: DNA
<213> ORGANISM: Artificial Sequence
<220> FEATURE:
<223> OTHER INFORMATION: Amorce d'amplification

<400> SEQUENCE: 46
catgagctga catcatccaa t				21

<210> SEQ ID NO 47
<211> LENGTH: 20
<212> TYPE: DNA
<213> ORGANISM: Artificial Sequence
<220> FEATURE:
<223> OTHER INFORMATION: Amorce d'amplification

<400> SEQUENCE: 47
tctgtactgg ttgccccaac				20

<210> SEQ ID NO 48
<211> LENGTH: 23
<212> TYPE: DNA
<213> ORGANISM: Artificial Sequence
<220> FEATURE:
<223> OTHER INFORMATION: Amorce d'amplification

<400> SEQUENCE: 48
cgtgccaggc ctctaatact ttt				23

<210> SEQ ID NO 49
<211> LENGTH: 21
<212> TYPE: DNA
<213> ORGANISM: Artificial Sequence
<220> FEATURE:
<223> OTHER INFORMATION: Amorce d'amplification

<400> SEQUENCE: 49
agggaagacc ccaagatgat g				21

<210> SEQ ID NO 50
<211> LENGTH: 21
<212> TYPE: DNA
<213> ORGANISM: Artificial Sequence
<220> FEATURE:
<223> OTHER INFORMATION: Amorce d'amplification

```
<400> SEQUENCE: 50
catgcaaagt ccaacgagag g                                              21

<210> SEQ ID NO 51
<211> LENGTH: 19
<212> TYPE: DNA
<213> ORGANISM: Artificial Sequence
<220> FEATURE:
<223> OTHER INFORMATION: Amorce d'amplification

<400> SEQUENCE: 51
gggtggctgc atcctatgg                                                 19

<210> SEQ ID NO 52
<211> LENGTH: 24
<212> TYPE: DNA
<213> ORGANISM: Artificial Sequence
<220> FEATURE:
<223> OTHER INFORMATION: Amorce d'amplification

<400> SEQUENCE: 52
ctggtcagga aaaatttgc cttc                                            24

<210> SEQ ID NO 53
<211> LENGTH: 24
<212> TYPE: DNA
<213> ORGANISM: Artificial Sequence
<220> FEATURE:
<223> OTHER INFORMATION: Amorce d'amplification

<400> SEQUENCE: 53
acatgacatt gtctgaactt tggg                                           24

<210> SEQ ID NO 54
<211> LENGTH: 24
<212> TYPE: DNA
<213> ORGANISM: Artificial Sequence
<220> FEATURE:
<223> OTHER INFORMATION: Amorce d'amplification

<400> SEQUENCE: 54
taggaccatg cagatactag tgac                                           24

<210> SEQ ID NO 55
<211> LENGTH: 18
<212> TYPE: DNA
<213> ORGANISM: Artificial Sequence
<220> FEATURE:
<223> OTHER INFORMATION: Amorce d'amplification

<400> SEQUENCE: 55
gaactccaca aaccttga                                                  18

<210> SEQ ID NO 56
<211> LENGTH: 20
<212> TYPE: DNA
<213> ORGANISM: Artificial Sequence
<220> FEATURE:
<223> OTHER INFORMATION: Amorce d'amplification

<400> SEQUENCE: 56
gctagaagct ttggatatct                                                20

<210> SEQ ID NO 57
```

```
<211> LENGTH: 20
<212> TYPE: DNA
<213> ORGANISM: Artificial Sequence
<220> FEATURE:
<223> OTHER INFORMATION: Amorce d'amplification

<400> SEQUENCE: 57
tggctgttac aactttcatg                                              20

<210> SEQ ID NO 58
<211> LENGTH: 19
<212> TYPE: DNA
<213> ORGANISM: Artificial Sequence
<220> FEATURE:
<223> OTHER INFORMATION: Amorce d'amplification

<400> SEQUENCE: 58
tctccctatt ctgagcaca                                               19

<210> SEQ ID NO 59
<211> LENGTH: 25
<212> TYPE: DNA
<213> ORGANISM: Artificial Sequence
<220> FEATURE:
<223> OTHER INFORMATION: Sonde

<400> SEQUENCE: 59
atgaccaact tagatttcct tgagt                                        25

<210> SEQ ID NO 60
<211> LENGTH: 25
<212> TYPE: DNA
<213> ORGANISM: Artificial Sequence
<220> FEATURE:
<223> OTHER INFORMATION: Sonde

<400> SEQUENCE: 60
gtcaagggta aagctgtgaa agttt                                        25

<210> SEQ ID NO 61
<211> LENGTH: 25
<212> TYPE: DNA
<213> ORGANISM: Artificial Sequence
<220> FEATURE:
<223> OTHER INFORMATION: Sonde

<400> SEQUENCE: 61
ggaagaccat ttgagttttg tacac                                        25

<210> SEQ ID NO 62
<211> LENGTH: 25
<212> TYPE: DNA
<213> ORGANISM: Artificial Sequence
<220> FEATURE:
<223> OTHER INFORMATION: Sonde

<400> SEQUENCE: 62
actcaaggaa atctaagttg gtcat                                        25

<210> SEQ ID NO 63
<211> LENGTH: 25
<212> TYPE: DNA
<213> ORGANISM: Artificial Sequence
<220> FEATURE:
<223> OTHER INFORMATION: Sonde
```

<400> SEQUENCE: 63
aaactttcac agctttaccc ttgac                                    25

<210> SEQ ID NO 64
<211> LENGTH: 25
<212> TYPE: DNA
<213> ORGANISM: Artificial Sequence
<220> FEATURE:
<223> OTHER INFORMATION: Sonde

<400> SEQUENCE: 64
gtgtacaaaa ctcaaatggt cttcc                                    25

<210> SEQ ID NO 65
<211> LENGTH: 25
<212> TYPE: DNA
<213> ORGANISM: Artificial Sequence
<220> FEATURE:
<223> OTHER INFORMATION: Sonde

<400> SEQUENCE: 65
gaagatatgg gccagaactt gtata                                    25

<210> SEQ ID NO 66
<211> LENGTH: 25
<212> TYPE: DNA
<213> ORGANISM: Artificial Sequence
<220> FEATURE:
<223> OTHER INFORMATION: Sonde

<400> SEQUENCE: 66
caggacctga gttaagccaa gaata                                    25

<210> SEQ ID NO 67
<211> LENGTH: 25
<212> TYPE: DNA
<213> ORGANISM: Artificial Sequence
<220> FEATURE:
<223> OTHER INFORMATION: Sonde

<400> SEQUENCE: 67
acctgagtta agccaagaat acagt                                    25

<210> SEQ ID NO 68
<211> LENGTH: 25
<212> TYPE: DNA
<213> ORGANISM: Artificial Sequence
<220> FEATURE:
<223> OTHER INFORMATION: Sonde

<400> SEQUENCE: 68
tatacaagtt ctggcccata tcttc                                    25

<210> SEQ ID NO 69
<211> LENGTH: 25
<212> TYPE: DNA
<213> ORGANISM: Artificial Sequence
<220> FEATURE:
<223> OTHER INFORMATION: Sonde

<400> SEQUENCE: 69
tattcttggc ttaactcagg tcctg                                    25

<210> SEQ ID NO 70

```
<211> LENGTH: 25
<212> TYPE: DNA
<213> ORGANISM: Artificial Sequence
<220> FEATURE:
<223> OTHER INFORMATION: Sonde

<400> SEQUENCE: 70
actgtattct tggcttaact caggt                                    25

<210> SEQ ID NO 71
<211> LENGTH: 25
<212> TYPE: DNA
<213> ORGANISM: Artificial Sequence
<220> FEATURE:
<223> OTHER INFORMATION: Sonde

<400> SEQUENCE: 71
gtaagattct aagcctcccc ctcat                                    25

<210> SEQ ID NO 72
<211> LENGTH: 25
<212> TYPE: DNA
<213> ORGANISM: Artificial Sequence
<220> FEATURE:
<223> OTHER INFORMATION: Sonde

<400> SEQUENCE: 72
gattctaagc ctcccccctca tttaa                                   25

<210> SEQ ID NO 73
<211> LENGTH: 25
<212> TYPE: DNA
<213> ORGANISM: Artificial Sequence
<220> FEATURE:
<223> OTHER INFORMATION: Sonde

<400> SEQUENCE: 73
ctaagcctcc ccctcattta aagga                                    25

<210> SEQ ID NO 74
<211> LENGTH: 25
<212> TYPE: DNA
<213> ORGANISM: Artificial Sequence
<220> FEATURE:
<223> OTHER INFORMATION: Sonde

<400> SEQUENCE: 74
atgaggggga ggcttagaat cttac                                    25

<210> SEQ ID NO 75
<211> LENGTH: 25
<212> TYPE: DNA
<213> ORGANISM: Artificial Sequence
<220> FEATURE:
<223> OTHER INFORMATION: Sonde

<400> SEQUENCE: 75
ttaaatgagg gggaggctta gaatc                                    25

<210> SEQ ID NO 76
<211> LENGTH: 25
<212> TYPE: DNA
<213> ORGANISM: Artificial Sequence
<220> FEATURE:
<223> OTHER INFORMATION: Sonde
```

```
<400> SEQUENCE: 76
tcctttaaat gagggggagg cttag                               25

<210> SEQ ID NO 77
<211> LENGTH: 25
<212> TYPE: DNA
<213> ORGANISM: Artificial Sequence
<220> FEATURE:
<223> OTHER INFORMATION: Sonde

<400> SEQUENCE: 77
atggctcata gggattccag actcc                               25

<210> SEQ ID NO 78
<211> LENGTH: 25
<212> TYPE: DNA
<213> ORGANISM: Artificial Sequence
<220> FEATURE:
<223> OTHER INFORMATION: Sonde

<400> SEQUENCE: 78
ggctcatagg gattccagac tccca                               25

<210> SEQ ID NO 79
<211> LENGTH: 25
<212> TYPE: DNA
<213> ORGANISM: Artificial Sequence
<220> FEATURE:
<223> OTHER INFORMATION: Sonde

<400> SEQUENCE: 79
ctcataggga ttccagactc ccatt                               25

<210> SEQ ID NO 80
<211> LENGTH: 25
<212> TYPE: DNA
<213> ORGANISM: Artificial Sequence
<220> FEATURE:
<223> OTHER INFORMATION: Sonde

<400> SEQUENCE: 80
ggagtctgga atccctatga gccat                               25

<210> SEQ ID NO 81
<211> LENGTH: 25
<212> TYPE: DNA
<213> ORGANISM: Artificial Sequence
<220> FEATURE:
<223> OTHER INFORMATION: Sonde

<400> SEQUENCE: 81
tgggagtctg gaatccctat gagcc                               25

<210> SEQ ID NO 82
<211> LENGTH: 25
<212> TYPE: DNA
<213> ORGANISM: Artificial Sequence
<220> FEATURE:
<223> OTHER INFORMATION: Sonde

<400> SEQUENCE: 82
aatgggagtc tggaatccct atgag                               25

<210> SEQ ID NO 83
```

```
<211> LENGTH: 25
<212> TYPE: DNA
<213> ORGANISM: Artificial Sequence
<220> FEATURE:
<223> OTHER INFORMATION: Sonde

<400> SEQUENCE: 83
tgaaaccaat agtccagtgg tggcc                                          25

<210> SEQ ID NO 84
<211> LENGTH: 25
<212> TYPE: DNA
<213> ORGANISM: Artificial Sequence
<220> FEATURE:
<223> OTHER INFORMATION: Sonde

<400> SEQUENCE: 84
ttccagtgat ttagataaaa tccct                                          25

<210> SEQ ID NO 85
<211> LENGTH: 25
<212> TYPE: DNA
<213> ORGANISM: Artificial Sequence
<220> FEATURE:
<223> OTHER INFORMATION: Sonde

<400> SEQUENCE: 85
tttctgccta agattcctag agtgc                                          25

<210> SEQ ID NO 86
<211> LENGTH: 25
<212> TYPE: DNA
<213> ORGANISM: Artificial Sequence
<220> FEATURE:
<223> OTHER INFORMATION: Sonde

<400> SEQUENCE: 86
ggccaccact ggactattgg tttca                                          25

<210> SEQ ID NO 87
<211> LENGTH: 25
<212> TYPE: DNA
<213> ORGANISM: Artificial Sequence
<220> FEATURE:
<223> OTHER INFORMATION: Sonde

<400> SEQUENCE: 87
agggatttta tctaaatcac tggaa                                          25

<210> SEQ ID NO 88
<211> LENGTH: 25
<212> TYPE: DNA
<213> ORGANISM: Artificial Sequence
<220> FEATURE:
<223> OTHER INFORMATION: Sonde

<400> SEQUENCE: 88
gcactctagg aatcttaggc agaaa                                          25

<210> SEQ ID NO 89
<211> LENGTH: 25
<212> TYPE: DNA
<213> ORGANISM: Artificial Sequence
<220> FEATURE:
<223> OTHER INFORMATION: Sonde
```

```
<400> SEQUENCE: 89
ctgtggcagc tttttgaagt aagga                                         25

<210> SEQ ID NO 90
<211> LENGTH: 25
<212> TYPE: DNA
<213> ORGANISM: Artificial Sequence
<220> FEATURE:
<223> OTHER INFORMATION: Sonde

<400> SEQUENCE: 90
atggttagtg cagagtaaag tttgg                                         25

<210> SEQ ID NO 91
<211> LENGTH: 25
<212> TYPE: DNA
<213> ORGANISM: Artificial Sequence
<220> FEATURE:
<223> OTHER INFORMATION: Sonde

<400> SEQUENCE: 91
aggatagcag tgaacagtag aatgg                                         25

<210> SEQ ID NO 92
<211> LENGTH: 25
<212> TYPE: DNA
<213> ORGANISM: Artificial Sequence
<220> FEATURE:
<223> OTHER INFORMATION: Sonde

<400> SEQUENCE: 92
tccttacttc aaaaagctgc cacag                                         25

<210> SEQ ID NO 93
<211> LENGTH: 25
<212> TYPE: DNA
<213> ORGANISM: Artificial Sequence
<220> FEATURE:
<223> OTHER INFORMATION: Sonde

<400> SEQUENCE: 93
ccaaacttta ctctgcacta accat                                         25

<210> SEQ ID NO 94
<211> LENGTH: 25
<212> TYPE: DNA
<213> ORGANISM: Artificial Sequence
<220> FEATURE:
<223> OTHER INFORMATION: Sonde

<400> SEQUENCE: 94
ccattctact gttcactgct atcct                                         25

<210> SEQ ID NO 95
<211> LENGTH: 25
<212> TYPE: DNA
<213> ORGANISM: Artificial Sequence
<220> FEATURE:
<223> OTHER INFORMATION: Sonde

<400> SEQUENCE: 95
agatccaaca tgagctgaca tcatc                                         25

<210> SEQ ID NO 96
```

```
<211> LENGTH: 25
<212> TYPE: DNA
<213> ORGANISM: Artificial Sequence
<220> FEATURE:
<223> OTHER INFORMATION: Sonde

<400> SEQUENCE: 96
gatgatgtca gctcatgttg gatct                                25

<210> SEQ ID NO 97
<211> LENGTH: 25
<212> TYPE: DNA
<213> ORGANISM: Artificial Sequence
<220> FEATURE:
<223> OTHER INFORMATION: Sonde

<400> SEQUENCE: 97
gaggttgggg caaccagtac agatt                                25

<210> SEQ ID NO 98
<211> LENGTH: 25
<212> TYPE: DNA
<213> ORGANISM: Artificial Sequence
<220> FEATURE:
<223> OTHER INFORMATION: Sonde

<400> SEQUENCE: 98
aatctgtact ggttgcccca acctc                                25

<210> SEQ ID NO 99
<211> LENGTH: 25
<212> TYPE: DNA
<213> ORGANISM: Artificial Sequence
<220> FEATURE:
<223> OTHER INFORMATION: Sonde

<400> SEQUENCE: 99
ccccaagatg atggactctg gtgat                                25

<210> SEQ ID NO 100
<211> LENGTH: 25
<212> TYPE: DNA
<213> ORGANISM: Artificial Sequence
<220> FEATURE:
<223> OTHER INFORMATION: Sonde

<400> SEQUENCE: 100
cactgccatc actttgggaa agact                                25

<210> SEQ ID NO 101
<211> LENGTH: 25
<212> TYPE: DNA
<213> ORGANISM: Artificial Sequence
<220> FEATURE:
<223> OTHER INFORMATION: Sonde

<400> SEQUENCE: 101
aagcagcctc tcgttggact ttgca                                25

<210> SEQ ID NO 102
<211> LENGTH: 25
<212> TYPE: DNA
<213> ORGANISM: Artificial Sequence
<220> FEATURE:
<223> OTHER INFORMATION: Sonde
```

```
<400> SEQUENCE: 102
atcaccagag tccatcatct tgggg                                              25

<210> SEQ ID NO 103
<211> LENGTH: 25
<212> TYPE: DNA
<213> ORGANISM: Artificial Sequence
<220> FEATURE:
<223> OTHER INFORMATION: Sonde

<400> SEQUENCE: 103
agtctttccc aaagtgatgg cagtg                                              25

<210> SEQ ID NO 104
<211> LENGTH: 25
<212> TYPE: DNA
<213> ORGANISM: Artificial Sequence
<220> FEATURE:
<223> OTHER INFORMATION: Sonde

<400> SEQUENCE: 104
tgcaaagtcc aacgagaggc tgctt                                              25

<210> SEQ ID NO 105
<211> LENGTH: 25
<212> TYPE: DNA
<213> ORGANISM: Artificial Sequence
<220> FEATURE:
<223> OTHER INFORMATION: Sonde

<400> SEQUENCE: 105
gagggcagtt tggaacagtt ggaac                                              25

<210> SEQ ID NO 106
<211> LENGTH: 25
<212> TYPE: DNA
<213> ORGANISM: Artificial Sequence
<220> FEATURE:
<223> OTHER INFORMATION: Sonde

<400> SEQUENCE: 106
tgagagacga ttatctggaa gaaga                                              25

<210> SEQ ID NO 107
<211> LENGTH: 25
<212> TYPE: DNA
<213> ORGANISM: Artificial Sequence
<220> FEATURE:
<223> OTHER INFORMATION: Sonde

<400> SEQUENCE: 107
tcacagcttg agaatgtggt aggag                                              25

<210> SEQ ID NO 108
<211> LENGTH: 25
<212> TYPE: DNA
<213> ORGANISM: Artificial Sequence
<220> FEATURE:
<223> OTHER INFORMATION: Sonde

<400> SEQUENCE: 108
ggaatggggg gcatggaatt aaagc                                              25

<210> SEQ ID NO 109
```

```
<211> LENGTH: 25
<212> TYPE: DNA
<213> ORGANISM: Artificial Sequence
<220> FEATURE:
<223> OTHER INFORMATION: Sonde

<400> SEQUENCE: 109
gttccaactg ttccaaactg ccctc                                    25

<210> SEQ ID NO 110
<211> LENGTH: 25
<212> TYPE: DNA
<213> ORGANISM: Artificial Sequence
<220> FEATURE:
<223> OTHER INFORMATION: Sonde

<400> SEQUENCE: 110
tcttcttcca gataatcgtc tctca                                    25

<210> SEQ ID NO 111
<211> LENGTH: 25
<212> TYPE: DNA
<213> ORGANISM: Artificial Sequence
<220> FEATURE:
<223> OTHER INFORMATION: Sonde

<400> SEQUENCE: 111
ctcctaccac attctcaagc tgtga                                    25

<210> SEQ ID NO 112
<211> LENGTH: 25
<212> TYPE: DNA
<213> ORGANISM: Artificial Sequence
<220> FEATURE:
<223> OTHER INFORMATION: Sonde

<400> SEQUENCE: 112
gctttaattc catgcccccc attcc                                    25

<210> SEQ ID NO 113
<211> LENGTH: 25
<212> TYPE: DNA
<213> ORGANISM: Artificial Sequence
<220> FEATURE:
<223> OTHER INFORMATION: Sonde

<400> SEQUENCE: 113
agtccctaac tgtctgcaaa cccac                                    25

<210> SEQ ID NO 114
<211> LENGTH: 25
<212> TYPE: DNA
<213> ORGANISM: Artificial Sequence
<220> FEATURE:
<223> OTHER INFORMATION: Sonde

<400> SEQUENCE: 114
actgtctgca aacccacaat ggacc                                    25

<210> SEQ ID NO 115
<211> LENGTH: 25
<212> TYPE: DNA
<213> ORGANISM: Artificial Sequence
<220> FEATURE:
<223> OTHER INFORMATION: Sonde
```

```
<400> SEQUENCE: 115
caatggacct gttgcatgtg taaga                                    25

<210> SEQ ID NO 116
<211> LENGTH: 25
<212> TYPE: DNA
<213> ORGANISM: Artificial Sequence
<220> FEATURE:
<223> OTHER INFORMATION: Sonde

<400> SEQUENCE: 116
gtgggtttgc agacagttag ggact                                    25

<210> SEQ ID NO 117
<211> LENGTH: 25
<212> TYPE: DNA
<213> ORGANISM: Artificial Sequence
<220> FEATURE:
<223> OTHER INFORMATION: Sonde

<400> SEQUENCE: 117
ggtccattgt gggtttgcag acagt                                    25

<210> SEQ ID NO 118
<211> LENGTH: 25
<212> TYPE: DNA
<213> ORGANISM: Artificial Sequence
<220> FEATURE:
<223> OTHER INFORMATION: Sonde

<400> SEQUENCE: 118
tcttacacat gcaacaggtc cattg                                    25

<210> SEQ ID NO 119
<211> LENGTH: 25
<212> TYPE: DNA
<213> ORGANISM: Artificial Sequence
<220> FEATURE:
<223> OTHER INFORMATION: Sonde

<400> SEQUENCE: 119
ctgcatccta tggtgtttct acatg                                    25

<210> SEQ ID NO 120
<211> LENGTH: 25
<212> TYPE: DNA
<213> ORGANISM: Artificial Sequence
<220> FEATURE:
<223> OTHER INFORMATION: Sonde

<400> SEQUENCE: 120
ataatctttt ccggcatgtt ggtat                                    25

<210> SEQ ID NO 121
<211> LENGTH: 25
<212> TYPE: DNA
<213> ORGANISM: Artificial Sequence
<220> FEATURE:
<223> OTHER INFORMATION: Sonde

<400> SEQUENCE: 121
taaagatagt gtttcctatt gtgtc                                    25

<210> SEQ ID NO 122
```

```
<211> LENGTH: 25
<212> TYPE: DNA
<213> ORGANISM: Artificial Sequence
<220> FEATURE:
<223> OTHER INFORMATION: Sonde

<400> SEQUENCE: 122
catgtagaaa caccatagga tgcag                                    25

<210> SEQ ID NO 123
<211> LENGTH: 25
<212> TYPE: DNA
<213> ORGANISM: Artificial Sequence
<220> FEATURE:
<223> OTHER INFORMATION: Sonde

<400> SEQUENCE: 123
ataccaacat gccggaaaag attat                                    25

<210> SEQ ID NO 124
<211> LENGTH: 25
<212> TYPE: DNA
<213> ORGANISM: Artificial Sequence
<220> FEATURE:
<223> OTHER INFORMATION: Sonde

<400> SEQUENCE: 124
gacacaatag gaaacactat cttta                                    25

<210> SEQ ID NO 125
<211> LENGTH: 25
<212> TYPE: DNA
<213> ORGANISM: Artificial Sequence
<220> FEATURE:
<223> OTHER INFORMATION: Sonde

<400> SEQUENCE: 125
acagagactg caagagtaat gacat                                    25

<210> SEQ ID NO 126
<211> LENGTH: 25
<212> TYPE: DNA
<213> ORGANISM: Artificial Sequence
<220> FEATURE:
<223> OTHER INFORMATION: Sonde

<400> SEQUENCE: 126
tctgaacttt gggaaacaat tatgt                                    25

<210> SEQ ID NO 127
<211> LENGTH: 25
<212> TYPE: DNA
<213> ORGANISM: Artificial Sequence
<220> FEATURE:
<223> OTHER INFORMATION: Sonde

<400> SEQUENCE: 127
actttccagt taatcgaatc aatcc                                    25

<210> SEQ ID NO 128
<211> LENGTH: 25
<212> TYPE: DNA
<213> ORGANISM: Artificial Sequence
<220> FEATURE:
<223> OTHER INFORMATION: Sonde
```

```
<400> SEQUENCE: 128
ttttaaccta gactagttcc aactg                                          25

<210> SEQ ID NO 129
<211> LENGTH: 25
<212> TYPE: DNA
<213> ORGANISM: Artificial Sequence
<220> FEATURE:
<223> OTHER INFORMATION: Sonde

<400> SEQUENCE: 129
gtcactagta tctgcatggt cctaa                                          25

<210> SEQ ID NO 130
<211> LENGTH: 25
<212> TYPE: DNA
<213> ORGANISM: Artificial Sequence
<220> FEATURE:
<223> OTHER INFORMATION: Sonde

<400> SEQUENCE: 130
atgtcattac tcttgcagtc tctgt                                          25

<210> SEQ ID NO 131
<211> LENGTH: 25
<212> TYPE: DNA
<213> ORGANISM: Artificial Sequence
<220> FEATURE:
<223> OTHER INFORMATION: Sonde

<400> SEQUENCE: 131
acataattgt ttcccaaagt tcaga                                          25

<210> SEQ ID NO 132
<211> LENGTH: 25
<212> TYPE: DNA
<213> ORGANISM: Artificial Sequence
<220> FEATURE:
<223> OTHER INFORMATION: Sonde

<400> SEQUENCE: 132
ggattgattc gattaactgg aaagt                                          25

<210> SEQ ID NO 133
<211> LENGTH: 25
<212> TYPE: DNA
<213> ORGANISM: Artificial Sequence
<220> FEATURE:
<223> OTHER INFORMATION: Sonde

<400> SEQUENCE: 133
cagttggaac tagtctaggt taaaa                                          25

<210> SEQ ID NO 134
<211> LENGTH: 25
<212> TYPE: DNA
<213> ORGANISM: Artificial Sequence
<220> FEATURE:
<223> OTHER INFORMATION: Sonde

<400> SEQUENCE: 134
ttaggaccat gcagatacta gtgac                                          25

<210> SEQ ID NO 135
```

```
<211> LENGTH: 25
<212> TYPE: DNA
<213> ORGANISM: Artificial Sequence
<220> FEATURE:
<223> OTHER INFORMATION: Sonde

<400> SEQUENCE: 135
ttattccagt cacctcgagt cattc                                  25

<210> SEQ ID NO 136
<211> LENGTH: 25
<212> TYPE: DNA
<213> ORGANISM: Artificial Sequence
<220> FEATURE:
<223> OTHER INFORMATION: Sonde

<400> SEQUENCE: 136
tcatcctagc cgtcgtagag cagag                                  25

<210> SEQ ID NO 137
<211> LENGTH: 25
<212> TYPE: DNA
<213> ORGANISM: Artificial Sequence
<220> FEATURE:
<223> OTHER INFORMATION: Sonde

<400> SEQUENCE: 137
tgcccttctg actccttgac agtgg                                  25

<210> SEQ ID NO 138
<211> LENGTH: 25
<212> TYPE: DNA
<213> ORGANISM: Artificial Sequence
<220> FEATURE:
<223> OTHER INFORMATION: Sonde

<400> SEQUENCE: 138
gaatgactcg aggtgactgg aataa                                  25

<210> SEQ ID NO 139
<211> LENGTH: 25
<212> TYPE: DNA
<213> ORGANISM: Artificial Sequence
<220> FEATURE:
<223> OTHER INFORMATION: Sonde

<400> SEQUENCE: 139
ctctgctcta cgacggctag gatga                                  25

<210> SEQ ID NO 140
<211> LENGTH: 25
<212> TYPE: DNA
<213> ORGANISM: Artificial Sequence
<220> FEATURE:
<223> OTHER INFORMATION: Sonde

<400> SEQUENCE: 140
ccactgtcaa ggagtcagaa gggca                                  25

<210> SEQ ID NO 141
<211> LENGTH: 25
<212> TYPE: DNA
<213> ORGANISM: Artificial Sequence
<220> FEATURE:
<223> OTHER INFORMATION: Sonde
```

```
<400> SEQUENCE: 141
taagtgggac caagacacaa accaa                                              25

<210> SEQ ID NO 142
<211> LENGTH: 25
<212> TYPE: DNA
<213> ORGANISM: Artificial Sequence
<220> FEATURE:
<223> OTHER INFORMATION: Sonde

<400> SEQUENCE: 142
accaagacac aaaccaacat gcctg                                              25

<210> SEQ ID NO 143
<211> LENGTH: 25
<212> TYPE: DNA
<213> ORGANISM: Artificial Sequence
<220> FEATURE:
<223> OTHER INFORMATION: Sonde

<400> SEQUENCE: 143
ttggtttgtg tcttggtccc actta                                              25

<210> SEQ ID NO 144
<211> LENGTH: 25
<212> TYPE: DNA
<213> ORGANISM: Artificial Sequence
<220> FEATURE:
<223> OTHER INFORMATION: Sonde

<400> SEQUENCE: 144
caggcatgtt ggtttgtgtc ttggt                                              25

<210> SEQ ID NO 145
<211> LENGTH: 25
<212> TYPE: DNA
<213> ORGANISM: Artificial Sequence
<220> FEATURE:
<223> OTHER INFORMATION: Sonde

<400> SEQUENCE: 145
ctgaggtcca tggcttcttt ccttg                                              25

<210> SEQ ID NO 146
<211> LENGTH: 25
<212> TYPE: DNA
<213> ORGANISM: Artificial Sequence
<220> FEATURE:
<223> OTHER INFORMATION: Sonde

<400> SEQUENCE: 146
caaggaaaga agccatggac ctcag                                              25

<210> SEQ ID NO 147
<211> LENGTH: 25
<212> TYPE: DNA
<213> ORGANISM: Artificial Sequence
<220> FEATURE:
<223> OTHER INFORMATION: Sonde

<400> SEQUENCE: 147
cctttgtttt cctactgaca ggtcc                                              25

<210> SEQ ID NO 148
```

```
<211> LENGTH: 25
<212> TYPE: DNA
<213> ORGANISM: Artificial Sequence
<220> FEATURE:
<223> OTHER INFORMATION: Sonde

<400> SEQUENCE: 148
ttcaaaatat ttaactctcc aggct                                        25

<210> SEQ ID NO 149
<211> LENGTH: 25
<212> TYPE: DNA
<213> ORGANISM: Artificial Sequence
<220> FEATURE:
<223> OTHER INFORMATION: Sonde

<400> SEQUENCE: 149
gaggtcacat gactctgttg tggac                                        25

<210> SEQ ID NO 150
<211> LENGTH: 25
<212> TYPE: DNA
<213> ORGANISM: Artificial Sequence
<220> FEATURE:
<223> OTHER INFORMATION: Sonde

<400> SEQUENCE: 150
ggacctgtca gtaggaaaac aaagg                                        25

<210> SEQ ID NO 151
<211> LENGTH: 25
<212> TYPE: DNA
<213> ORGANISM: Artificial Sequence
<220> FEATURE:
<223> OTHER INFORMATION: Sonde

<400> SEQUENCE: 151
agcctggaga gttaaatatt ttgaa                                        25

<210> SEQ ID NO 152
<211> LENGTH: 25
<212> TYPE: DNA
<213> ORGANISM: Artificial Sequence
<220> FEATURE:
<223> OTHER INFORMATION: Sonde

<400> SEQUENCE: 152
gtccacaaca gagtcatgtg acctc                                        25

<210> SEQ ID NO 153
<211> LENGTH: 25
<212> TYPE: DNA
<213> ORGANISM: Artificial Sequence
<220> FEATURE:
<223> OTHER INFORMATION: Sonde

<400> SEQUENCE: 153
cagctgagat ccgttgacgc cagcc                                        25

<210> SEQ ID NO 154
<211> LENGTH: 25
<212> TYPE: DNA
<213> ORGANISM: Artificial Sequence
<220> FEATURE:
<223> OTHER INFORMATION: Sonde
```

```
<400> SEQUENCE: 154
tccgacatgt gggtgaactc agcca                                              25

<210> SEQ ID NO 155
<211> LENGTH: 25
<212> TYPE: DNA
<213> ORGANISM: Artificial Sequence
<220> FEATURE:
<223> OTHER INFORMATION: Sonde

<400> SEQUENCE: 155
ttctcagcca tgtgttttgt gaact                                              25

<210> SEQ ID NO 156
<211> LENGTH: 25
<212> TYPE: DNA
<213> ORGANISM: Artificial Sequence
<220> FEATURE:
<223> OTHER INFORMATION: Sonde

<400> SEQUENCE: 156
ggctggcgtc aacggatctc agctg                                              25

<210> SEQ ID NO 157
<211> LENGTH: 25
<212> TYPE: DNA
<213> ORGANISM: Artificial Sequence
<220> FEATURE:
<223> OTHER INFORMATION: Sonde

<400> SEQUENCE: 157
tggctgagtt cacccacatg tcgga                                              25

<210> SEQ ID NO 158
<211> LENGTH: 25
<212> TYPE: DNA
<213> ORGANISM: Artificial Sequence
<220> FEATURE:
<223> OTHER INFORMATION: Sonde

<400> SEQUENCE: 158
agttcacaaa acacatggct gagaa                                              25

<210> SEQ ID NO 159
<211> LENGTH: 25
<212> TYPE: DNA
<213> ORGANISM: Artificial Sequence
<220> FEATURE:
<223> OTHER INFORMATION: Sonde

<400> SEQUENCE: 159
ttgaggcagg acagaaccag gctcc                                              25

<210> SEQ ID NO 160
<211> LENGTH: 25
<212> TYPE: DNA
<213> ORGANISM: Artificial Sequence
<220> FEATURE:
<223> OTHER INFORMATION: Sonde

<400> SEQUENCE: 160
ggacagaacc aggctcctgt tagtc                                              25

<210> SEQ ID NO 161
```

```
<211> LENGTH: 25
<212> TYPE: DNA
<213> ORGANISM: Artificial Sequence
<220> FEATURE:
<223> OTHER INFORMATION: Sonde

<400> SEQUENCE: 161
agtttactga gcagtgactt tgtgt                                               25

<210> SEQ ID NO 162
<211> LENGTH: 25
<212> TYPE: DNA
<213> ORGANISM: Artificial Sequence
<220> FEATURE:
<223> OTHER INFORMATION: Sonde

<400> SEQUENCE: 162
ggagcctggt tctgtcctgc ctcaa                                               25

<210> SEQ ID NO 163
<211> LENGTH: 25
<212> TYPE: DNA
<213> ORGANISM: Artificial Sequence
<220> FEATURE:
<223> OTHER INFORMATION: Sonde

<400> SEQUENCE: 163
gactaacagg agcctggttc tgtcc                                               25

<210> SEQ ID NO 164
<211> LENGTH: 25
<212> TYPE: DNA
<213> ORGANISM: Artificial Sequence
<220> FEATURE:
<223> OTHER INFORMATION: Sonde

<400> SEQUENCE: 164
acacaaagtc actgctcagt aaact                                               25

<210> SEQ ID NO 165
<211> LENGTH: 25
<212> TYPE: DNA
<213> ORGANISM: Artificial Sequence
<220> FEATURE:
<223> OTHER INFORMATION: Sonde

<400> SEQUENCE: 165
atagggatga tcctgcacga atggc                                               25

<210> SEQ ID NO 166
<211> LENGTH: 25
<212> TYPE: DNA
<213> ORGANISM: Artificial Sequence
<220> FEATURE:
<223> OTHER INFORMATION: Sonde

<400> SEQUENCE: 166
ggatgatcct gcacgaatgg catgg                                               25

<210> SEQ ID NO 167
<211> LENGTH: 25
<212> TYPE: DNA
<213> ORGANISM: Artificial Sequence
<220> FEATURE:
<223> OTHER INFORMATION: Sonde
```

```
<400> SEQUENCE: 167
gccattcgtg caggatcatc cctat                                        25

<210> SEQ ID NO 168
<211> LENGTH: 25
<212> TYPE: DNA
<213> ORGANISM: Artificial Sequence
<220> FEATURE:
<223> OTHER INFORMATION: Sonde

<400> SEQUENCE: 168
ccatgccatt cgtgcaggat catcc                                        25

<210> SEQ ID NO 169
<211> LENGTH: 25
<212> TYPE: DNA
<213> ORGANISM: Artificial Sequence
<220> FEATURE:
<223> OTHER INFORMATION: Sonde

<400> SEQUENCE: 169
agtggacact ttttaggatg tctgc                                        25

<210> SEQ ID NO 170
<211> LENGTH: 25
<212> TYPE: DNA
<213> ORGANISM: Artificial Sequence
<220> FEATURE:
<223> OTHER INFORMATION: Sonde

<400> SEQUENCE: 170
gccctgacat aagagtttgc cagtt                                        25

<210> SEQ ID NO 171
<211> LENGTH: 25
<212> TYPE: DNA
<213> ORGANISM: Artificial Sequence
<220> FEATURE:
<223> OTHER INFORMATION: Sonde

<400> SEQUENCE: 171
cctgtaccca cctttcacca gagct                                        25

<210> SEQ ID NO 172
<211> LENGTH: 25
<212> TYPE: DNA
<213> ORGANISM: Artificial Sequence
<220> FEATURE:
<223> OTHER INFORMATION: Sonde

<400> SEQUENCE: 172
gcagacatcc taaaaagtgt ccact                                        25

<210> SEQ ID NO 173
<211> LENGTH: 25
<212> TYPE: DNA
<213> ORGANISM: Artificial Sequence
<220> FEATURE:
<223> OTHER INFORMATION: Sonde

<400> SEQUENCE: 173
aactggcaaa ctcttatgtc agggc                                        25

<210> SEQ ID NO 174
```

```
<211> LENGTH: 25
<212> TYPE: DNA
<213> ORGANISM: Artificial Sequence
<220> FEATURE:
<223> OTHER INFORMATION: Sonde

<400> SEQUENCE: 174
agctctggtg aaaggtgggt acagg                                    25

<210> SEQ ID NO 175
<211> LENGTH: 25
<212> TYPE: DNA
<213> ORGANISM: Artificial Sequence
<220> FEATURE:
<223> OTHER INFORMATION: Sonde

<400> SEQUENCE: 175
aattgttgga atttgaaagt ggggt                                    25

<210> SEQ ID NO 176
<211> LENGTH: 25
<212> TYPE: DNA
<213> ORGANISM: Artificial Sequence
<220> FEATURE:
<223> OTHER INFORMATION: Sonde

<400> SEQUENCE: 176
accccacttt caaattccaa caatt                                    25

<210> SEQ ID NO 177
<211> LENGTH: 25
<212> TYPE: DNA
<213> ORGANISM: Artificial Sequence
<220> FEATURE:
<223> OTHER INFORMATION: Sonde

<400> SEQUENCE: 177
gtcagcaccg tgcttctcta acttt                                    25

<210> SEQ ID NO 178
<211> LENGTH: 25
<212> TYPE: DNA
<213> ORGANISM: Artificial Sequence
<220> FEATURE:
<223> OTHER INFORMATION: Sonde

<400> SEQUENCE: 178
gcaccgtgct tctctaactt tccac                                    25

<210> SEQ ID NO 179
<211> LENGTH: 25
<212> TYPE: DNA
<213> ORGANISM: Artificial Sequence
<220> FEATURE:
<223> OTHER INFORMATION: Sonde

<400> SEQUENCE: 179
cgtgcttctc taactttcca cctgc                                    25

<210> SEQ ID NO 180
<211> LENGTH: 25
<212> TYPE: DNA
<213> ORGANISM: Artificial Sequence
<220> FEATURE:
<223> OTHER INFORMATION: Sonde
```

```
<400> SEQUENCE: 180
aaagttagag aagcacggtg ctgac                                          25

<210> SEQ ID NO 181
<211> LENGTH: 25
<212> TYPE: DNA
<213> ORGANISM: Artificial Sequence
<220> FEATURE:
<223> OTHER INFORMATION: Sonde

<400> SEQUENCE: 181
gtggaaagtt agagaagcac ggtgc                                          25

<210> SEQ ID NO 182
<211> LENGTH: 25
<212> TYPE: DNA
<213> ORGANISM: Artificial Sequence
<220> FEATURE:
<223> OTHER INFORMATION: Sonde

<400> SEQUENCE: 182
gcaggtggaa agttagagaa gcacg                                          25

<210> SEQ ID NO 183
<211> LENGTH: 25
<212> TYPE: DNA
<213> ORGANISM: Artificial Sequence
<220> FEATURE:
<223> OTHER INFORMATION: Sonde

<400> SEQUENCE: 183
cagcctcgca cctaagaacg ccgtg                                          25

<210> SEQ ID NO 184
<211> LENGTH: 25
<212> TYPE: DNA
<213> ORGANISM: Artificial Sequence
<220> FEATURE:
<223> OTHER INFORMATION: Sonde

<400> SEQUENCE: 184
cagtgagaaa tctgctgggg atgcc                                          25

<210> SEQ ID NO 185
<211> LENGTH: 25
<212> TYPE: DNA
<213> ORGANISM: Artificial Sequence
<220> FEATURE:
<223> OTHER INFORMATION: Sonde

<400> SEQUENCE: 185
gaaagggaca tacctggcag gtgcc                                          25

<210> SEQ ID NO 186
<211> LENGTH: 25
<212> TYPE: DNA
<213> ORGANISM: Artificial Sequence
<220> FEATURE:
<223> OTHER INFORMATION: Sonde

<400> SEQUENCE: 186
cacggcgttc ttaggtgcga ggctg                                          25

<210> SEQ ID NO 187
```

```
<211> LENGTH: 25
<212> TYPE: DNA
<213> ORGANISM: Artificial Sequence
<220> FEATURE:
<223> OTHER INFORMATION: Sonde

<400> SEQUENCE: 187
ggcatcccca gcagatttct cactg                                 25

<210> SEQ ID NO 188
<211> LENGTH: 25
<212> TYPE: DNA
<213> ORGANISM: Artificial Sequence
<220> FEATURE:
<223> OTHER INFORMATION: Sonde

<400> SEQUENCE: 188
ggcacctgcc aggtatgtcc ctttc                                 25

<210> SEQ ID NO 189
<211> LENGTH: 25
<212> TYPE: DNA
<213> ORGANISM: Artificial Sequence
<220> FEATURE:
<223> OTHER INFORMATION: Sonde

<400> SEQUENCE: 189
ggtagagacc gaggcggata tacag                                 25

<210> SEQ ID NO 190
<211> LENGTH: 25
<212> TYPE: DNA
<213> ORGANISM: Artificial Sequence
<220> FEATURE:
<223> OTHER INFORMATION: Sonde

<400> SEQUENCE: 190
gagaccgagg cggatataca ggcct                                 25

<210> SEQ ID NO 191
<211> LENGTH: 25
<212> TYPE: DNA
<213> ORGANISM: Artificial Sequence
<220> FEATURE:
<223> OTHER INFORMATION: Sonde

<400> SEQUENCE: 191
ctgtatatcc gcctcggtct ctacc                                 25

<210> SEQ ID NO 192
<211> LENGTH: 25
<212> TYPE: DNA
<213> ORGANISM: Artificial Sequence
<220> FEATURE:
<223> OTHER INFORMATION: Sonde

<400> SEQUENCE: 192
aggcctgtat atccgcctcg gtctc                                 25

<210> SEQ ID NO 193
<211> LENGTH: 25
<212> TYPE: DNA
<213> ORGANISM: Artificial Sequence
<220> FEATURE:
<223> OTHER INFORMATION: Sonde
```

```
<400> SEQUENCE: 193
tatactgggg cccaattcta cagac                                          25

<210> SEQ ID NO 194
<211> LENGTH: 25
<212> TYPE: DNA
<213> ORGANISM: Artificial Sequence
<220> FEATURE:
<223> OTHER INFORMATION: Sonde

<400> SEQUENCE: 194
cagacattac ttctttgcca gttgg                                          25

<210> SEQ ID NO 195
<211> LENGTH: 25
<212> TYPE: DNA
<213> ORGANISM: Artificial Sequence
<220> FEATURE:
<223> OTHER INFORMATION: Sonde

<400> SEQUENCE: 195
gacacattgc aagtctggaa gagga                                          25

<210> SEQ ID NO 196
<211> LENGTH: 25
<212> TYPE: DNA
<213> ORGANISM: Artificial Sequence
<220> FEATURE:
<223> OTHER INFORMATION: Sonde

<400> SEQUENCE: 196
gtctgtagaa ttgggcccca gtata                                          25

<210> SEQ ID NO 197
<211> LENGTH: 25
<212> TYPE: DNA
<213> ORGANISM: Artificial Sequence
<220> FEATURE:
<223> OTHER INFORMATION: Sonde

<400> SEQUENCE: 197
gtctgtagaa ttgggcccca gtata                                          25

<210> SEQ ID NO 198
<211> LENGTH: 25
<212> TYPE: DNA
<213> ORGANISM: Artificial Sequence
<220> FEATURE:
<223> OTHER INFORMATION: Sonde

<400> SEQUENCE: 198
tcctcttcca gacttgcaat gtgtc                                          25

<210> SEQ ID NO 199
<211> LENGTH: 25
<212> TYPE: DNA
<213> ORGANISM: Artificial Sequence
<220> FEATURE:
<223> OTHER INFORMATION: Sonde

<400> SEQUENCE: 199
catgatcctg ggtgaagcca tgtgt                                          25

<210> SEQ ID NO 200
```

```
<211> LENGTH: 25
<212> TYPE: DNA
<213> ORGANISM: Artificial Sequence
<220> FEATURE:
<223> OTHER INFORMATION: Sonde

<400> SEQUENCE: 200
tgtgtctgag gatgaaaggg gatgc                               25

<210> SEQ ID NO 201
<211> LENGTH: 25
<212> TYPE: DNA
<213> ORGANISM: Artificial Sequence
<220> FEATURE:
<223> OTHER INFORMATION: Sonde

<400> SEQUENCE: 201
cagattgatg tgacatgtgg cacct                               25

<210> SEQ ID NO 202
<211> LENGTH: 25
<212> TYPE: DNA
<213> ORGANISM: Artificial Sequence
<220> FEATURE:
<223> OTHER INFORMATION: Sonde

<400> SEQUENCE: 202
acacatggct tcacccagga tcatg                               25

<210> SEQ ID NO 203
<211> LENGTH: 25
<212> TYPE: DNA
<213> ORGANISM: Artificial Sequence
<220> FEATURE:
<223> OTHER INFORMATION: Sonde

<400> SEQUENCE: 203
gcatcccctt tcatcctcag acaca                               25

<210> SEQ ID NO 204
<211> LENGTH: 25
<212> TYPE: DNA
<213> ORGANISM: Artificial Sequence
<220> FEATURE:
<223> OTHER INFORMATION: Sonde

<400> SEQUENCE: 204
aggtgccaca tgtcacatca atctg                               25

<210> SEQ ID NO 205
<211> LENGTH: 25
<212> TYPE: DNA
<213> ORGANISM: Artificial Sequence
<220> FEATURE:
<223> OTHER INFORMATION: Sonde

<400> SEQUENCE: 205
agagggagca cggtcccagt acacc                               25

<210> SEQ ID NO 206
<211> LENGTH: 25
<212> TYPE: DNA
<213> ORGANISM: Artificial Sequence
<220> FEATURE:
<223> OTHER INFORMATION: Sonde
```

```
<400> SEQUENCE: 206
cacggtccca gtacaccttg agtgt                                          25

<210> SEQ ID NO 207
<211> LENGTH: 25
<212> TYPE: DNA
<213> ORGANISM: Artificial Sequence
<220> FEATURE:
<223> OTHER INFORMATION: Sonde

<400> SEQUENCE: 207
tgttacggct gtcccaggaa aggaa                                          25

<210> SEQ ID NO 208
<211> LENGTH: 25
<212> TYPE: DNA
<213> ORGANISM: Artificial Sequence
<220> FEATURE:
<223> OTHER INFORMATION: Sonde

<400> SEQUENCE: 208
ggtgtactgg gaccgtgctc cctct                                          25

<210> SEQ ID NO 209
<211> LENGTH: 25
<212> TYPE: DNA
<213> ORGANISM: Artificial Sequence
<220> FEATURE:
<223> OTHER INFORMATION: Sonde

<400> SEQUENCE: 209
acactcaagg tgtactggga ccgtg                                          25

<210> SEQ ID NO 210
<211> LENGTH: 25
<212> TYPE: DNA
<213> ORGANISM: Artificial Sequence
<220> FEATURE:
<223> OTHER INFORMATION: Sonde

<400> SEQUENCE: 210
ttcctttcct gggacagccg taaca                                          25

<210> SEQ ID NO 211
<211> LENGTH: 25
<212> TYPE: DNA
<213> ORGANISM: Artificial Sequence
<220> FEATURE:
<223> OTHER INFORMATION: Sonde

<400> SEQUENCE: 211
actaagagca acagcctgag gctaa                                          25

<210> SEQ ID NO 212
<211> LENGTH: 25
<212> TYPE: DNA
<213> ORGANISM: Artificial Sequence
<220> FEATURE:
<223> OTHER INFORMATION: Sonde

<400> SEQUENCE: 212
ggctcaccgg aaacaggctg aatgt                                          25

<210> SEQ ID NO 213
```

```
<211> LENGTH: 25
<212> TYPE: DNA
<213> ORGANISM: Artificial Sequence
<220> FEATURE:
<223> OTHER INFORMATION: Sonde

<400> SEQUENCE: 213
gagacaccag atgaccgctt ggtct                                              25

<210> SEQ ID NO 214
<211> LENGTH: 25
<212> TYPE: DNA
<213> ORGANISM: Artificial Sequence
<220> FEATURE:
<223> OTHER INFORMATION: Sonde

<400> SEQUENCE: 214
cagcttccct agaattatac accag                                              25

<210> SEQ ID NO 215
<211> LENGTH: 25
<212> TYPE: DNA
<213> ORGANISM: Artificial Sequence
<220> FEATURE:
<223> OTHER INFORMATION: Sonde

<400> SEQUENCE: 215
tactgaacag gttacttcaa cttgc                                              25

<210> SEQ ID NO 216
<211> LENGTH: 25
<212> TYPE: DNA
<213> ORGANISM: Artificial Sequence
<220> FEATURE:
<223> OTHER INFORMATION: Sonde

<400> SEQUENCE: 216
ttgtaaaaat ataaacgtga ggcaa                                              25

<210> SEQ ID NO 217
<211> LENGTH: 25
<212> TYPE: DNA
<213> ORGANISM: Artificial Sequence
<220> FEATURE:
<223> OTHER INFORMATION: Sonde

<400> SEQUENCE: 217
ttagcctcag gctgttgctc ttagt                                              25

<210> SEQ ID NO 218
<211> LENGTH: 25
<212> TYPE: DNA
<213> ORGANISM: Artificial Sequence
<220> FEATURE:
<223> OTHER INFORMATION: Sonde

<400> SEQUENCE: 218
acattcagcc tgtttccggt gagcc                                              25

<210> SEQ ID NO 219
<211> LENGTH: 25
<212> TYPE: DNA
<213> ORGANISM: Artificial Sequence
<220> FEATURE:
<223> OTHER INFORMATION: Sonde
```

-continued

<400> SEQUENCE: 219
agaccaagcg gtcatctggt gtctc                                    25

<210> SEQ ID NO 220
<211> LENGTH: 25
<212> TYPE: DNA
<213> ORGANISM: Artificial Sequence
<220> FEATURE:
<223> OTHER INFORMATION: Sonde

<400> SEQUENCE: 220
ctggtgtata attctaggga agctg                                    25

<210> SEQ ID NO 221
<211> LENGTH: 25
<212> TYPE: DNA
<213> ORGANISM: Artificial Sequence
<220> FEATURE:
<223> OTHER INFORMATION: Sonde

<400> SEQUENCE: 221
gcaagttgaa gtaacctgtt cagta                                    25

<210> SEQ ID NO 222
<211> LENGTH: 25
<212> TYPE: DNA
<213> ORGANISM: Artificial Sequence
<220> FEATURE:
<223> OTHER INFORMATION: Sonde

<400> SEQUENCE: 222
ttgcctcacg tttatatttt tacaa                                    25

<210> SEQ ID NO 223
<211> LENGTH: 25
<212> TYPE: DNA
<213> ORGANISM: Artificial Sequence
<220> FEATURE:
<223> OTHER INFORMATION: Sonde

<400> SEQUENCE: 223
gatgacagtt aagaccctag gttgc                                    25

<210> SEQ ID NO 224
<211> LENGTH: 25
<212> TYPE: DNA
<213> ORGANISM: Artificial Sequence
<220> FEATURE:
<223> OTHER INFORMATION: Sonde

<400> SEQUENCE: 224
caatctcaag tctgatgact tgtta                                    25

<210> SEQ ID NO 225
<211> LENGTH: 25
<212> TYPE: DNA
<213> ORGANISM: Artificial Sequence
<220> FEATURE:
<223> OTHER INFORMATION: Sonde

<400> SEQUENCE: 225
agacccatca ttgctagcag actat                                    25

<210> SEQ ID NO 226

```
<211> LENGTH: 25
<212> TYPE: DNA
<213> ORGANISM: Artificial Sequence
<220> FEATURE:
<223> OTHER INFORMATION: Sonde

<400> SEQUENCE: 226
aaggatggga aatgctcagg tcacg                                              25

<210> SEQ ID NO 227
<211> LENGTH: 25
<212> TYPE: DNA
<213> ORGANISM: Artificial Sequence
<220> FEATURE:
<223> OTHER INFORMATION: Sonde

<400> SEQUENCE: 227
agggctcatc cactaacccc ctgaa                                              25

<210> SEQ ID NO 228
<211> LENGTH: 25
<212> TYPE: DNA
<213> ORGANISM: Artificial Sequence
<220> FEATURE:
<223> OTHER INFORMATION: Sonde

<400> SEQUENCE: 228
gaaatggata cccttgggtt caact                                              25

<210> SEQ ID NO 229
<211> LENGTH: 25
<212> TYPE: DNA
<213> ORGANISM: Artificial Sequence
<220> FEATURE:
<223> OTHER INFORMATION: Sonde

<400> SEQUENCE: 229
gcaacctagg gtcttaactg tcatc                                              25

<210> SEQ ID NO 230
<211> LENGTH: 25
<212> TYPE: DNA
<213> ORGANISM: Artificial Sequence
<220> FEATURE:
<223> OTHER INFORMATION: Sonde

<400> SEQUENCE: 230
taacaagtca tcagacttga gattg                                              25

<210> SEQ ID NO 231
<211> LENGTH: 25
<212> TYPE: DNA
<213> ORGANISM: Artificial Sequence
<220> FEATURE:
<223> OTHER INFORMATION: Sonde

<400> SEQUENCE: 231
atagtctgct agcaatgatg ggtct                                              25

<210> SEQ ID NO 232
<211> LENGTH: 25
<212> TYPE: DNA
<213> ORGANISM: Artificial Sequence
<220> FEATURE:
<223> OTHER INFORMATION: Sonde
```

```
<400> SEQUENCE: 232
cgtgacctga gcatttccca tcctt                                        25

<210> SEQ ID NO 233
<211> LENGTH: 25
<212> TYPE: DNA
<213> ORGANISM: Artificial Sequence
<220> FEATURE:
<223> OTHER INFORMATION: Sonde

<400> SEQUENCE: 233 ttcaggggt tagtggatga gccct                                         25

<210> SEQ ID NO 234
<211> LENGTH: 25
<212> TYPE: DNA
<213> ORGANISM: Artificial Sequence
<220> FEATURE:
<223> OTHER INFORMATION: Sonde

<400> SEQUENCE: 234
agttgaaccc aagggtatcc atttc                                        25

<210> SEQ ID NO 235
<211> LENGTH: 25
<212> TYPE: DNA
<213> ORGANISM: Artificial Sequence
<220> FEATURE:
<223> OTHER INFORMATION: Sonde

<400> SEQUENCE: 235
gtgccataac gacaattaaa ttttt                                        25

<210> SEQ ID NO 236
<211> LENGTH: 25
<212> TYPE: DNA
<213> ORGANISM: Artificial Sequence
<220> FEATURE:
<223> OTHER INFORMATION: Sonde

<400> SEQUENCE: 236
agtcttttgt tatctatgga ggact                                        25

<210> SEQ ID NO 237
<211> LENGTH: 24
<212> TYPE: DNA
<213> ORGANISM: Artificial Sequence
<220> FEATURE:
<223> OTHER INFORMATION: Sonde

<400> SEQUENCE: 237
gttgtgttaa agtttctaat tacg                                         24

<210> SEQ ID NO 238
<211> LENGTH: 25
<212> TYPE: DNA
<213> ORGANISM: Artificial Sequence
<220> FEATURE:
<223> OTHER INFORMATION: Sonde

<400> SEQUENCE: 238
gtaactttgg gaccaaaaca atgaa                                        25

<210> SEQ ID NO 239
```

```
<211> LENGTH: 25
<212> TYPE: DNA
<213> ORGANISM: Artificial Sequence
<220> FEATURE:
<223> OTHER INFORMATION: Sonde

<400> SEQUENCE: 239
tcataagcct actaatccgg gatca                              25

<210> SEQ ID NO 240
<211> LENGTH: 25
<212> TYPE: DNA
<213> ORGANISM: Artificial Sequence
<220> FEATURE:
<223> OTHER INFORMATION: Sonde

<400> SEQUENCE: 240
gggacaagaa ctaattccac aggag                              25

<210> SEQ ID NO 241
<211> LENGTH: 25
<212> TYPE: DNA
<213> ORGANISM: Artificial Sequence
<220> FEATURE:
<223> OTHER INFORMATION: Sonde

<400> SEQUENCE: 241
aaaaatttaa ttgtcgttat ggcac                              25

<210> SEQ ID NO 242
<211> LENGTH: 25
<212> TYPE: DNA
<213> ORGANISM: Artificial Sequence
<220> FEATURE:
<223> OTHER INFORMATION: Sonde

<400> SEQUENCE: 242
agtcctccat agataacaaa agact                              25

<210> SEQ ID NO 243
<211> LENGTH: 25
<212> TYPE: DNA
<213> ORGANISM: Artificial Sequence
<220> FEATURE:
<223> OTHER INFORMATION: Sonde

<400> SEQUENCE: 243
acgtaattag aaactttaac acaac                              25

<210> SEQ ID NO 244
<211> LENGTH: 25
<212> TYPE: DNA
<213> ORGANISM: Artificial Sequence
<220> FEATURE:
<223> OTHER INFORMATION: Sonde

<400> SEQUENCE: 244
ttcattgttt tggtcccaaa gttac                              25

<210> SEQ ID NO 245
<211> LENGTH: 25
<212> TYPE: DNA
<213> ORGANISM: Artificial Sequence
<220> FEATURE:
<223> OTHER INFORMATION: Sonde
```

<400> SEQUENCE: 245
tgatcccgga ttagtaggct tatga                                              25

<210> SEQ ID NO 246
<211> LENGTH: 25
<212> TYPE: DNA
<213> ORGANISM: Artificial Sequence
<220> FEATURE:
<223> OTHER INFORMATION: Sonde

<400> SEQUENCE: 246
ctcctgtgga attagttctt gtccc                                              25

<210> SEQ ID NO 247
<211> LENGTH: 25
<212> TYPE: DNA
<213> ORGANISM: Artificial Sequence
<220> FEATURE:
<223> OTHER INFORMATION: Sonde

<400> SEQUENCE: 247
gccctttctt gaggtctggg tctgc                                              25

<210> SEQ ID NO 248
<211> LENGTH: 25
<212> TYPE: DNA
<213> ORGANISM: Artificial Sequence
<220> FEATURE:
<223> OTHER INFORMATION: Sonde

<400> SEQUENCE: 248
gcagacccag acctcaagaa agggc                                              25

<210> SEQ ID NO 249
<211> LENGTH: 25
<212> TYPE: DNA
<213> ORGANISM: Artificial Sequence
<220> FEATURE:
<223> OTHER INFORMATION: Sonde

<400> SEQUENCE: 249
aggctgtaac cccccttaaa ctgcc                                              25

<210> SEQ ID NO 250
<211> LENGTH: 25
<212> TYPE: DNA
<213> ORGANISM: Artificial Sequence
<220> FEATURE:
<223> OTHER INFORMATION: Sonde

<400> SEQUENCE: 250
caactatggg gaacttaact ggagt                                              25

<210> SEQ ID NO 251
<211> LENGTH: 25
<212> TYPE: DNA
<213> ORGANISM: Artificial Sequence
<220> FEATURE:
<223> OTHER INFORMATION: Sonde

<400> SEQUENCE: 251
ggagtcgttt cagatgggtg cttac                                              25

<210> SEQ ID NO 252

<210> SEQ ID NO 252
<211> LENGTH: 24
<212> TYPE: DNA
<213> ORGANISM: Artificial Sequence
<220> FEATURE:
<223> OTHER INFORMATION: Sonde

<400> SEQUENCE: 252
ggcagtttaa gggggttac agcc                                        24

<210> SEQ ID NO 253
<211> LENGTH: 25
<212> TYPE: DNA
<213> ORGANISM: Artificial Sequence
<220> FEATURE:
<223> OTHER INFORMATION: Sonde

<400> SEQUENCE: 253
actccagtta agttccccat agttg                                      25

<210> SEQ ID NO 254
<211> LENGTH: 25
<212> TYPE: DNA
<213> ORGANISM: Artificial Sequence
<220> FEATURE:
<223> OTHER INFORMATION: Sonde

<400> SEQUENCE: 254
gtaagcaccc atctgaaacg actcc                                      25

<210> SEQ ID NO 255
<211> LENGTH: 25
<212> TYPE: DNA
<213> ORGANISM: Artificial Sequence
<220> FEATURE:
<223> OTHER INFORMATION: Sonde

<400> SEQUENCE: 255
gaagagtttc agcccttcag acaac                                      25

<210> SEQ ID NO 256
<211> LENGTH: 25
<212> TYPE: DNA
<213> ORGANISM: Artificial Sequence
<220> FEATURE:
<223> OTHER INFORMATION: Sonde

<400> SEQUENCE: 256
gatccaggtt tgtcacgcaa gctga                                      25

<210> SEQ ID NO 257
<211> LENGTH: 25
<212> TYPE: DNA
<213> ORGANISM: Artificial Sequence
<220> FEATURE:
<223> OTHER INFORMATION: Sonde

<400> SEQUENCE: 257
ccgagtgggc acatcaagca cagtg                                      25

<210> SEQ ID NO 258
<211> LENGTH: 25
<212> TYPE: DNA
<213> ORGANISM: Artificial Sequence
<220> FEATURE:
<223> OTHER INFORMATION: Sonde -continued

<400> SEQUENCE: 258
gttgtctgaa gggctgaaac tcttc                                              25

<210> SEQ ID NO 259
<211> LENGTH: 25
<212> TYPE: DNA
<213> ORGANISM: Artificial Sequence
<220> FEATURE:
<223> OTHER INFORMATION: Sonde

<400> SEQUENCE: 259
tcagcttgcg tgacaaacct ggatc                                              25

<210> SEQ ID NO 260
<211> LENGTH: 25
<212> TYPE: DNA
<213> ORGANISM: Artificial Sequence
<220> FEATURE:
<223> OTHER INFORMATION: Sonde

<400> SEQUENCE: 260
cactgtgctt gatgtgccca ctcgg                                              25

<210> SEQ ID NO 261
<211> LENGTH: 25
<212> TYPE: DNA
<213> ORGANISM: Artificial Sequence
<220> FEATURE:
<223> OTHER INFORMATION: Sonde

<400> SEQUENCE: 261
cacaggtctt gccgagaccc ccacg                                              25

<210> SEQ ID NO 262
<211> LENGTH: 25
<212> TYPE: DNA
<213> ORGANISM: Artificial Sequence
<220> FEATURE:
<223> OTHER INFORMATION: Sonde

<400> SEQUENCE: 262
ccacgggctc actgttcagc tcatc                                              25

<210> SEQ ID NO 263
<211> LENGTH: 25
<212> TYPE: DNA
<213> ORGANISM: Artificial Sequence
<220> FEATURE:
<223> OTHER INFORMATION: Sonde

<400> SEQUENCE: 263
gctctgtcac agtttcccac gactt                                              25

<210> SEQ ID NO 264
<211> LENGTH: 25
<212> TYPE: DNA
<213> ORGANISM: Artificial Sequence
<220> FEATURE:
<223> OTHER INFORMATION: Sonde

<400> SEQUENCE: 264
cgtgggggtc tcggcaagac ctgtg                                              25

<210> SEQ ID NO 265

```
<211> LENGTH: 25
<212> TYPE: DNA
<213> ORGANISM: Artificial Sequence
<220> FEATURE:
<223> OTHER INFORMATION: Sonde

<400> SEQUENCE: 265
gatgagctga acagtgagcc cgtgg                                    25

<210> SEQ ID NO 266
<211> LENGTH: 25
<212> TYPE: DNA
<213> ORGANISM: Artificial Sequence
<220> FEATURE:
<223> OTHER INFORMATION: Sonde

<400> SEQUENCE: 266
aagtcgtggg aaactgtgac agagc                                    25

<210> SEQ ID NO 267
<211> LENGTH: 25
<212> TYPE: DNA
<213> ORGANISM: Artificial Sequence
<220> FEATURE:
<223> OTHER INFORMATION: Sonde

<400> SEQUENCE: 267
ggccaaattg tgcacccct cccaa                                     25

<210> SEQ ID NO 268
<211> LENGTH: 25
<212> TYPE: DNA
<213> ORGANISM: Artificial Sequence
<220> FEATURE:
<223> OTHER INFORMATION: Sonde

<400> SEQUENCE: 268
aattcccagg acctcctaat atggc                                    25

<210> SEQ ID NO 269
<211> LENGTH: 25
<212> TYPE: DNA
<213> ORGANISM: Artificial Sequence
<220> FEATURE:
<223> OTHER INFORMATION: Sonde

<400> SEQUENCE: 269
ggtcgttgta ggcccagcac agtgg                                    25

<210> SEQ ID NO 270
<211> LENGTH: 25
<212> TYPE: DNA
<213> ORGANISM: Artificial Sequence
<220> FEATURE:
<223> OTHER INFORMATION: Sonde

<400> SEQUENCE: 270
ttgggagggg tggcacaatt tggcc                                    25

<210> SEQ ID NO 271
<211> LENGTH: 25
<212> TYPE: DNA
<213> ORGANISM: Artificial Sequence
<220> FEATURE:
<223> OTHER INFORMATION: Sonde
```

```
<400> SEQUENCE: 271
gccatattag gaggtcctgg gaatt                                         25

<210> SEQ ID NO 272
<211> LENGTH: 25
<212> TYPE: DNA
<213> ORGANISM: Artificial Sequence
<220> FEATURE:
<223> OTHER INFORMATION: Sonde

<400> SEQUENCE: 272
ccactgtgct gggcctacaa cgacc                                         25

<210> SEQ ID NO 273
<211> LENGTH: 25
<212> TYPE: DNA
<213> ORGANISM: Artificial Sequence
<220> FEATURE:
<223> OTHER INFORMATION: Sonde

<400> SEQUENCE: 273
cctagccatg agccaattcc ttgca                                         25

<210> SEQ ID NO 274
<211> LENGTH: 25
<212> TYPE: DNA
<213> ORGANISM: Artificial Sequence
<220> FEATURE:
<223> OTHER INFORMATION: Sonde

<400> SEQUENCE: 274
tgcaaggaat tggctcatgg ctagg                                         25
```